US008822688B2

(12) United States Patent
Samizu et al.

(10) Patent No.: US 8,822,688 B2
(45) Date of Patent: Sep. 2, 2014

(54) IMIDAZO[1,2-A]PYRIDINE DERIVATIVE

(71) Applicant: Astellas Pharma Inc., Chuo-ku (JP)

(72) Inventors: Kiyohiro Samizu, Chuo-ku (JP); Naoyuki Masuda, Chuo-ku (JP); Kazuhiko Iikubo, Chuo-ku (JP); Yohei Koganemaru, Chuo-ku (JP); Noriyuki Kawano, Tsukuba (JP); Junya Ohmori, Chuo-ku (JP); Yasuyuki Mitani, Chuo-ku (JP); Keni Ni, Chuo-ku (JP)

(73) Assignee: Astellas Pharma Inc., Chuo-ku (JP)

( * ) Notice: Subject to any disclaimer, the term of this patent is extended or adjusted under 35 U.S.C. 154(b) by 8 days.

(21) Appl. No.: 13/661,601

(22) Filed: Oct. 26, 2012

(65) Prior Publication Data

US 2013/0053363 A1 Feb. 28, 2013

Related U.S. Application Data

(63) Continuation-in-part of application No. PCT/JP2011/060098, filed on Apr. 26, 2011.

(30) Foreign Application Priority Data

Apr. 27, 2010 (JP) ................................. 2010-101557

(51) Int. Cl.
C07D 471/00 (2006.01)
C07D 491/00 (2006.01)
C07D 498/00 (2006.01)
C07D 513/00 (2006.01)
C07D 515/00 (2006.01)
C07D 487/00 (2006.01)
C07D 221/18 (2006.01)
C07D 221/22 (2006.01)
C07D 519/00 (2006.01)
C07D 471/04 (2006.01)
C07D 495/14 (2006.01)

(52) U.S. Cl.
CPC ............ C07D 471/04 (2013.01); C07D 519/00 (2013.01); C07D 495/14 (2013.01)
USPC .................... 546/70; 546/61; 546/85; 546/87

(58) Field of Classification Search
None
See application file for complete search history.

(56) References Cited

U.S. PATENT DOCUMENTS

2003/0229065 A1* 12/2003 Levy et al. ..................... 514/185
2005/0113397 A1* 5/2005 Takemura et al. ............. 514/267
2006/0160799 A1 7/2006 Alekshun et al.
2009/0163545 A1 6/2009 Goldfarb
2011/0071129 A1* 3/2011 Ando et al. ................ 514/210.16

FOREIGN PATENT DOCUMENTS

| JP | 2005-519998 A | 7/2005 |
| JP | 2008-504233 A | 2/2008 |
| WO | WO 03/064422 A1 | 8/2003 |
| WO | WO 2004/001058 A2 | 12/2003 |
| WO | WO 2004/001058 A3 | 12/2003 |
| WO | WO 2006/076009 A2 | 7/2006 |
| WO | WO 2006/076009 A3 | 7/2006 |
| WO | WO 2007/008541 A2 | 1/2007 |
| WO | WO 2007/008541 A3 | 1/2007 |
| WO | WO 2008/045664 A2 * | 4/2008 |
| WO | WO 2008/045664 A3 | 4/2008 |
| WO | WO 2009/154132 A1 * | 10/2009 |

OTHER PUBLICATIONS

Cornelison, TL. Human papillomavirus genotype 16 vaccines for cervical cancer prophylaxis and treatment. Curr. Opin. Oncol. 2000, vol. 12(5), p. 466.*
Brown, AS. et al. The Prevention of Schizophrenia. Schizophrenia Bulletin. 2011, vol. 37, p. 257.*
Garber, J. et al. Prevention of Depression in At-Risk Adolescents. JAMA. 2009, vol. 301, p. 2215.*
Cole, GM. et al. Prevention of Alzheimer's Disease. Neurobiology of Aging. 2005, vol. 26S, p. S133.*
Ruf, GS. et al. Biochemical effects of some derivatives of dipyrido[1,2-a:3',2'-d]imid-azole related to protein pyrolysates on rat liver microsomes. Carcinogenesis. 1984, vol. 5, p. 206.*
Kappe, T. et al. Benzimidazole Condensed Ring Systems, III [1]. Synthesis of Some Substituted 2,3-Dihydrocyclopenta-1H-[4',5':2,3]pyrido[1,2-a]benzimidazole-11-carbonitriles. Monatshefte fur Chemie. 1989, vol. 120, p. 74.*
CHEMCATS Chemical Library, CAS Registry No. 305335-00-6, Supplier: Otava, entered Nov. 30, 2000.*
Russell, RK. et al. The Synthesis of Cycloalkylpyrido[1,2-a]benzimidazole Carbonitrile Analogs. J. Heterocyclic Chem. 1995, vol. 32, p. 302.*
International Search Report and Written Opinion issued Jun. 7, 2011 in PCT/JP2011/060098 with English language translation.

(Continued)

Primary Examiner — Rita Desai
Assistant Examiner — Ben S Michelson
(74) Attorney, Agent, or Firm — Oblon, Spivak, McClelland, Maier & Neustadt, L.L.P.

(57) ABSTRACT

[Problem]
To provide a compound useful as medicine having PDE4B inhibitory activity, in particular, as an active ingredient of a composition for treating or preventing schizophrenia, Alzheimer's disease, dementia, depression and the like.
[Measures for Solution]
The present inventors examined compounds having PDE4B inhibitory activity and found that a tricyclic or tetracyclic imidazo[1,2-a]pyridine derivative or salts thereof had a superior PDE4B inhibitory activity, thereby completing the present invention. The imidazo[1,2-a]pyridine derivative can be used as an agent for treating or preventing schizophrenia, Alzheimer's disease, dementia, depression and the like.

12 Claims, No Drawings

(56) References Cited

OTHER PUBLICATIONS

El-Sayed A.M. Badawey, et al., "Benzimidazole condensed ring systems. XI. Synthesis of some substituted cycloalkyl pyrido [1,2-a] benzimidazoles with anticipated antineoplastic activity", European Journal of Medicinal Chemistry, vol. 34, 1999, pp. 663-667.

Esther Kellenberger, et al., "Identification of Nonpeptide CCR5 Receptor Agonists by Structure-based Virtual Screening", Journal of Medicinal Chemistry, vol. 50,No. 6, 2007, pp. 1294-1303.

S. K. Kotovskaya, et al., "Synthesis and Antiviral Activity of Fluorinated Pyrido [1,2-a] Benzimidazoles", Pharmaceutical Chemistry Journal, vol. 39, No. 11, 2005, pp. 574-578.

S. A. M. El-Hawash, et al., "Benzimidazole condensed ring systems. XII. Synthesis and anticancer evaluation of certain pyrido [1,2-a]benzimidazole derivatives[3]", Pharmazie, vol. 54, 1999, pp. 341-346 and cover page.

E. Badawey, et al., "Benzimidazole condensed ring system. IX. Potential antineoplastics. New Synthesis of some pyrido [1,2-a] benzimidazoles and related derivatives" European Journal of Medicinal Chemistry, vol. 30, 1995, pp. 327-332.

Ronald K. Russell, et al., "The Synthesis of Cycloalkylpyrido [1,2-a] benzimidazole Carbonitrile Analogs" J. Heterocyclic Chemistry, vol. 32, 1995, pp. 299-306.

Yu. M. Volovenko, et al., "Reactions of 1-Substituted Benzo [4,5] Imidazo [1,2-a] Pyridines", Chemistry of Heterocyclic Compounds, vol. 38, No. 2, 2002, pp. 213-218.

Mahendra Nath, et al., "An Expeditious Synthesis of Heteroarenes through Carbanion-Induced Ring Transformation Reactions of Suitable Functionalized Pyran-2-ones" European Journal of Organic Chemistry, 1998, pp. 2083-2088.

R. W. Sabnis, et al., "Synthesis of 2-N-(Benzo[b]thiophen-2-yl) benzo and heterofused-1,2,3-triazoles", J. Heterocyclic Chemistry, vol. 27, 1990, pp. 417-420.

Samia M. Rida, et al., "Benzimidazole Condensed Ring Systems. 2 [1]. New Synthesis of Substituted 1-Oxo-1H,5H-pyrido[1,2-a] benzimidazole-4-carbonitriles and Related Derivatives", J. Heterocyclic Chemistry, vol. 25, Nov.-Dec. 1988, pp. 1725-1728.

Samia M. Rida, et al., "Benzimidazole Condensed Ring Systems. 1. Syntheses and Biological Investigations of Some Substituted Pyrido [1,2-a]benzimidazoles", J. Heterocyclic Chemistry, vol. 25, Jul.-Aug. 1988, pp. 1087-1093.

Kazuo Kubo, et al., "Studies on the Syntheses of 2(1H)-Pyridone Derivatives. IV.[1]) Synthesis of Condensed Heterocyclic 2(1h)-Pyridones" Yakugaku Zasshi, vol. 99, 1979 pp. 880-888 with English abstract.

Hiroshi Takeshita, et al., "Novel pyridobenzimidazole derivatives exhibiting antifungal activity by the inhibition of β-1,6-glucan synthesis", Bioorganic & Medicinal Chemistry Letters, vol. 20, 2010, pp. 3893-3896.

CHEMICATS Chemical Library, RN: 305335-00-6, STN Entry Date: Nov. 30, 2000.

CHEMICATS Chemical Library, RN: 305331-71-9, STN Entry Date: Nov. 30, 2000.

Extended European Search Report issued Aug. 13, 2013 in Patent Application No. 11774973.9.

Sergey V. Ryabukhin, et al., "Chlorotrimethylsilane-Mediated Synthesis of Functionalized 2-(2-Hydroxybenzoyl)pyrido[1,2-a]benzimidazoles," SYNTHESIS, vol. 2007, No. 20, XP055074256, Oct. 1, 2007, pp. 3155-3162.

\* cited by examiner

IMIDAZO[1,2-A]PYRIDINE DERIVATIVE

CROSS REFERENCE TO RELATED APPLICATIONS

This application is a continuation-in-part of International Application No. PCT/JP2011/060098 filed on Apr. 26, 2011, which claims the benefit of Japan Patent Application. No. 2010-101557 filed on Apr. 27, 2010. The entire disclosures of International Application No. PCT/P2011/060098 and Japan Patent Application. No. 2010-101557 are incorporated by reference herein.

TECHNICAL FIELD

The present invention relates to a pharmaceutical composition, in particular, to an imidazo[1,2-a]pyridine derivative having PDE4B inhibitory activity and useful as an active ingredient of a therapeutic or preventive pharmaceutical composition for schizophrenia, Alzheimer's disease, dementia, depression and the like.

BACKGROUND ART

Schizophrenia is a psychological disorder showing diverse symptoms such as delusion, hallucination, hyperactivity, and depression. These symptoms are broadly classified as positive symptoms, negative symptoms, and cognitive disorders, Hitherto, in the treatment of schizophrenia, D2 receptor blockers such as haloperidol which is a typical first generation antipsychotic drug and Risperidone, Olanzapine, and the like, which are atypical second generation antipsychotic drugs have been discovered, and have exhibited some effects in the treatment of positive symptoms. However, side effects have been reported such as extrapyramidal symptoms with the first generation haloperidol or the like and metabolic disorders, for example, obesity, hyperglycemia, and the like with the second generation Risperidone, Olanzapine, and the like (Am. J. Psychiatry, 2003, 160: 1209-1222; Neuropsychopharmacology, 2003. 28: 1400-11; Diabetes Care, 2004, 27: 596; Japanese Journal of Clinical Psychopharmacology 2005, 8: 2151-64; Mol. Psychiatry. 2008, 13: 27-35). In addition, with conventional type drugs, the drug efficacy is insufficient with respect to negative symptoms or cognitive disorders (Schizophrenia Res, 2006, 88: 5-25; Japanese Journal of Clinical Psychopharmacology 2005, 8: 2151-64). In particular, in recent years, it has become common knowledge that cognitive disorders in schizophrenia are universally present, and while it has become clear that these disorders are greatly related to the prognosis, they are symptoms for which there is no effective therapeutic agent and for which there are medical unmet needs (Neuropsychology 1998, 12, 426-45; Am. J. Psychiatry 1996, 153: 321-30; Schizophrenia Bulletin 2000, 26: 119-36).

Dementia is a syndrome in which brain function is deteriorated by acquired brain disorders, and which is based on memory disorders and judgment disorders, and vascular dementia and Alzheimer's disease (below abbreviated to AD) are representative primary diseases. Hitherto, these therapeutic agents have been researched; however, the clinical satisfaction level is not sufficient. For example, with cholinesterase inhibitors such as donepezil which are widely used as therapeutic agents for AD, it has been reported that the effect is not sufficient (Curr. Neurol. Neurosci. rep., 2005, 5(6): 455-457; Eur. J. Pharmacol., 1998, 346: 1-13). Further, side effects due to stimulating the peripheral cholinergic nervous system have been noted (Cuff. Psychiatry Rep., 2000, 2(6): 473-478; J. Psychopharmacol., 2000, 14(4): 406-408). Further, NMDA antagonists such as memantine have been approved in some countries; however, side effects have been particularly noted in patients having psychological disorders such as cognitive disorders, hallucinations, ataxia, and mental diseases (J. Clin. Psychiatry. 2005, 66(5): 658-659; Learning & memory, 2001, 8: 20-25).

Against the above background, there is a demand for safe and highly effective therapeutic agents for schizophrenia and therapeutic agents for dementia.

It is known that cAMP-specific phosphodiesterase-4 (PDE4) is an enzyme related to second messenger cAMP regulation and deeply related to learning and memory functions (Science 1993, 260: 1661-4). It has been shown that PDE4 inhibitors promote neuronal plasticity in vitro, and improve or promote learning and memory in various models in vivo (PNAS 1998, 95: 15020-5; Current Pharmaceutical Design 2005, 11: 3329-34). Further, cAMP synthetic enzyme activity is decreased in AD patients and decrease in cAMP signal transduction in a pathological condition can be assumed (Neurobiol Aging 1997, 18: 275-9). Furthermore, some medical effects have been observed when treating human dementia patients with denbufylline, which is a PDE4 inhibitor (Biol Psychiatry 1992, 32: 668-81). However, vomiting is known as a common side effect of PDE4 inhibitors and this is an obstacle to development. In this regard, based on studies of brain expression and genetically modified mice, the possibility that the vomiting is mainly related to PDE4D has been suggested (Current Pharmaceutical design 2009, 15, 1693).

In addition, the relationship between PDE4B and schizophrenia has steadily become clearer in recent years. DISC1 (disrupted-in-schizophrenia 1) is a susceptible gene to schizophrenia and it has been shown that there is an interaction between PDE4B and DISC1, indicating that PDE4B is an important drug target (Current opinion Neurobiol 2007, 17: 95-102). In patients with schizophrenia, deterioration of the cAMP/PICA signal cascade function due to reduction in the brain PDE4B expression has been suggested (Schizophrenia Res 2008, 101: 36-49, 2008; J Neurochem 2002, 81: 745-57), indicating that PDE4B inhibitors are highly potential therapeutic agents for schizophrenia.

In addition, the fact that the classic PDE4 inhibitor rolipram has strong antidepressant effects has been confirmed in clinical trials; however, launching thereof has not been achieved due to the vomiting side effect (Current Therapeutic Res 1988, 43: 291-5). In recent years, since a relationship between PDE4B and depression is suggested (Psychopharmacol 2008, 197: 115-26) from analysis of PDE4B knockout mice, it is expected that there is a possibility that the PDE4B inhibitors will be able to avoid the vomiting side effect while having potent antidepressant effects.

Therefore, it can be believed that drugs inhibiting PDE4B are effective in the treatment or prevention of schizophrenia, Alzheimer's disease, dementia, depression, and the like.

In the chemical library of non-patent document 1, a structural formula of the compound represented by formula (A) is disclosed; however, there is no description of the PDE4 (PDE4B) inhibitory activity or of medicinal use with respect to schizophrenia, Alzheimer's disease, dementia, depression and the like.

[Chem. 1]

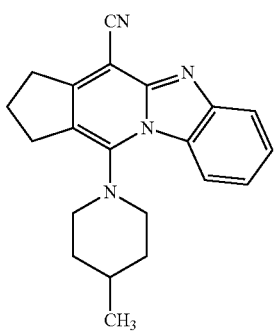

(A)

In the chemical library of non-patent document 2, a structural formula of the compound represented by formula (B) is disclosed; however, there is no description of the PDE4 (PDE4B) inhibitory activity or of medicinal use with respect to schizophrenia, Alzheimer's disease, dementia, depression and the like.

[Chem. 2]

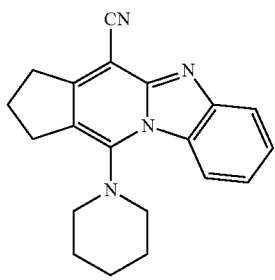

(B)

In patent document 1, as one of the examples having various structures, it is reported that the compound represented by formula (C) in example 25 inhibits PDE4 and is useful in the treatment of inflammatory disease; however, there is no description of effectiveness for schizophrenia, Alzheimer's disease, dementia, depression and the like.

[Chem. 3]

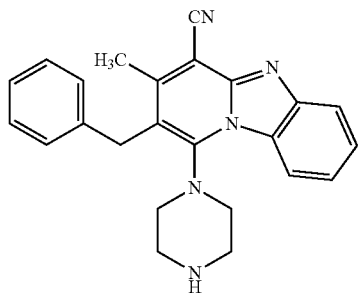

(C)

In patent document 2, as one of the examples having various structures, it is reported that the compound represented by formula (D) in example AAE has a microbial transcription factor regulation ability; however, there is no mention relating to PDE4 (PDE4B) inhibitory activity or description of effectiveness for schizophrenia, Alzheimer's disease, dementia, depression and the like.

[Chem. 4]

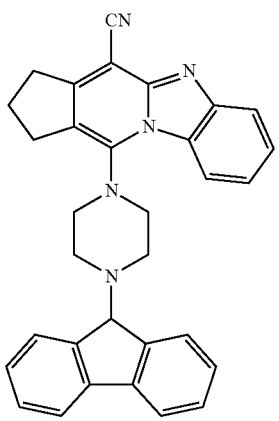

(D)

In patent document 3, it is reported that compound represented by formula (E) is effective as an antifungal agent; however, there is no mention relating to PDE4 (PDE4B) inhibitory activity or description of effectiveness for schizophrenia, Alzheimer's disease, dementia, depression and the like,

[Chem. 5]

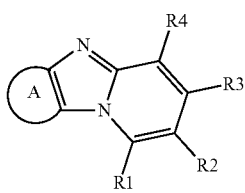

(E)

(In the formula, A moiety is a benzene ring or the like, R1 is a monocyclic, bicyclic, or spirocyclic heterocyclic ring or the like of from 3 to 10 carbon atoms, R2 is an alkyl group or the like, or R1 and R2 may be put together and form a heterocyclic group of a 5-membered ring or 6-membered ring, R3 is an alkyl group or the like, and R4 is a cyano group,

[Chem. 6]

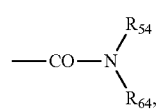

or the like.

For other details, refer to the Gazette.)

In patent document 3, as specific examples of the compound represented by (E), for example, the compound and the like of formula (F) are disclosed.

[Chem. 7]

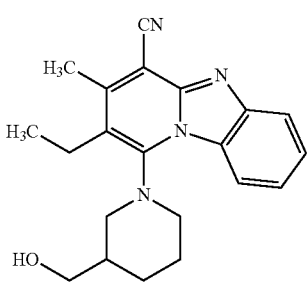

(F)

In non-patent document 3, a synthesis method of the compounds shown by formula (G) and formula (H) is disclosed; however, there is no mention relating to PDE4 (PDE4B) inhibitory activity or description of effectiveness for schizophrenia, Alzheimer's disease, dementia, depression and the like,

[Chem. 8]

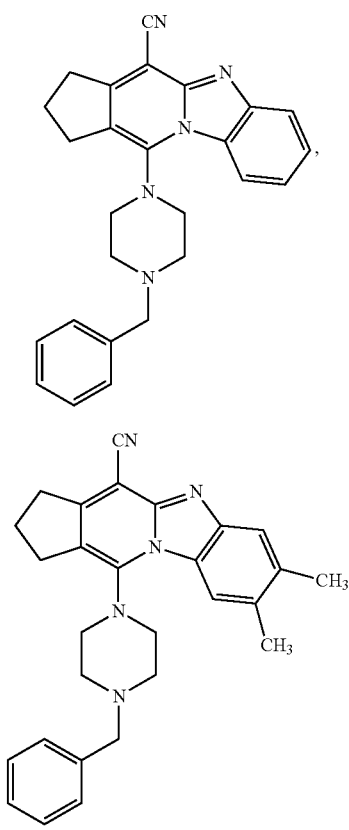

RELATED ART

Patent Document

Patent document 1: Pamphlet of International Publication 2008/045664
Patent document 2: Pamphlet of International Publication 2004/001058
Patent document 3: Pamphlet of International Publication 2003/064422

Non-Patent Document

Non-patent document 1: CHEMCATS Chemical Library, CAS Registry No. 305335-00-6, Supplier: Otava
Non-patent document 2: CHEMCATS Chemical Library, CAS Registry No. 305331-71-9, Supplier: AsInEx
Non-patent document 3: Journal of Heterocyclic Chemistry (1995), 32(1), 299-306

DISCLOSURE OF INVENTION

Problems to be Solved by the Invention

The object of the present invention is to provide a drug having a PDE4B inhibitory activity, in particular, an imidazo[1,2-a]pyridine derivative useful as an active ingredient of a therapeutic or preventive pharmaceutical composition for schizophrenia, Alzheimer's disease, dementia, depression and the like.

Measures for Solving the Problems

As a result of studying the compounds inhibiting PDE4B, the present inventors found that an imidazo[1,2-a]pyridine derivative or a salt thereof has a superior PDE4B inhibitory activity, and thereby completed the present invention.

Thus, the present invention relates to the compound of the formula (I) or a pharmaceutically acceptable salt thereof as well as a pharmaceutical composition comprising the compound of the formula (I) or a pharmaceutically acceptable salt thereof and a pharmaceutically acceptable excipient.

[Chem. 9]

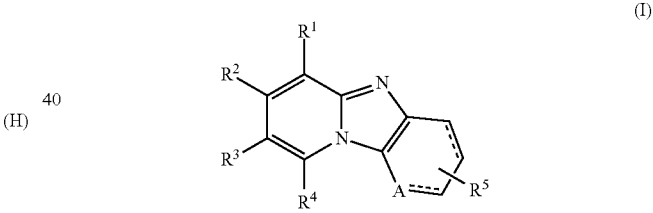

(I)

(In the formula,
$R^1$ represents —H, —CN, —CONH$_2$, or lower alkyl or acyl which may have substituent(s);
$R^2$ represents —H, lower alkyl which may have substituent(s), aryl, a heterocyclic group which may have substituent(s), or amino or acyl which may have substituent(s);
$R^3$ represents —H, halogen, lower alkyl which may have substituent(s), —O-lower alkyl, —S-lower alkyl, —SO-lower alkyl, or —SO$_2$-lower alkyl or acyl; or, $R^2$ and $R^3$ are bonded together to form a cycloalkyl ring or a monocyclic saturated hetero ring in which one cyclic atom is a hetero atom, which is condensed with an adjacent ring, wherein the cycloalkyl ring and the monocyclic saturated hetero ring may have bridge(s) and may have substituent(s);
$R^4$ represents —H, aryl which may have substituent(s), amino which may have substituent(s), or a heterocyclic group which may have substituent(s);
$R^5$ represents —H, halogen, lower alkyl which may have substituent(s), —O-lower alkyl, —CO—O-lower alkyl, or —SO$_2$—R$^6$;

$R^6$ represents amino or a heterocyclic group which may have one or two substituent(s);

A represents CH, CH$_2$, or N; and a dotted line represents that the site may form a double bond.)

In addition, unless specifically stated, in a case where the symbols in the chemical formula in the present specification are also used in other chemical formulas, the same symbols indicate the same meaning.

In addition, the present invention relates to a PDE4B inhibitor containing the compound of formula (I) or a pharmaceutically acceptable salt thereof, and to an agent for the treatment or prevention of schizophrenia, Alzheimer's disease, dementia, or depression.

Further, the present invention relates to the use of compound of formula (I) or a pharmaceutically acceptable salt thereof for preparing a drug for the treatment or prevention of schizophrenia, Alzheimer's disease, dementia, or depression; the compound of formula (I) or a pharmaceutically acceptable salt thereof for the treatment or prevention of schizophrenia, Alzheimer's disease, dementia, or depression; and a treatment or prevention method for schizophrenia, Alzheimer's disease, dementia, or depression involving administering patients with an effective amount of the compound of formula (I) or a pharmaceutically acceptable salt thereof.

Effects of the Invention

The compound of formula (I) or a pharmaceutically acceptable salt thereof has a PDE4B inhibitory action and can be used as an agent for the treatment or prevention of schizophrenia, Alzheimer's disease, dementia, or depression.

EMBODIMENTS FOR CARRYING OUT THE INVENTION

Below, the present invention will be described in detail.

In the present specification, "lower alkyl" means a linear chain or branched chain alkyl having 1 to 6 carbon atoms (below, abbreviated as $C_{1-6}$), for example, a methyl, ethyl, n-propyl, isopropyl, n-butyl, isobutyl, sec-butyl, tert-butyl, n-pentyl, n-hexyl group, or the like, as another embodiment, is a $C_{1-4}$ alkyl, and, as a further embodiment, means methyl and ethyl, In the present specification, "lower alkylene" means a linear chain or branched chain $C_{1-6}$ alkylene, for example, methylene, ethylene, trimethylene, tetramethylene, pentamethylene, hexamethylene, propylene, methylmethylene, ethylethylene, 1,2-dimethylethylene, 1,1,2,2-tetramethylethylene, 2,2-dimethyltrimethylene, 2,2-dimethyl tetramethylene, or the like, and, as another embodiment, means trimethylene, tetramethylene, 2,2-dimethyl trimethylene, and 2,2-dimethyl tetramethylene.

In the present specification, the "bridge" in "may have a bridge" means a bridge with a lower alkylene, for example, methylene, ethylene, trimethylene, tetramethylene, pentamethylene, hexamethylene, or the like, as another embodiment, means a bridge with methylene and ethylene, and, as a further embodiment, means a bridge with methylene.

In the present specification, "hetero ring" in a "heterocyclic group" means cyclic groups selected from i) a 3- to 8-membered monocyclic hetero ring containing 1 to 4 hetero atoms selected from oxygen, sulfur, and nitrogen, as another embodiment, a 5- to 7-membered monocyclic hetero ring containing 1 to 4 hetero atoms selected from oxygen, sulfur, and nitrogen, as another embodiment, and ii) bi- or tricyclic hetero rings containing 1 to 5 hetero atoms selected from oxygen, sulfur and nitrogen, in which the monocyclic hetero ring condenses and forms one or two rings selected from a group formed of a monocyclic hetero ring, a benzene ring, a $C_{5-8}$ cycloalkane and $C_{5-8}$ cycloalkene. An oxide or dioxide in which the sulfur or nitrogen, which are the ring atoms, may be formed.

As the "heterocyclic group", the following embodiments may be exemplified.

(1) Monocyclic Saturated Heterocyclic Groups (a) Those including 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, and the like;

(b) Those including 1 to 3 nitrogen atoms, 1 to 2 sulfur atoms, and/or 1 to 2 oxygen atoms, for example, thiomorpholinyl, thiazolidinyl, isothiazolidinyl, oxazolidinyl, morpholinyl, and the like;

(c) Those including 1 to 2 sulfur atoms, for example, tetrahydrothiopyranyl and the like;

(d) Those including 1 to 2 sulfur atoms and 1 to 2 oxygen atoms, for example, oxathiolanyl and the like;

(e) Those including 1 to 2 oxygen atoms, for example, oxiranyl, oxetanyl, dioxolanyl, tetrahydrofuranyl, tetrahydropyranyl, 1,4-dioxanyl, and the like;

(2) Monocyclic Unsaturated Heterocyclic Groups (a) Those including 1 to 4 nitrogen atoms, for example, pyrrolyl, imidazolyl, pyrazolyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) Those including 1 to 3 nitrogen atoms, 1 to 2 sulfur atoms, and/or 1 to 2 oxygen atoms, for example, thiazolyl, isothiazolyl, thiadiazolyl, dihydrothiazinyl, oxazolyl, isoxazolyl, oxadiazolyl, oxadinyl, and the like;

(c) Those including 1 to 2 sulfur atoms, for example, thienyl, thiepinyl, dihydrodithiopyranyl, dihydrodithionyl, and the like;

(d) Those including 1 to 2 sulfur atoms and 1 to 2 oxygen atoms, specifically, dihydrooxathiopyranyl, and the like;

(e) Those including 1 to 2 oxygen atoms, for example, Daryl, pyranyl, oxepinyl, dioxolyl, and the like;

(3) Condensed Polycyclic Saturated Heterocyclic Groups (a) Those including 1 to 5 nitrogen atoms, for example, quinuclidinyl, 7-azabicyclo[2.2.1]heptyl, 3-azabicyclo[3.2.2]nonanyl, and the like;

(b) Those including 1 to 4 nitrogen atoms, 1 to 3 sulfur atoms, and/or 1 to 3 oxygen atoms, for example, trithiadiazaindenyl, dioxoloimidazolidinyl, and the like;

(c) Those including 1 to 3 sulfur atoms and/or 1 to 3 oxygen atoms, for example, 2,6-dioxabicyclo[3.2.2]oct-7-yl, and the like;

(4) Condensed Polycyclic Unsaturated Heterocyclic Groups (a) Those including 1 to 5 nitrogen atoms, for example, indolyl, isoindolyl, indolinyl, indolizinyl, benzimidazolyl, dihydrobenzimidazolyl, tetrahydrobenzimidazolyl, quinolyl, tetrahydroquinoxalyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, and the like;

(b) Those including 1 to 4 nitrogen atoms, 1 to 3 sulfur atoms, and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxadinyl, benzoxadiazolyl, benzoisothiazolyl, benzoisooxazolyl, and the like;

(c) Those including 1 to 3 sulfur atoms, for example, benzothienyl, benzodithiopyranyl, dibenzo[b,d]thienyl, and the like;
(d) Those including 1 to 3 sulfur atoms and 1 to 3 oxygen atoms, for example, benzoxathiopyranyl, phenoxazinyl, and the like;
(e) Those including 1 to 3 oxygen atoms, for example, benzodioxolyl, benzofuranyl, dihydrobenzofuranyl, isobenzofuranyl, chromanyl, chromenyl, dibenzo[b,d]furanyl, methylenedioxyphenyl, ethylenedioxyphertyl, and the like; and the like.

In addition, these hetero rings may form Spiro ring with the monocyclic saturated hetero ring or described in (1).

In the present specification, "halogen" means F, Cl, Br, and I.

In the present specification, "may have substituent(s)" means unsubstituted or having 1 to 5 substituents, and, as another embodiment, means unsubstituted or having 1 to 3 substituents. In addition, in a case of having a plurality of substituents, those substituents may be the same or may be different from each other.

In the present specification, "substituent" in "may have substituent(s)" means all substituents generally used by those skilled in the art, and, as another embodiment, means halogen, lower alkyl, mono- or di-OH substituted lower alkyl, -lower alkylene amine, —O-lower alkyl, cyano, aryl, heterocyclic groups, acyl, and the like.

In the present specification, "substituent" in the "heterocyclic group which may have substituent(s)" means lower alkyl, mono- or di-OH substituted lower alkyl, —O-lower alkyl, -lower alkylene-(amines which may be protected), cyano, and halogen, and, as another embodiment, means methyl, —CH$_2$OH, —O—CH$_3$, —CH$_2$— (amines which may be protected), cyano and —F.

In the present specification, "may be protected" in "-lower alkylene-(amine which may be protected)" means that an amine group substituted with -lower alkylene may be protected by an amino-protecting group generally used by those skilled in the art, and, in another embodiment, means that the amine group may be protected by a benzyloxycarbonyl group (Cbz group).

In the present specification, "aryl" is a $C_{6-14}$ monocyclic to tricyclic aromatic hydrocarbon ring group, and includes a partially hydrogenated ring group. For example, it may be phenyl, naphthyl, 5-tetrahydronaphthyl, 4-indenyl, 1-fluorenyl, and the like.

In the present specification, "acyl" may include the following acyl groups.
(1) Aliphatic acyl groups. Specifically, examples thereof include —CHO, —CO-lower alkyl, —CO-lower alkenyl, —CO-lower alkylene-O-lower alkyl, —CO-cycloalkyl, —CO-cycloalkenyl, and the like.
(2) Acyl groups including aryl. Specifically, examples thereof include —CO-aryl, —CO-lower alkylene-aryl, —CO-loweralkenylenearyl, —CO-lower alkylene-O-aryl, and the like.
(3) Acyl groups including a hetero ring. Specifically, examples thereof include —CO-heterocyclic groups, —CO-lower alkylene-heterocyclic groups, —CO-lower alkenylene-heterocyclic groups, and the like.

In the present specification, "$R^2$ and $R^3$ are bonded together to form a cycloalkyl ring condensed with an adjacent ring, or a monocyclie saturated hetero ring in which one cyclic atom is a hetero atom" means including cases where the bond between two carbon atoms in the cyclic structure of formula (I) in which $R^2$ and $R^3$ are respectively bonded is single bond or double bond.

Embodiments of the compound of formula (I) are shown below.
(1) A compound wherein $R^1$ is —CONH$_2$.
(2) A compound wherein $R^2$ and $R^3$ are bonded together to form a cycloalkyl ring or a monocyclic saturated hetero ring in which one cyclic atom is a hetero atom, which is condensed with an adjacent ring, wherein the cycloalkyl ring and the monocyclic saturated hetero ring may have bridge(s) and may have substituent(s). Another embodiment is the compound wherein $R^2$ and $R^3$ are bonded together to form

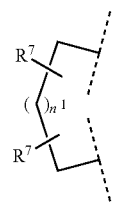

[Chem. 10]

(in the formula, $n^1$ is 1 or 2, $R^7$ are the same or different from each other and H or methyl), as another embodiment, $R^2$ and $R^3$ are bonded together to form

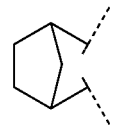

[Chem. 11]

and, as yet another embodiment, $R^2$ and $R^3$ are bonded together to form

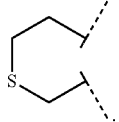

[Chem. 12]

(3) A compound wherein $R^4$ is a heterocyclic group which may have substituent(s). As another embodiment, the compound wherein $R^4$ is

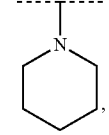

[Chem. 13]

as another embodiment,

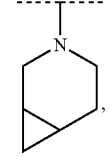

[Chem. 14]

as another embodiment,

as another embodiment,

Any of these four types of hetero ring may have one or more substituents selected from a group consisting of a lower alkyl, a mono- or di-OH substituted lower alkyl, —O-lower alkyl, a -lower alkylene-(amine which may be protected), cyano and halogen, and, as another embodiment, may have one or more substituents selected from a group formed of methyl, —$CH_2OH$, —O—$CH_3$, —$CH_2$—(amine which may be protected), cyano and —F.

(4) the compound wherein $R^5$ is —H.
(5) the compound wherein A is CH, and, as another embodiment, $CH_2$.
(6) A compound which is a combination of two or more of the embodiments described in the above (1) to (5).

An embodiment of the compound of formula (I) or a pharmaceutically acceptable salt thereof is the compound of formula (I-b) below or a pharmaceutically acceptable salt.

[Chem. 17]

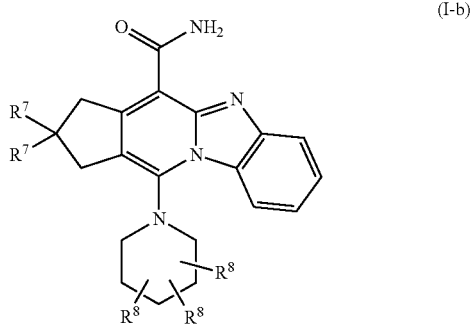

(I-b)

In addition, the embodiment which is the compound of the formula (I-b) is shown below.
(7) the compound wherein $R^7$ is H or methyl.
(8) the compound wherein $R^{13}$ are the same or different from each other and are H, methyl, —$CH_2OH$, —O—$CH_3$, —$CH_2NH_2$, cyano or —F.
(9) A compound which is a combination of two or more of the embodiments described in the above (7) to (8).

An embodiment of the compound of formula (I) or a pharmaceutically acceptable salt thereof is a compound selected from the group below or a pharmaceutically acceptable salt thereof.

rel-11-[(3R,4S)-3-fluoro-4-(hydroxymethyl)-4-methoxypiperidin-1-yl]-2,2-dimethyl-2,3-dihydro-1H-cyclopenta[4,5]pyrido[1,2-a]benzimidazole-4-carboxamide, 11-[4-(hydroxymethyl)-4-methoxypiperidin-1-yl]-2,3-dihydro-1H-cyclopenta[4,5]pyrido[1,2-a]benzimidazole-4-carboxamide, rel-11-[(3R,4S)-3-fluoro-4-(hydroxymethyl)-4-methoxypiperidin-1-yl]-2,3-dihydro-1H-cyclopenta[4,5]pyrido[1,2-a]benzimidazole-4-carboxamide, 11-[4-(hydroxymethyl)-4-methoxypiperidin-1-yl]-2,2-dimethyl-2,3-dihydro-1H-cyclopenta[4,5]pyrido[1,2-a]benzimidazole-4-carboxamide, 11-[4-(hydroxymethyl)-4-methoxypiperidin-1-yl]-7,8,9,10-tetrahydro-7,10-methanobenzimidazo[1,2-b]isoquinoline-6-carboxamide, 11-[4-(hydroxymethyl)-4-methylpiperidin-1-yl]-9,9-dimethyl-7,8,9,10-tetrahydrobenzimidazo[1,2-b]isoquinoline-6-carboxamide, and 11-[4-(hydroxymethyl)-4-methylpiperidin-1-yl]-2,3-dihydro-1H-cyclopenta[4,5]pyrido[1,2-a]benzimidazole-4-carboxamide.

In the compound of formula (I), depending on the type of substituents, tautomers and geometric isomers may be present. In the present specification, the compounds of (I) is described with only embodiment of an isomer; however, the present invention also includes ones in which other isomers are included and the isomers are separated, or mixtures thereof.

In addition, in the compound of formula (I), there are cases where asymmetric carbon atoms and axial chirality are present and, optical isomers based thereon may be present. The present invention also includes ones in which the optical isomers of the compound of formula (I) are separated, or mixtures thereof.

In addition, the present invention also includes a pharmaceutically acceptable prodrug of the compound shown by formula (I). The pharmaceutically acceptable prodrug is a compound that is converted into the compounds of the present invention by solvolysis or under physiological conditions. As groups to form the prodrug, for example, the groups described in Prog. Med., 5, 2157-2161 (1985) and "Pharmaceutical Research and Development" (Hirokawa Publishing Company, 1990) Volume 7 Drug Design 163-198, may be exemplified.

In addition, there are cases when the compounds of formula (I) form an acid addition salt or a salt with a base depending on the type of substituents, and the present invention includes pharmaceutically acceptable salts of the compound of formula (I). Specifically, examples include inorganic acids such as hydrochloric acid, hydrobromic acid, hydroiodic acid, sulfuric acid, nitric acid, and phosphoric acid; acid addition salts with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, and glutamic acid; inorganic bases such as sodium, potassium, magnesium, calcium, and aluminum; salts with organic bases such as methylamine, ethylamine, ethanolamine, lysine, and ornithine; and salts with various amino acids and amino acid derivatives such as acetyl-leucine; ammonium salts, or the like.

In addition, the present invention also includes hydrates or solvates of the compound of formula (I) and pharmaceutically acceptable salts thereof and crystal polymorphic substances. In addition, the present invention also includes various compounds labeled as radioactive or non-radioactive isotopes.

(Preparation Method)

The compound of formula (I) and pharmaceutically acceptable salts thereof can be prepared using characteristics based on the basic structure thereof or the types of substituents and applying various types of well-known synthesis method. At such a time, according to the type of functional group, there are cases where it is effective in terms of preparation technique to replace the functional group with an appropriate protecting group (group capable of easily being transformed into the functional group) at the stage of reaching the intermediate from the starting material. Examples of such a protecting group, for example, include the protecting groups and the like described in Wuts (P. G. M. Wuts) and Greene (T. W. Greene), "Greene's Protective Groups in Organic Synthesis (4$^{th}$ Edition, 2006)", which may be appropriately selected and used according to the reactions conditions thereof. In these methods, after the protecting group is introduced and the reaction performed, by removing the protecting group as necessary, it is possible to obtain the desired compound.

In addition, the prodrug of the compound of formula (I) can be prepared by introducing a specific group at the stage reaching the intermediate from the starting material in the same manner as the above-described protecting group or using the resulting compound of formula (I) and further performing the reaction. The reaction can be performed by applying a method known to those skilled in the art such as normal esterification, amidation, and dehydration.

Below, description will be given of a typical preparation method of the compound of formula (I). Each preparation method can be performed with reference to the reference literature included with the description. Here, the preparation method of the compound of the present invention is not limited to the examples shown below.

Preparation Method

[Chem. 18]

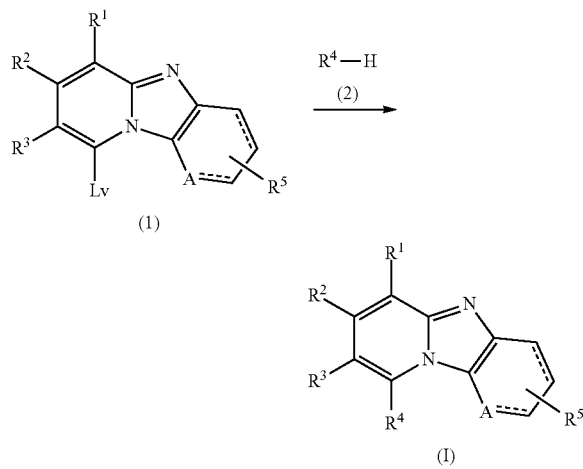

(In the formula, Lv represents a leaving group. The same shall apply hereinafter.)

The preparation method is a method for preparing the compound of formula (I) using a nucleophilic substitution reaction of compound (1) and compound (2). Here, examples of the leaving groups include halogen, methanesulfonyloxy, methylsulfinyl, methylsulfonyl, p-toluenesulfonyloxy groups, or the like.

In this reaction, using equivalent amounts of compound (1) and compound (2) or an excess amount of one of these, the mixture thereof is normally stirred for from 5 seconds to 5 days in an inert solvent or in the absence of a solvent, from under cooling to under reflux heating, in some cases under microwave irradiation, and preferably at 0° C. to 300° C. Examples of solvent used herein are not particularly limited; however, aromatic hydrocarbons such as benzene, toluene, and xylene; ethers such as diethyl ether, tetrahydrofuran, dioxane, and dimethoxyethane; halogenated hydrocarbons such as dichloromethane, 1,2-dichloroethane, and chloroform; N,N-dimethyl formamide, N-methylpyrrolidone, 1,3-dimethyl-2-imidazolidinone, dimethyl sulfoxide, ethyl acetate, acetonitrile and mixtures thereof may be exemplified. Performing the reaction in the presence of an organic base such as triethylamine, N,N-diisopropylethylamine, or N-methylmorpholine, or an inorganic base such as potassium carbonate, sodium carbonate, or potassium hydroxide may be advantageous in terms of causing the reaction to proceed smoothly.

LITERATURE

S. R. Sandler and W. Karo, "Organic Functional Group Preparations", 2$^{nd}$ Edition, Volume 1, Academic Press Inc., 1991

"Jikken Kagaku Koza" (Courses in Experimental Chemistry) (5$^{th}$ Edition)" edited by the Chemical Society of Japan, Volume 14 (2005) (Maruzen)

(Preparation of Starting Compounds)

The starting materials of the above-described compound (1) and compound (2) used in the preparation of the compound of the present invention can be prepared from available well-known compounds by applying methods described in the following Preparation Examples, methods obvious to those skilled in the art, or modified methods thereof.

The compound of formula (I) is isolated and purified as a free compound, a pharmaceutically acceptable salt thereof, a hydrate or solvate of these, or a crystal polymorphic substance. The pharmaceutically acceptable salt of the compound of formula (I) can be prepared by being subjected to a salt forming reaction with a normal method.

The isolation and purification is performed by applying normal chemical operations such as extraction, fractional crystallization, and various types of fractional chromatography.

Various isomers can be prepared by selecting the appropriate starting compounds, or can be separated using the difference between the physical and chemical properties of the isomers. For example, optical isomers are obtained using a general optical resolution method of a racemic body (for example, fractional crystallization guided by a diastereomeric salt with an optically active base or acid, or chromatography using a chiral column or the like) and can be prepared from an appropriate optically active starting compound.

The pharmacological activity of the compounds of formula (I) was confirmed by the following tests.

Test Method 1: Human PDE4B Inhibitory Activity (1) Purification of Human PDE4B Enzyme Plasmid DNA encoding FLAG-tagged human PDE4B2 was prepared and transfected into E. coli, and mass cultivation was performed. After extracting and purifying the plasmid DNA from the E. coli, the resultant was transfected into COS-1 cells and cultured. After the cells were homogenized, the expressed enzyme was purified using a FLAG peptide affinity column.

(2) Human PDE4B Activity Inhibition Test

1 µl/well of DMSO solution in which various concentrations of test compounds were dissolved and 74 µl/well of the purified enzyme diluted with a buffer were added to 96-well plates, and incubated at room temperature for 10 minutes. A buffer including 40 nM [$^3$H]-cAMP (Amersham, TRK559) and 4 µM cAMP were added at 25 µl/well and reacted for 30 minutes at room temperature. A suspension (18 mM $ZnSO_4$, 5 mM IBMX, distilled water) of polylysin coated yttrium silicate SPA beads (Amersham, RPNQ0010) was added at 50 µl/well, and the reaction was stopped. After standing for 20 minutes at room temperature, the radioactivity was measured using a top count instrument and set as an index of enzyme activity. For evaluating the enzyme inhibitory activity of the test compound in each experiment, a value of $IC_{50}$ was calculated with the radiation activity of the well of adding the vehicle (DMSO) and the enzyme as 0% inhibition and the radiation activity of the well of adding only the vehicle and not adding the enzyme as 100% inhibition.

The test results are shown in Table 1. Ex indicates the following example compound numbers.

TABLE 1

| Ex | $IC_{50}$ (nM) | Ex | $IC_{50}$ (nM) |
|---|---|---|---|
| 2 | 13 | 4 | 86 |
| 5 | 14 | 8 | 8 |
| 10 | 48 | 12 | 2.7 |
| 14 | 3.3 | 15 | 26 |
| 16 | 15 | 18 | 18 |
| 22 | 11.8 | 23 | 42 |
| 25 | 8.2 | 26 | 13 |

As the results of these tests, it was revealed that the compound of formula (I) had a human PDE4B inhibitory activity.

Test Method 2: Improving Effects on MK-801 Induced Spontaneous Alternation Behavior Deficits in Mice MK-801 induced cognitive deficits reflect both the low glutamate hypothesis in schizophrenia and the low glutamate signal transduction in dementia. Spontaneous alternation behavior is a task of reflecting working memory, and marked deficits of this working memory are involved in both schizophrenia and dementia. Therefore, the improving effects of the compounds of formula (I) on cognitive deficits were evaluated using the test method described above which is known as a model of short-term learning disability.

(1) Animals

Species: male ddY mice

Number of animals per group: 6 to 9

Age when used: 5 weeks old

Supplier or breeder: Japan SLC (2) Measurement Method

The mice were transported to the experiment room one hour before the start of the trial. The mice were put into one end of an arm of a maze (Y-maze) having arms of the same length in three directions and allowed to explore freely for 8 minutes, and the number of entries to the arms during this period was counted. Three continuous entries to different arms were set as spontaneous alternation behavior and a ratio of it to the number of total arm entries was calculated using the following formula as a spontaneous alternation rate.

The spontaneous alternation rate (%) the number of spontaneous alternation behavior/(the number of total arm entries−2)×100

The test compound was administered orally 50 minutes before the start of the test, and 30 minutes later, 0.5 mg/kg scopolamine or 0.15 mg/kg MK-801 (or saline for the normal group) was administered intraperitoneally. Here, in the normal group (administered with saline) and the control group (administered with 0.5 mg/kg scopolamine or 0.15 mg/kg MK-801), a vehicle was administered orally at the time of administration of the test compound.

(3) Data Analysis

The spontaneous alternation rate (%) is shown by an average value (mean±SE) in each group. In a case where a significant difference (Student's t test) in the spontaneous alternation rate (%) was observed between the normal group and the control group, it was judged that a learning deficits by administration of MK-801 were established. By performing Dunnett's test of the test compound administration group against the control group, the presence or absence of improving effects of the test compound was determined. In each test, $p<0.10$ was judged as a trend, and $p<0.05$ was judged as a significant difference.

As the results of this test, it was revealed that the compound of formula (I) suppressed MK-801 induced spontaneous alternation behavior deficits in a range of administration of 0.001 to 100 mg/kg, indicating an effect on schizophrenia and dementia.

Test Method 3: Toxicity Test

By performing the toxicity tests described below, it is possible to confirm the safety relating to the genotoxicity of the compounds of formula (I).

(1) Ames Test

The Ames test can be performed using a method known to those skilled in the art, for example, the method described in Mutation Research, 113 (1983) 173-215.

(2) umu Test

The umu test can be performed using a method known to those skilled in the art, for example, the method described in Mutation Research, 253 (1991) 215-222.

As the results of each of the above tests, it is clear that the compound of formula (I) has a PDE4B inhibitory activity and is effective as an active ingredient of a therapeutic or preventive pharmaceutical composition for schizophrenia, Alzheimer's disease, dementia, depression and the like.

A pharmaceutical composition containing one or two or more kinds of the compound of formula (I) or pharmaceutically acceptable salts thereof as an active ingredient can be prepared by a normally used method using an excipient for drugs, a carrier for drugs, or the like normally used in the art.

Administration may take the form of any of oral administration using tablets, pills, capsules, granules, powders, liquids, or the like; intra-articular, intravenous, or intramuscular injections, or the like; parenteral administration using suppositories, eye drops, eye ointment, transdermal solution, ointment, transdermal adhesive patches, transmucosal solutions, transmucosal adhesive patches, inhalation agents or the like.

As the solid composition for oral administration, tablets, powders, granules and the like are used. In such a solid composition, the one or two kinds or more of active ingredients are mixed with at least one kind of inert excipient, for example, lactose, mannitol, glucose, hydroxypropyl cellulose, microcrystalline cellulose, starch, polyvinyl pyrrolidone, and/or magnesium aluminometasilicate, or the like. According to a conventional method, the composition may contain inert additives, for example, lubricants such as magnesium stearate, disintegrating agents such as carboxymethyl starch sodium, stabilizing agents, and solubilizing agents. According to necessity, the tablets or pills may be coated with a sugar coating, or a film of a stomach-soluble or enteric-coated substance.

The liquid composition for oral administration includes pharmaceutically acceptable emulsions, solution agents, suspending agents, syrups, elixirs or the like, and includes commonly used inert diluents, for example, purified water or ethanol. Other than inert diluents, these liquid compositions may also contain auxiliary agents such as solubilizers, wetting agents, and suspending agents; sweetening agents, flavors, aromatics, and preservatives.

The injections for parenteral administration contain sterile aqueous or non-aqueous solution agents, suspensions, or emulsions. The aqueous vehicles include, for example, distilled water for injection or physiological saline. As the non-aqueous vehicles, for example, there are vegetable oils such as propylene glycol, polyethylene glycol, or olive oil, alcohols such as ethanol, or polysorbate 80 (Pharmacopeia name) or the like. Such compositions may further include isotonic agents, preservatives, wetting agents, emulsifiers, dispersing agents, stabilizing agents, or solubilizing agents. For example, these are sterilized by filtration through a bacteria retaining filter, blending with a germicide, or irradiation. In addition, they can also be manufactured as sterile solid compositions and used after being dissolved or suspended in sterile water or a sterile vehicle for injection before use.

Medicine for external use include ointments, plasters, creams, jellies, cataplasm, sprays, lotions, eye drops, eye ointment, and the like. Commonly used ointment bases, lotion bases, aqueous or non-aqueous solutions, suspensions, emulsions and the like may be contained. For example, examples of an ointment or lotion base include polyethylene glycol, propylene glycol, white petrolatum, white beeswax, polyoxyethylene hydrogenated castor oil, glyceryl monostearate, stearyl alcohol, cetyl alcohol, lauroyl macrogol, sorbitan sesquioleate, and the like.

Transmucosal agents such as inhalants or transnasal agents can be prepared according to a conventionally known method using solids, liquids or semi-solids. For example, known excipients, or, further, pH adjusting agents, preservatives, surfactants, lubricants, stabilizers, thickening agents, and the like may be suitably added. For the administration, it is possible to use the device for inhalation or insufflation as appropriate. For example, it is possible to perform administration using a known device or sprayer such as a metered dose inhalation device with the compound alone or as powder of a prescribed mixture, or as a solution or suspension in combination with a pharmaceutically acceptable carrier. Dry powder inhalers and the like may be ones for single or multiple administrations and can use dry powder or powder-containing capsules. Alternatively, a suitable ejection agent, for example, may be in the form of a pressurized aerosol spray using a suitable gas such as chlorofluoroalkane, hydrofluoroalkane, or carbon dioxide.

In the case of normal oral administration, the daily administration dose is approximately about 0.0001 to 100 mg/kg of body weight, and administration may be performed once or divided into two to four times. When administered intravenously, an appropriate daily administration dose is about 0.0001 to 10 mg/kg of body weight, and administration may be performed once per day or divided into a plurality of times. Further, in the case of inhalation, about 0.0001 to 1 mg/kg of body weight is administered once per day or divided into a plurality of times. The administration dose is appropriately determined depending on individual cases after taking into consideration the symptoms, age, gender, and the like.

The compound of formula (I) can be used in combination with a variety of therapeutic agents or preventive agents for diseases as long as the exhibiting of the effectiveness of the compound of formula (I) described above is considered. The combined use may be simultaneous administration, separate and sequential administration, or administration at desired time intervals. The simultaneous administration formulation may be separately formulated even with a combined drug.

EXAMPLES

Below, further detailed description will be given of the preparation method of the compound of formula (I) based on Examples. Here, the present invention is not limited to the compounds described in the following Examples. In addition, the Preparation Examples show the starting compound preparation method. In addition, the preparation method of the compound of formula (I) is not limited to only the preparation method of the specific Examples shown below, and the compounds of formula (I) can be prepared by a combination of these preparation methods or by methods obvious to those skilled in the art.

In addition, in the Examples, Preparation Examples and in the following tables, the following abbreviations may be used.

PEx: Preparation Example number, Ex: Example number, Str: Structural formula (In the structural formula, in a case where there is description of HCl for example, this means that the compound is a hydrochloride salt, and, in a case where there is description of 2HCl, this means that the compound is dihydrochroride), rel: Relative configuration (in a case where there is description of rel under the PEx or Ex number, this means that the three-dimensional notation of the structural formula described in the Str column shows the relative configuration.), Syn: Preparation method (in a case where there is only a number, the prepared Example is shown in the same manner, and, in a case where there is a P before the number, the prepared Preparation Example number is shown in the same manner, respectively.), Dat: Physical and chemical data, NMR1: δ (ppm) in 1H NMR in DMSO-$d_6$, NMR2: δ (ppm) in $^1$H NMR in CDCl$_3$, CI: CI-MS, EI: EI-MS, ESI+: ESI-MS (cation), A/E+: simultaneous measurement (cation) of APCI and ESI, FAB+: FAB-MS (cation), TFA: trifluoroacetic acid, THF: tetrahydrofuran, DMF: N,N-dimethylformamide, DMSO: dimethyl sulfoxide, MeOH: methanol, EtOH: ethanol, Et2O: diethyl ether, EtOAc: ethyl acetate, NMP: N-methylpyrrolidone, DEAD: diethyl azodicarboxylate, DIPEA: diisopropylethylamine, mCPBA: m-chloroperbenzoic acid, LAH: lithium aluminum hydride.

Preparation Example 1

55% sodium hydride (1.30 g) was added under ice-cooling to a THF (87 ml) solution of tert-butyl 4-(hydroxymethyl)-3,6-dihydropyridine-1(2H)-carboxylate (5.77 g), and this suspension was stirred at room temperature for 30 minutes. After ice-cooling again, benzyl bromide (5.32 g) and tetrabutylammonium iodide (1.00 g) were added thereto and stirring was performed at room temperature for 3 hours. After adding a saturated ammonium chloride aqueous solution, extraction was performed with EtOAc. A residue which was obtained by washing with saturated brine, drying over anhydrous magnesium sulfate, and concentration was purified by silica gel column chromatography (EtOAc/hexane) to obtain tert-butyl 4-[(benzyloxy)methyl]-3,6-dihydropyridine-1(2H)-carboxylate (6.16 g).

Preparation Example 2 mCPBA (purity 75%: 5.57 g) was added to a chloroform (67 ml) solution of tert-butyl 4-[(benzyloxy)methyl]-3,6-dihydropyridine-1(2H)-carboxylate (6.68 g), and stirring was performed at room temperature for 1 hour. A 1M sodium hydroxide aqueous solution was added, and extraction was performed with chloroform. The organic layer was washed again with a 1M sodium hydroxide aqueous solution, washed with saturated brine, dried over anhydrous magnesium sulfate, and concentrated. The resulting crude tert-butyl 6-[(benzyloxy)methyl]-7-oxa-3-azabicyclo[4.1.0]heptane-3-carboxylate (7.03 g) was used in the following reaction without purification.

Preparation Example 3

An Et2O (25 ml) solution of tert-butyl 6-[(benzyloxy)methyl]-7-oxa-3-azabicyclo[4.1.0]heptane-3-carboxylate (3.37 g) was added dropwise under ice-cooling to an suspension of LAH (520 mg) in Et2O (75 ml), and was stirred at room temperature for 1 hour, Under ice-cooling, a saturated ammonia aqueous solution (1 ml) was added. After dilution with THF, stirring was performed at room temperature for 2 hours. After drying over anhydrous magnesium sulfate, Celite filtering was performed. The residue obtained by concentration was purified by silica gel column chromatography (EtOAc/hexane) to obtain tert-butyl 4-[(benzyloxy)methyl]-4-hydroxypiperidine-1-carboxylate (2.59 g).

Preparation Example 4

55% sodium hydride (4.06 g) was added under ice-cooling to a DMF (100 ml) solution of tert-butyl 4-[(benzyloxy)methyl]-4-hydroxypiperidine-1-carboxylate (9.96 g), and stirring was performed at 50° C. for 40 minutes. Under ice-cooling, methyl iodide (22.0 g) was added dropwise, and the mixture was stirred at room temperature for 4 hours. After adding a saturated ammonium chloride aqueous solution and purified water to the reaction liquid, extraction was performed with EtOAc. The organic layer was washed with saturated brine and dried over anhydrous magnesium sulfate, and concentrated under reduced pressure. The resulting residue was purified by silica gel column chromatography (EtOAc/hexane) to obtain tert-butyl 4-[(benzyloxy)methyl]-4-methoxypiperidine-1-carboxylate (9.27 g).

Preparation Example 6

20% palladium hydroxide on carbon (270 mg) was suspended in a MeOH (81 ml) solution of tert-butyl 4-[(benzyloxy)methyl]-4-methoxypiperidine-1-carboxylate (2.7 g), and stirred under a flow of hydrogen gas at room temperature for 4 hours. After filtering using Celite, the filtrate was concentrated, and the residue was purified by silica gel column chromatography (EtOAc) to obtain tert-butyl 4-(hydroxymethyl)-4-methoxypiperidine-1-carboxylate (1.55 g).

Preparation Example 7

4 M hydrochloric acid/dioxane solution (15 ml) was added to a solution of tert-butyl 4-cyano-4-(hydroxymethyl)piperidine-1-carboxylate (886 mg) in dioxane (5 ml), and stirring was performed for one hour at room temperature. The reaction mixture was concentrated under reduced pressure, and 4-(hydroxymethyl)piperidine-4-carbonitrile hydrochloride (663 mg) was obtained.

Preparation Example 10

4M hydrochloric acid/dioxane solution (11.4 ml) was added to tert-butyl rel-(3R,4S)-3-fluoro-4-(hydroxymethyl)-4-methoxypiperidine-1-carboxylate (800 mg) and stirring was performed at room temperature for 1 hour. Concentration under reduced pressure gave rel-[(3R,4S)-3-fluoro-4-methoxypiperidin-4-yl]methanol hydrochloride (606 mg).

Preparation Example 12

55% sodium hydride (6.02 g) was added under ice-cooling to a DMSO (250 mL) suspension of trimethylsulfoxonium iodide (33.1 g), and stirring was performed at room temperature for 1 hour. A DMSO (125 ml) solution of tert-butyl 4-oxopiperidine-1-carboxylate (25.0 g) was added, and heated and stirred at 60° C. for 1 hour. Purified water was added to the mixture, and extraction was performed with EtOAc. The organic layer was dried over anhydrous sodium sulfate and concentrated under reduced pressure. The residue was purified by silica gel column chromatography (EtOAc/hexane) to obtain tert-butyl 1-oxa-6-azaspiro[2.5]octane-6-carboxylate (21.5 g), Preparation Example 13

55% sodium hydride (7.32 g) was added under ice-cooling to a DMF (130 mL) solution of benzyl alcohol (17.62 g), and stirring was performed at room temperature for 40 minutes. Under ice-cooling again, a DMF (75 ml) solution of tert-butyl 1-oxa-6-azaspiro[2.5]octane-6-carboxylate (20.4 g) was added dropwise, and stirring was performed at room temperature for 4 hours. A saturated ammonium chloride aqueous solution and purified water were added, extraction was performed with EtOAc. And the organic layer was washed with purified water again, washed with saturated brine, dried over anhydrous magnesium sulfate, and concentrated under reduced pressure. The resulting residue was purified by silica gel column chromatography (EtOAc/hexane) to obtain tert-butyl 4-[(benzyloxy)methyl]-4-hydroxypiperidine-1-carboxylate (10.01 g).

Preparation Example 14

Benzyl chloride (1.90 g) and sodium carbonate (1.59 g) were added to a DMF (70 ml) suspension of 4-methylpiperidine-4-carboxamide hydrochloride (2.24 g), and stirring was performed at room temperature for 16 hours. After adding water to the reaction liquid, extraction was performed with EtOAc. The organic layer was concentrated under reduced pressure and the residue was purified by silica gel column chromatography (MeOH/chloroform) to obtain 1-benzyl-4-methylpiperidine-4-carboxamide (2.85 g).

Preparation Example 15

A THF (30 ml) solution of 1-benzyl-4-methylpiperidine-4-carboxamide (2.85 g) was added dropwise over 30 minutes to an ice-cooled suspension of LAH (1.40 g) in THF (50 ml) under a flow of argon gas. After beating the reaction to room temperature and stirring for 1 hour, heating and stirring were performed at 50° C. for 1 hour. The reaction liquid was ice-cooled, and a 90% THF aqueous solution (14 mL), a 15% sodium hydroxide aqueous solution (1.4 mL), and water (4.2 mL) were sequentially added. After stirring the reaction liquid at room temperature for 1 hour, Celite filtration was performed, and the filtrate was concentrated under reduced pressure to obtain 1-(1-benzyl-4-methylpiperidin-4-yl) methanamine (2.68 g).

Preparation Example 16

Di-tert-butyl dicarbonate (2.81 g) was added to a THF (100 ml) solution of 1-(1-benzyl-4-methylpiperidin-4-yl)methanamine (2.68 g), and stirring was performed at room temperature for 16 hours. The reaction liquid was concentrated under reduced pressure and the residue was purified by silica gel column chromatography (EtOAc/hexane) to obtain tert-butyl [(1-benzyl-4-methylpiperidin-4-yl)methyl]carbamate (2.57 g).

Preparation Example 17

20% palladium hydroxide on carbon (283 mg) was added to an EtOH (100 ml) solution of tert-butyl[(1-benzyl-4-methylpiperidin-4-yl)methyl]carbamate (2.57 g), and stirring was performed at 70° C. under a hydrogen atmosphere of medium pressure of 3 kgf/cm$^2$ for 16 hours. After argon purge the reaction liquid was filtered through Celite and concentrated under reduced pressure to obtain tert-butyl[(4-methylpiperidin-4-yl)methyl]carbamate (1.90 g).

Preparation Example 19

Under an argon atmosphere, after diethyl zinc (1.0M hexane solution: 27.0 ml) was added to dichloromethane (40 ml) with ice cooling, a TFA (2 ml)/dichloromethane (10 ml) solution was added dropwise, and stirring was performed under ice cooling for 40 minutes. Then, after a diiodomethane (7.24 g)/dichloromethane (10 ml) solution was added dropwise and further stirring was performed at the same temperature for 40 minutes. Tert-butyl 4-[(benzyloxy)methyl]-3,6-dihydropyridine-1(2H)-carboxylate (3.28 g)/dichloromethane (30 ml) solution was added dropwise, and stirring was performed at room temperature for 15 hours. After adding triethylamine under ice cooling and adjusting pH to 7 to 8, di-tert-butyl dicarbonate (2.83 g) was added, and stirring was performed at room temperature for 5 hours. A saturated ammonium chloride aqueous solution was added, extraction was performed with chloroform, followed by washing with saturated brine and drying over anhydrous magnesium sulfate. The residue obtained by concentration under reduced pressure was purified by silica gel column chromatography (EtOAc/hexane) to obtain tert-butyl 6-[(benzyloxy)methyl]-3-azabicyclo[4.1.0] heptane-3-carboxylate (2.22 g).

Preparation Example 20

Potassium bifluoride (1.22 g) and tetrabutylammonium dihydrogentrifluoride (472 mg) were added to tert-butyl 6-[(benzyloxy) methyl]-7-oxa-3-azabicyclo[4.1.0]heptane-3-carboxylate (2.50 g), followed by heating and stirring at 120° C. for 2 days. The reaction was diluted with chloroform and filtered through Celite. The residue obtained by concentration of the solvent under reduced pressure was purified by silica gel column chromatography (EtOAc/hexane) to obtain tert-butyl 4-[(benzyloxy)methyl]-3-fluoro-4-hydroxypiperidine-1-carboxylate (1.76 g).

Preparation Example 21

20% palladium hydroxide on carbon powder (102 mg) was suspended in a MeOH (29 ml) solution of tert-butyl rel-(3R, 4S)-4-[(benzyloxy)methyl]-3-fluoro-4-methoxypiperidine-1-carboxylate (971 mg), and stirring was performed at room temperature under a flow of hydrogen gas for 4 hours. After filtration through Celite, the filtrate was concentrated to obtain tert-butyl rel-(3R,4S)-3-fluoro-4-(hydroxymethyl)-4-methoxypiperidine-1-carboxylate (800 mg).

Preparation Example 22

Under ice-cooling, 1M sodium hydroxide aqueous solution (6.0 ml) and benzyl chloroformate (1.03 g) were sequentially added to a dioxane (50 ml) suspension of tert-butyl 4-cyano-4-({[(4-methylphenyl)sulfonyl]oxy}methyl)piperidine-1-carboxylate (2.15 g), and stirring was performed at room temperature for 16 hours. The reaction liquid was concentrated under reduced pressure, and extracted with EtOAc. The organic layer was concentrated under reduced pressure and the residue was purified by silica gel column chromatography (EtOAc/hexane) to obtain 2-benzyl 7-tert-butyl 2,7-diazaspiro[3.5]nonane-2,7-dicarboxylate (1.68 g).

Preparation Example 23

A mixture of 1H-benzimidazol-2-ylacetonitrile (13 g), methyl 4-oxotetrahydro-2H-thiopyran-3-carboxylate (15.3 g), and ammonium acetate (33 g) was heated and stirred at 140° C. for 1 hour. The reaction mixture was cooled to room temperature, water and acetonitrile were added, and the resulting precipitate was collected by filtration and dried under reduced pressure to obtain 12-oxo-3,4,6,12-tetrahydro-1H-thiopyrano[4',3':4,5]pyrido[1,2-a]benzimidazole-5-carbonitrile (16 g).

Preparation Example 27

Phosphorus oxychloride (50 ml) was added to 12-oxo-3,4,6,12-tetrahydro-1H-thiopyrano[4',3':4,5]pyrido[1,2-a]benzimidazole-5-carbonitrile (16 g), followed by heating under reflux for 3 hours. The reaction liquid was concentrated under reduced pressure and the residue was poured into ice-water. The precipitate was collected by filtration and washed with water to obtain 12-chloro-3,4-dihydro-1H-thiopyrano[4',3': 4,5]pyrido[1,2-a]benzimidazole-5-carbonitrile (18 g).

Preparation Example 32

Sulfuric acid (15 ml) and purified water (2 ml) were added to 11-chloro-2,3-dihydro-1H-cyclopenta[4,5]pyrido[1,2-a] benzimidazole-4-carbonitrile (4.00 g), and stirring was performed at 50° C. for 1 day. The reaction solution was cooled and neutralized by adding 28% ammonia aqueous solution thereto while cooling with ice-water. The precipitated solid was collected by filtration and washed with water to obtain 11-chloro-2,3-dihydro-1H-cyclopenta[4,5]pyrido[1,2-a] benzimidazole-4-carboxamide (4.48 g).

Preparation Example 38

A mixture of 11-chloro-2,3-dihydro-1H-cyclopenta[4,5] pyrido[1,2-a]benzimidazole-4-carbonitrile (1.0 g) and polyphosphoric acid (5 ml) was stirred at 100° C. for 30 minutes and then at 130° C. for 1 hour. The reaction mixture was poured into ice water, the pH was adjusted to 9 using 28% aqueous ammonia, and the precipitated solid was collected by filtration. The resulting solid was washed with 2-propanol and Et2O and dried under reduced pressure to obtain 11-chloro-2,3-dihydro-1H-cyclopenta[4,5]pyrido[1,2-a]benzimidazole-4-carboxamide (1.03 g).

Preparation Example 39

An aqueous solution (30 ml) of potassium cyanide (15 g) was ice-cooled, then, an EtOH (140 ml) solution of 2-(chloromethyl)-4,5,6,7-tetrahydro-1H-benzimidazole hydrochloride (12.0 g) was added, and stirring was performed at room temperature for 1 hour and then at 50° C. for 1, hour. A saturated aqueous sodium hydrogen carbonate solution was added to the reaction liquid, followed by concentration under reduced pressure and extraction with chloroform. The organic layer was concentrated under reduced pressure and the residue was purified by silica gel column chromatography (28% aqueous ammonia/methanol/chloroform) to obtain 4,5,6,7-tetrahydro-1H-benzimidazol-2-yl acetonitrile (8.6 g).

Preparation Example 40

A mixture of 4,5,6,7-tetrahydro-1H-benzimidazol-2-yl acetonitrile (8.5 g), methyl 2-oxocyclopentanecarboxylate (7.5 g) and ammonium acetate (20.3 g) was stirred at 140° C. for 2 hours. The reaction mixture was cooled to room temperature, water was added, and extraction was performed with chloroform. The organic layer was washed with a saturated brine, dried over anhydrous sodium sulfate, and concentrated reduced pressure. The residue was solidified using hexane/EtOAc to obtain 11-hydroxy-2,3,6,7,8,9-hexahydro-1H-cyclopenta[4,5]pyrido[1,2-a]benzimidazole-4-carbonitrile (2.56 g).

In the same manner as the methods of the above-described Preparation Examples, each Preparation Example compound was manufactured using the respective corresponding starting materials. The structures of the Preparation Example compounds, the preparation methods and the physical and chemical data are shown in the following tables.

TABLE 2

| PEx | Str |
|---|---|
| 1 | ![structure] |
| 2 | ![structure] |
| 3 | ![structure] |
| 4 | ![structure] |
| 5 | ![structure] |
| 6 | ![structure] |
| 7 | ![structure] |
| 8 | ![structure] |
| 9 | ![structure] |
| 10 rel | ![structure] |
| 11 | ![structure] |
| 12 | ![structure] |
| 13 | ![structure] |

TABLE 2-continued

| PEx | Str |
|---|---|
| 14 | 1-benzyl-4-methylpiperidine-4-carboxamide |
| 15 | (1-benzyl-4-methylpiperidin-4-yl)methanamine |
| 16 | tert-butyl ((1-benzyl-4-methylpiperidin-4-yl)methyl)carbamate |

TABLE 3

| PEx | Str |
|---|---|
| 17 | tert-butyl ((4-methylpiperidin-4-yl)methyl)carbamate |
| 18 | tert-butyl 1-(hydroxymethyl)-3-azabicyclo[3.1.0]hexane-3-carboxylate |
| 19 | tert-butyl 1-((benzyloxy)methyl)-3-azabicyclo[3.1.0]hexane-3-carboxylate |
| 20 | tert-butyl 4-((benzyloxy)methyl)-3-fluoro-4-hydroxypiperidine-1-carboxylate |
| 21 rel | tert-butyl 4-fluoro-4-(hydroxymethyl)-3-methoxypiperidine-1-carboxylate |
| 22 | 2-benzyl 7-tert-butyl 2,7-diazaspiro[3.5]nonane-2,7-dicarboxylate |
| 23 | thiopyrano-benzimidazole carbonitrile |
| 24 | bicyclic carbonitrile |
| 25 | dimethyl cyclopenta-benzimidazole carbonitrile |
| 26 | dimethyl tetrahydro-benzimidazole carbonitrile |
| 27 | chloro thiopyrano-benzimidazole carbonitrile |

TABLE 3-continued

| PEx | Str |
|---|---|
| 28 | (structure) |
| 29 | (structure) |
| 30 | (structure) |

TABLE 4

| PEx | Str |
|---|---|
| 31 | (structure) |
| 32 | (structure) |
| 33 | (structure) |
| 34 | (structure) |
| 35 | (structure) |
| 36 | (structure) |
| 37 | (structure) |
| 38 | (structure) |
| 39 | (structure) |
| 40 | (structure) |

TABLE 5

| PEx | Syn | Dat |
|---|---|---|
| 1 | P1 | ESI+: 326 (M + Na) |
| 2 | P2 | EI: 263 (M − Bu) |
| 3 | P3 | CI: 322 |
| 4 | P4 | EI: 335 |
| 5 | P4 | ESI+: 376 (M + Na) |
| 6 | P6 | EI: 245 |
| 7 | P7 | ESI+: 141 |
| 8 | P7 | FAB+: 146 |
| 9 | P7 | ESI+: 128 |

TABLE 5-continued

| PEx | Syn | Dat |
|---|---|---|
| 10 | P10 | NMR1: 1.55 (1H, tt), 1.86 (1H, d), 2.70-3.62 (6H, m), 3.21 (3H, s), 4.66-5.06 (2H, m), 8.71 (1H, brs), 9.74 (1H, brs) |
| 11 | P10 | ESI+: 261 |
| 12 | P12 | EI: 213 |
| 13 | P13 | ESI+: 222 (M − Boc) |
| 14 | P14 | ESI+: 233 |
| 15 | P15 | |
| 16 | P16 | ESI+: 319 |
| 17 | P17 | CI: 229 |
| 18 | P17 | NMR2: 0.39 (1H, t), 0.60 (1H, dd), 0.93-1.00 (1H, m), 1.45 (9H, s), 1.49 (1H, s), 1.81 (1H, ddd),1.95 (1H, dt), 3.08 (1H, dd d), 3.35 (1H, dt), 3.38-3.44 (2H, m), 3.50-3.56 (1H, m), 3.72-3.77 (1H, m) |
| 19 | P19 | ESI+: 340 (M + Na) |
| 20 | P20 | CI: 340 |
| 21 | P21 | |
| 22 | P22 | FAB+: 361 |
| 23 | P23 | ESI+: 282 |
| 24 | P23 | FAB+: 276 |
| 25 | P23 | FAB+: 278 |
| 26 | P23 | FAB+: 292 |
| 27 | P27 | ESI+: 300 |
| 28 | P27 | FAB+: 294 |
| 29 | P27 | FAB+: 296 |
| 30 | P27 | FAB+: 310 |
| 31 | P27 | ESI+: 272 |
| 32 | P32 | ESI+: 286 |
| 33 | P32 | FAB+: 318 |
| 34 | P32 | ESI+: 290 |

TABLE 6

| PEx | Syn | Dat |
|---|---|---|
| 35 | P32 | EI: 313 |
| 36 | P32 | EI: 327 |
| 37 | P32 | ESI+: 312 |
| 38 | P38 | A/E+: 286, 288 |
| 39 | P39 | EI: 161 |
| 40 | P40 | ESI+: 254 |

Example 1

11-chloro-2,3-dihydro-1H-cyclopenta[4,5]pyrido[1,2-a]benzimidazole-4-carboxamide (800 mg) and DIPEA (1.95 ml) were added to an NMP suspension of 3-azabicyclo[4.1.0]hept-6-ylmethanol hydrochloride (1.01 g), and stirring was performed at 220° C. for 60 minutes under microwave irradiation. The reaction liquid was added to water and the precipitate was collected by filtration. The resulting solid was purified by silica gel column chromatography (MeOH/chloroform) to obtain 11-[6-(hydroxymethyl)-3-azabicyclo[4.1.0]hept-3-yl]-2,3-dihydro-1H-cyclopenta[4,5]pyrido[1,2-a]benzimidazole-4-carboxamide (788 mg).

Example 18

Tert-butyl[(4-methylpiperidin-4-yl)methyl]carbamate (343 mg), and DIPEA (348 μl) were added to an NMP (3 ml) solution of 11-chloro-2,3-dihydro-1H-cyclopenta[4,5]pyrido[1,2-a]benzimidazole-4-carboxamide (286 mg), and heating and stirring were performed at 200° C. for 60 minutes under microwave irradiation. After adding water to the reaction liquid, the resulting precipitate was collected by filtration and dried under reduced pressure. The resulting solid was suspended in chloroform, TFA was then added thereto and stirring was performed at room temperature for 1 hour. The reaction liquid was concentrated under reduced pressure and the residue was purified by silica gel column chromatography (MeOH/chloroform). The resulting crude purified matter was dissolved in chloroform, a 4 M hydrochloric acid-EtOAc solution was then added thereto and stirring was performed at room temperature for 1 hour. The solvent was concentrated under reduced pressure and the residue was solidified using EtOH/Et2O to obtain 11-[4-(aminomethyl)-4-methylpiperidin-1-yl]-2,3-dihydro-1H-cyclopenta[4,5]pyrido[1,2-a]benzimidazole-4-carboxamide dihydrochloride (177 mg).

Example 21

A mixture of 11-chloro-2,3-dihydro-1H-cyclopenta[4,5]pyrido[1,2-a]benzimidazole-4-carboxamide (410 mg), piperidine-4-carbonitrile (348 mg) and DIPEA (556 mg) in NMP (3.3 ml) solution was heated to 120° C. for 1 day. Water was added to the reaction liquid, and the precipitated solid was filtered and dried. The resulting solid was dissolved in THF/MeOH, silica gel was added thereto, and the solvent was concentrated and adsorbed to the silica gel. Purification by silica gel column chromatography (MeOH/chloroform) gave a solid (200 mg). The solid was dissolved in MeOH/THF, 4M hydrochloric acid-EtOAc (2.0 ml) was added, and after stirring, concentration was performed. The solid was dissolved in MeOH/THF, and 4M hydrochloric acid-EtOAc (2.0 ml) was added, followed by stirring and concentration. By washing with acetonitrile, 11-(4-cyanopiperidin-1-yl)-2,3-dihydro-1H-cyclopenta[4,5]pyrido[1,2-a]benzimidazole-4-carboxamide hydrochloride (138 mg) was obtained.

Example 22 rel-[(3R,4S)-3-fluoro-4-methoxypiperidin-4-yl]methanol hydrochloride (399 mg) and DIPEA (523 μl) were added to an NMP (3 ml) solution of 11-chloro-2,2-dimethyl-2,3-dihydro-1H-cyclopenta[4,5]pyrido[1,2-a]benzimidazole-4-carboxamide (314 mg), and heating and stirring were performed at 200° C. for 60 minutes under microwave irradiation. After adding water to the reaction liquid, the resulting precipitate was collected by filtration and dried under reduced pressure. The resulting solid was purified by silica gel column chromatography (MeOH/chloroform). The resulting crude purified matter was washed with chloroform-EtOAc-hexane to obtain rel-11-[(3R,4S)-3-fluoro-4-(hydroxymethyl)-4-methoxypiperidin-1-yl]-2,2-dimethyl-2,3-dihydro-1H-cyclopenta[4,5]pyrido[1,2-a]benzimidazole-4-carboxamide (169 mg).

Example 23

11-[6-(hydroxymethyl)-3-azabicyclo[4.1.0]hept-3-yl]-2,3-dihydro-1H-cyclopenta[4,5]pyrido1,2-a]benzimidazole-4-carboxamide (300 mg) was suspended in EtOH, 4M hydrochloric acid-dioxane solution (797 μl) was added thereto and stirring was performed at room temperature. After concentration, solidification was performed in EtOH (5 ml) to obtain 11-[6-(hydroxymethyl)-3-azabicyclo[4.1.0]hept-3-yl]-2,3-dihydro-1H-cyclopenta[4,5]pyrido[1,2-a]benzimidazole-4-carboxamide hydrochloride (75 mg).

Example 24

After adding triphenylphosphine (439 mg) and phthalimide (246 mg) to a THF (21 ml) suspension of 11-[6-(hydroxymethyl)-3-azabicyclo[4.1.0]hept-3-yl]-2,3-dihydro-1H-cyclopenta[4,5]pyrido[1,2-a]benzimidazole-4-carboxamide (420 mg), a toluene solution (2.2 M; 0.76 ml) of DEAD was added dropwise, and stirring was performed at room temperature for 12 hours. After concentration under reduced pressure, the resulting residue was purified by silica gel column chromatography (MeOH/chloroform) to obtain crude 11-{6-[(1,3-dioxo-1,3-dihydro-2,4-isoindol-2-yl)methyl]-3-azabicyclo[4.1.0]hept-3-yl}-2,3-dihydro-1H-cyclopenta[4,5]pyrido[1,2-a]benzimidazole-4-carboxamide (1.22 g).

Example 25

A TFA (10 ml) solution of benzyl 7-(4-carbamoyl-2,3-dihydro-1H-cyclopenta[4,5]pyrido[1,2-a]benzimidazol-1'-yl)-2,7-diazaspiro[3.5]nonane-2-carboxylate (540 mg) was heated and stirred at 60° C. for 1 hour. The solvent was concentrated under reduced pressure and the residue was purified by silica gel column chromatography (28% aqueous ammonia/MeOH/chloroform). The resulting crude purified matter was dissolved in chloroform, and a 4M hydrochloric acid-EtOAc solution was added thereto. The reaction liquid was stirred for 1 hour and concentrated under reduced pressure. The residue was solidified using EtOH/Et2O to obtain 11-(2,7-diazaspiro[3.5]non-7-yl)-2,3-dihydro-1H-cyclopenta[4,5]pyrido[1,2-a]benzimidazole-4-carboxamide dihydrochloride (209 mg).

Example 27

20% palladium hydroxide on carbon (50 mg) was added to an EtOH (10 ml)-DMF (10 ml) solution of benzyl{[1-(4-carbamoyl-2,3-dihydro-1H-cyclopenta[4,5]pyrido[1,2-a]benzimidazol-11-yl)-4-methoxypiperidin-4-yl]methyl}carbamate (262 mg), and stirring was performed under a hydrogen atmosphere at room temperature for 14 hours. The reaction liquid was filtered through Celite and concentrated under reduced pressure. The filtrate was concentrated under reduced pressure and the residue was purified by silica gel column chromatography (28% aqueous ammonia/MeOH/chloroform). The resulting crude purified matter was dissolved in chloroform, and a 4M hydrochloric acid-EtOAc solution was then added thereto. The reaction liquid was stirred for 1 hour and concentrated under reduced pressure. The residue was solidified using EtOH/Et2O to obtain 11-[4-(aminomethyl)-4-methoxypiperidin-1-yl]-2,3-dihydro-1H-cyclopenta[4,5]pyrido[1,2-a]benzimidazole-4 carboxamide dihydrochloride (63 mg).

Example 28

Crude 11-{6-[(1,3-dioxo-1,3-dihydro-2,1-isoindol-2-yl)methyl]-3-azabicyclo[4.1.0]hept-3-yl}-2,3-dihydro-1H-cyclopenta[4,5]pyrido[1,2-a]benzimidazole-4-carboxamide (564 mg) was suspended in EtOH (11 ml), hydrazine monohydrate (0.24 ml) was added thereto, followed by heating and refluxing for 2 hours. After filtration with heating, insoluble material was separated by filtration and washed with EtOH. After concentration under reduced pressure, the residue was purified by silica gel column chromatography (MeOH/chloroform), and further purification was performed by silica gel column chromatography (MeOH/chloroform) using basic silica. The resulting solid was dissolved in EtOH (3 ml) and chloroform (2 ml), a 4M hydrochloric acid-dioxane (0.5 ml) solution was added thereto, and stirring was performed at room temperature for 30 minutes. After concentration under reduced pressure, washing was performed with EtOH/Et2O (1:1) to obtain 11-[6-(aminomethyl)-3-azabicyclo[4.1.0]hept-3-yl]-2,3-dihydro-1H-cyclopenta[4,5]pyrido[1,2-a]benzimidazole-4-carboxamide dihydrochloride (65 mg).

In the same manner as the methods of the above-described examples, each example compound was manufactured using the respectively corresponding starting materials. The structures of the example compounds, the preparation methods and the physical and chemical data are shown in the following tables.

TABLE 7

| Ex | Str |
|---|---|
| 1 | |
| 2 | |
| 3 | |
| 4 | |

TABLE 7-continued
| Ex | Str |
| --- | --- |
| 5 | 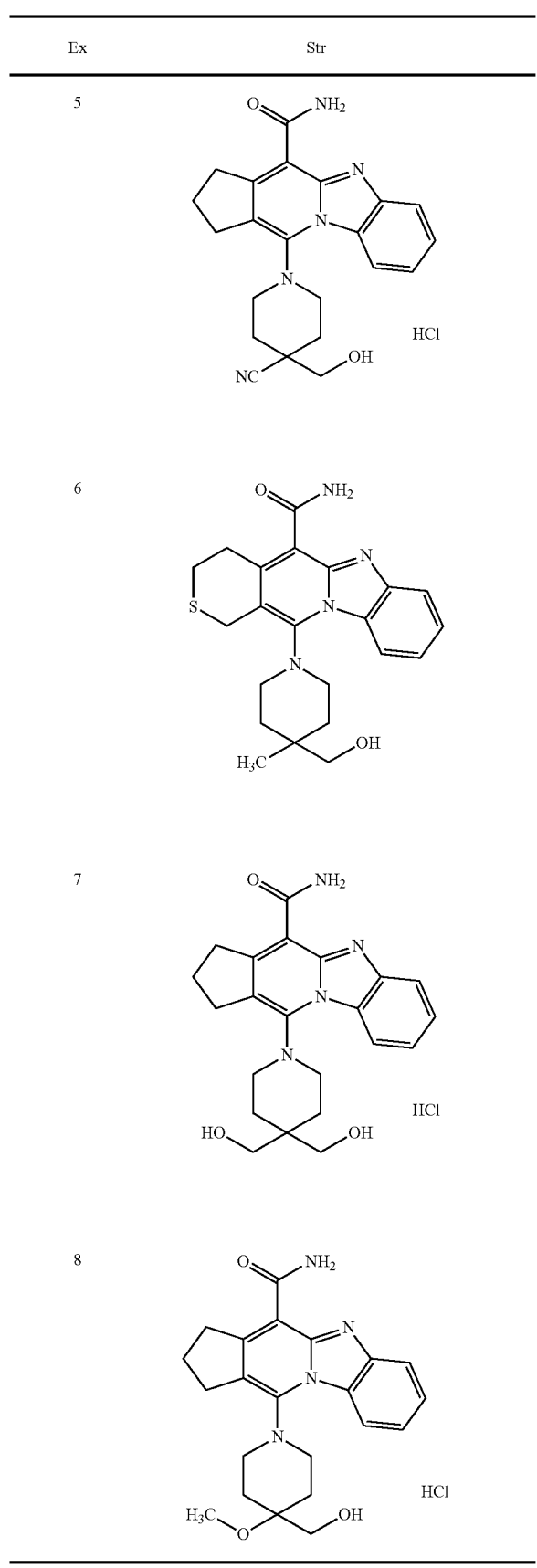 |
| 6 | |
| 7 | |
| 8 | |
TABLE 8
| Ex | Str |
| --- | --- |
| 9 | 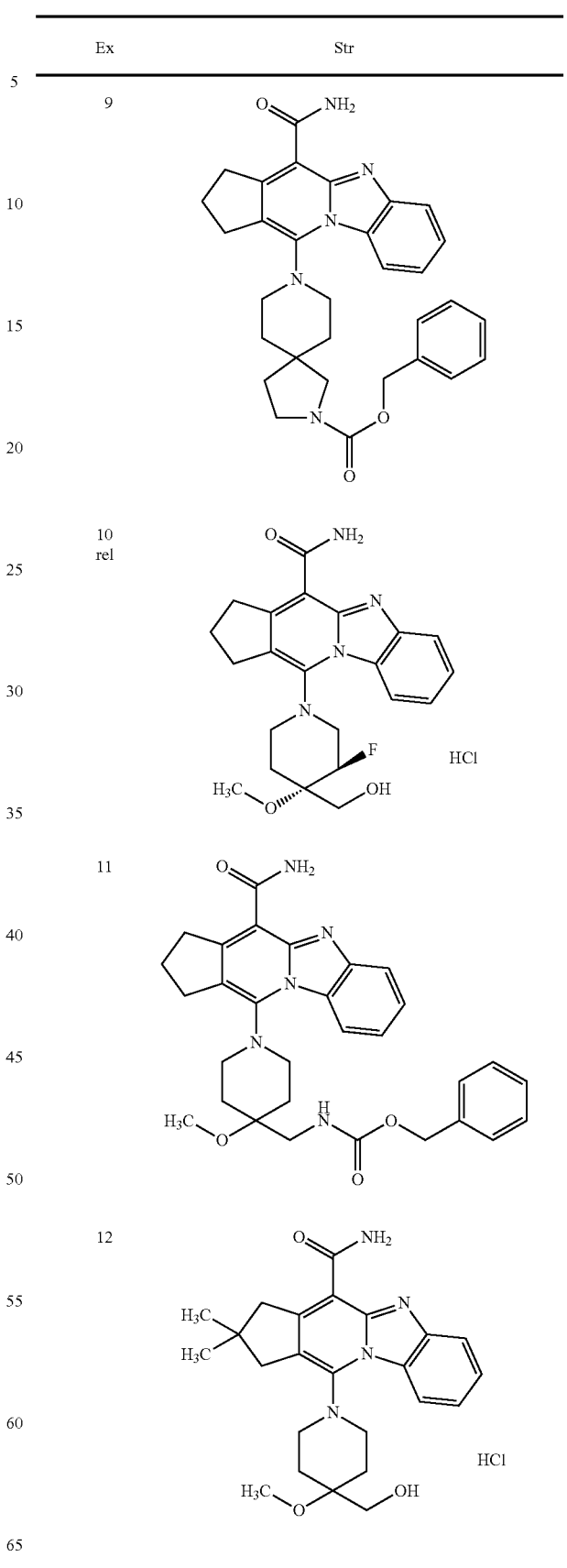 |
| 10 rel | |
| 11 | |
| 12 | |

TABLE 8-continued

| Ex | Str |
|---|---|
| 13 | (structure) HCl |
| 14 | (structure) HCl |
| 15 | (structure) HCl |
| 16 | (structure) |

TABLE 9

| Ex | Str |
|---|---|
| 17 | (structure) |
| 18 | (structure) 2HCl |
| 19 | (structure) 2HCl |
| 20 | (structure) 2HCl |

TABLE 9-continued
| Ex | Str |
|---|---|
| 21 | 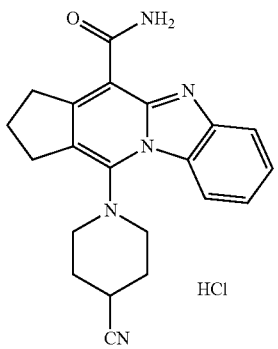 [SMILES: N#CC1CCN(c2c3c(c(C(N)=O)c4nc5ccccc5n24)CCC3)CC1 ; Cl] HCl |
| 22 rel | 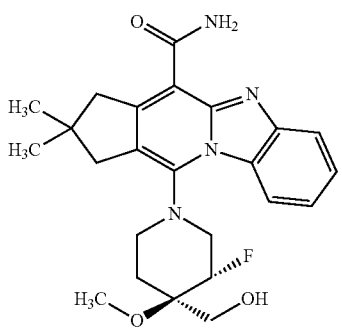 [SMILES: CO[C@@]1(CO)CCN(c2c3c(c(C(N)=O)c4nc5ccccc5n24)CC(C)(C)C3)C[C@@H]1F] |
TABLE 10
| Ex | Str |
|---|---|
| 23 | 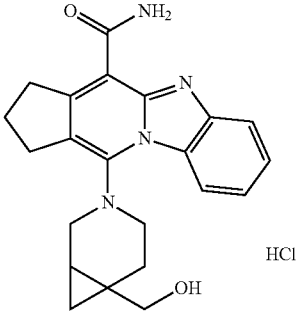 [SMILES: NC(=O)c1c2c(c(N3CCC4(CO)CC4C3)n3c1nc1ccccc13)CCC2 ; Cl] HCl |
| 24 | 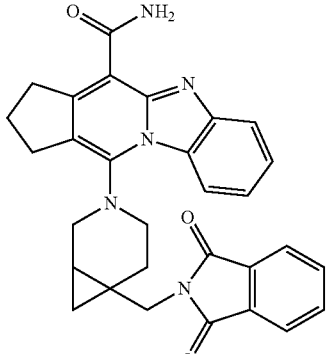 |
TABLE 10-continued
| Ex | Str |
|---|---|
| 25 | 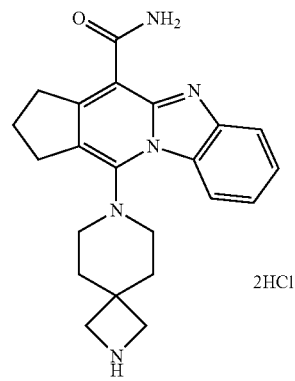 [SMILES: NC(=O)c1c2c(c(N3CCC4(CC3)CNC4)n3c1nc1ccccc13)CCC2 ; "2HCl"] 2HCl |
| 26 | 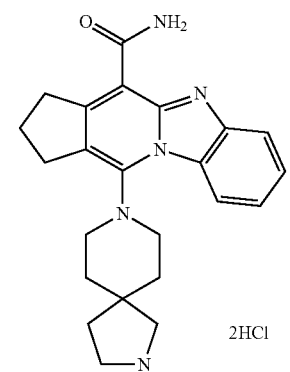 2HCl |
| 27 | 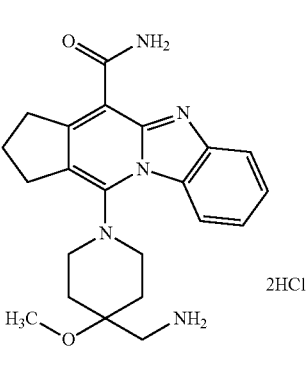 [SMILES: COC1(CN)CCN(c2c3c(c(C(N)=O)c4nc5ccccc5n24)CCC3)CC1 ; "2HCl"] 2HCl |
| 28 | 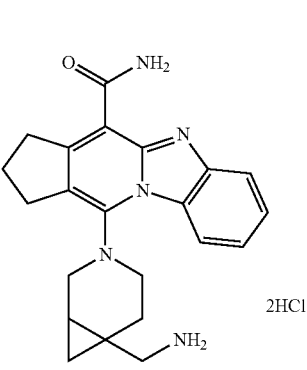 [SMILES: NCC12CCN(c3c4c(c(C(N)=O)c5nc6ccccc6n35)CCC4)CC1C2 ; "2HCl"] 2HCl |

TABLE 11

| Ex | Syn | Dat |
|---|---|---|
| 1 | 1 | FAB+: 377 |
| 2 | 1 & 23 | NMR1: 1.06 (3H, s), 1.38-1.98 (4H, m), 2.16-2.23 (2H, m), 3.13-3.51 (11H, m), 7.57-7.64 (1H, m), 7.72 (1H, t), 7.90 (1H, d), 8.21 (2H, brs), 8.79 (0.3H, d), 8.84 (0.7H, d); FAB+: 379; conformational isomer mixture |
| 3 | 1 & 23 | NMR1: 1.07 (3H, s), 1.19 (6H, s), 1.40 (2H, d), 1.72 (2H, brs), 1.94 (2H, dt), 3.00-4.38 (9H, m), 7.53-7.66 (1H, m), 7.72 (1H, t), 7.91 (1H, d), 8.23 (2H, brs), 8.80 (0.4H, d), 8.84 (0.6H, d); ESI+: 407; conformational isomer mixture |
| 4 | 1 & 23 | NMR1: 0.97-1.13 (10H, m), 1.40 (1H, d), 1.64 (2H, t), 1.69-1.81 (1H, m), 2.02 (1H, dt), 2.75 (0.6H, s), 2.77 (1.4H, s), 3.04-3.20 (5H, m), 3.31 (1H, s), 3.36-3.63 (3H, m), 7.56-7.69 (1H, m), 7.77 (1H, t), 7.86 (1H, d), 8.31 (1H, s), 8.45 (1H, s), 8.86 (0.3H, d), 9.00 (0.7H, d); ESI+: 421; conformational isomer mixture |
| 5 | 1 & 23 | NMR1: 1.91-2.12 (4H, m), 2.13-2.30 (2H, m), 3.16-3.99 (11H, m), 7.45-7.79 (2H, m), 7.90 (1H, d), 8.03-8.60 (2.1H, m), 8.73 (0.9H, d); FAB+: 390; conformational isomer mixture |
| 6 | 1 | NMR1: 1.06 (1.2H, s), 1.08 (1.8H, s), 1.30-2.10 (4H, m), 2.84-3.60 (10H, m), 3.89 (2H, s), 4.68 (0.4H, t), 4.76 (0.6H, t), 7.27-7.41 (1H, m), 7.48 (1H, t), 7.75-7.85 (2H, m), 8.39 (1H, s), 8.75 (0.4H, d), 8.82 (0.6H, d); ESI+: 411; conformational isomer mixture |
| 7 | 1 & 23 | NMR1: 1.63 (2H, d), 1.73-1.90 (2H, m), 2.10-2.28 (2H, m), 3.09-3.20 (2H, m), 3.21-3.45 (8H, m), 3.61 (2H, s), 3.70-4.30 (2H, m), 7.59 (1H, t), 7.73 (1H, t), 7.89 (1H, d), 8.06-8.50 (2H, m), 8.84 (1H, d); ESI+: 395 |
| 8 | 1 & 23 | NMR1: 1.80-1.98 (4H, m), 2.13-2.25 (2H, m), 3.04-4.06 (14H, m), 7.54-7.66 (1H, m), 7.72 (1H, t), 7.86-7.92 (1H, m), 8.06-8.50 (2H, m), 8.61 (0.28H, d), 8.81 (0.72H, d); FAB+: 395; conformational isomer mixture |
| 9 | 1 | ESI+: 524 |
| 10 | 1 & 23 | NMR1: 1.83-2.00 (2H, m), 2.10-2.35 (2H, m), 3.00-4.00 (15H, m), 7.51-7.76 (2H, m), 7.85-7.93 (1H, m), 8.06-8.60 (2.1H, m), 8.95 (0.9H, d); ESI+: 413; conformational isomer mixture |

TABLE 12

| Ex | Syn | Dat |
|---|---|---|
| 11 | 1 | NMR1: 1.80-1.96 (4H, m), 2.01-2.21 (2H, m), 2.94-3.56 (13H, m), 5.03-5.14 (2H, m), 7.23-7.45 (7H, m), 7.49 (0.9H, t), 7.59 (0.1H, td), 7.68-7.94 (2H, m), 8.56-8.72 (1H, m), 9.87 (0.1H, d), 10.09 (0.9H, d): FAB+: 528; conformational isomer mixture |
| 12 | 1 & 23 | NMR1: 1.19 (6H, s), 1.80-2.00 (4H, m), 3.03 (2H, s), 3.07-3.19 (4H, m), 3.26 (2.7H, s), 3.27 (0.3H, s), 3.30-3.41 (2H, m), 3.52 (1.8H, s), 3.69 (0.2H, s), 7.54-7.76 (2H, m), 7.72 (1H, t), 7.90 (1H, d), 8.21 (2H, brs), 8.64 (0.1H, d), 8.81 (0.9H, d); ESI+: 423; conformational isomer mixture |
| 13 | 1 & 23 | NMR1: 0.95-1.15 (6H, m), 1.59-1.70 (2H, m), 1.83-2.01 (4H, m), 2.71 (0.4H, s), 2.74 (1.6H, s), 2.99-3.14 (5H, m), 3.29 (2.4H, s), 3.32 (0.6H, s), 3.21-3.71 (4H, m), 7.51-7.78 (2H, m), 7.86 (1H, d), 8.31 (1H, s), 8.42 (0.2H, s), 8.44 (0.8H, s), 8.61 (0.2H, d), 8.92 (0.8H, d); ESI+: 437; conformational isomer mixture |
| 14 | 1 & 23 | NMR1: 1.27-1.42 (2H, m), 1.67-2.25 (8H, m), 3.06-4.10 (12H, m), 7.52-7.74 (2H, m), 7.84-7.91 (1H, m), 8.20 (1H, s), 8.50 (1H, s), 8.62 (0.1H, d), 8.80 (0.9H d); ESI+: 421; conformational isomer mixture |
| 15 | 1 & 23 | NMR1: 1.60-1.94 (8H, m), 2.06-2.22 (2H, m), 2.75 (2H, brs), 2.91 (2H, brd),, 3.00-4.00 (14H, m), 8.09 (1H, brs), 8.15 (1H, brs); ESI+: 399; conformational isomer mixture |
| 16 | 1 | NMR1: 1.83-2.00 (4H, m), 2.86-3.71 (13H, m), 3.86 (1.6H, s), 3.90 (0.4H, s), 4.74 (1H, t), 7.30-7.56 (2H, m), 7.75-7.87 (2H, m), 8.34-8.47 (1H, m), 8.58 (0.2H, d), 8.73 (0.8H, d); ESI+: 427; conformational isomer mixture |
| 17 | 1 | |
| 18 | 18 | NMR1: 1.20 (1.8H, s), 1.21 (1.2H, s), 1.50-2.26 (6H, m), 2.82-3.50 (12H, m), 7.61 (1H, t), 7.72 (1H, t), 7.88 (1H, d), 8.05-8.28 (4H, m), 8.75 (0.4H, d), 8.82 (0.6H, d); ESI+: 378; conformational isomer mixture |
| 19 | 18 | NMR1: 1.58-2.27 (7H, m), 2.82-4.30 (12H, m), 7.27-7.96 (3H, m), 8.07-8.50 (4H, m), 8.53 (0.1H, d), 8.83 (0.9H, d); ESI+: 364; conformational isomer mixture |

TABLE 13

| Ex | Syn | Dat |
|---|---|---|
| 20 | 18 | NMR1: 1.19 (6H, s), 1.21 (3H, s), 1.55-2.04 (4H, m), 2.84-2.93 (1H, m), 3.01-4.00 (11H, m), 7.59-7.66 (1H, m), 7.72 (1H, t), 7.90 (1H, d), 8.21 (2H, brs), 8.31 (2H, brs), 8.77 (0.3H, d), 8.83 (0.7H, d) ESI+: 406; conformational isomer mixture |
| 21 | 21 | NMR1: 2.02 (1H, d), 2.15-2.53 (5H, m), 3.04-3.48 (9H, m), 7.54-7.74 (2H, m), 7.89 (1H, d), 8.19 (2H, brs), 8.73 (0.4H, d), 8.82 (0.6H, d); FAB+: 360; conformational isomer mixture |
| 22 | 22 | NMR1: 1.12 (3H, s), 1.20 (3H, s), 1.80-2.00 (2H, m), 2.70-3.80 (13H, m), 4.70-4.90 (2H, m), 7.31 (1H, t), 7.48 (1H, t), 7.80 (2H, brs), 8.81 (1H, d), 10.09 (1H, brs); ESI+: 441; conformational isomer mixture |
| 23 | 23 | NMR1: 0.70-0.92 (2H, m), 1.26-1.38 (1H, m), 1.60-2.34 (4H, m), 3.02-4.04 (11H, m), 7.48-7.58 (1H, m), 7.67-7.76 (1H, m), 7.88 (1H, t), 8.00-8.52 (2.25H, m), 8.85 (0.75H, d); FAB+: 377; conformational isomer mixture |
| 24 | 24 | ESI+: 506 |
| 25 | 25 | NMR1: 2.05-2.25 (4H, m), 3.10-4.00 (15H, m), 7.55 (1H, t), 7.71 (1H, t), 7.88 (1H, d), 8.10-8.70 (2H, m), 8.76 (1H, d), 9.38 (2H, brs); ESI+: 376 |
| 26 | 25 | NMR1: 1.71-2.28 (8H, m), 3.12 (1H, t), 3.20-4.00 (12H, m), 7.61 (1H, t), 7.73 (1H, t), 7.90 (1H, d), 8.21 (1H, brs), 8.34 (1H, brs), 8.82 (1H, t), 9.64-9.86 (2H, m); ESI+: 390; conformational isomer mixture |
| 27 | 27 | NMR1: 1.93-2.25 (6H, m), 3.09-3.46 (15H, m), 7.55 (1H, t), 7.71 (1H, t), 7.88 (1H, d), 8.05 (3H, brs), 8.16 (1H, brs), 8.59 (0.1H, d), 8.81 (0.9H, d); ESI+: 394; conformational isomer mixture |
| 28 | 28 | NMR1: 0.90-1.06 (3H, m), 1.41-1.59 (1H, m), 1.73-229 (3H, m), 2.62-2.76 (1H, m), 2.98-4.10 (1H, m), 7.49-7.77 (2H, m), 7.85-7.93 (1H, m), 8.10-8.57 (5H, m); ESI+: 376; conformational isomer mixture |

In the same manner as the Preparation Examples and the Examples described above, the compounds shown in the following table were prepared using the respective corresponding starting materials.

TABLE 14

| No. | Str |
|---|---|
| A1 | [structure: cyclopenta-fused pyrido-benzimidazole with CN group and piperazine-N-CHO substituent; HCl salt] |
| A2 | [structure: cyclopenta-fused pyrido-benzimidazole with CN group and 1,4-oxazepane substituent; HCl salt] |
| A3 | [structure: methyl- and benzyl-substituted pyrido-benzimidazole with CN group and 1,4-diazepan-5-one substituent; HCl salt] |
| A4 | [structure: methyl- and benzyl-substituted pyrido-benzimidazole with CN group and 4-methyl-1,4-diazepane substituent; 2HCl salt] |

TABLE 14-continued
| No. | Str |
|-----|-----|
| A5 | 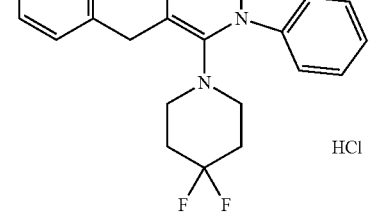 HCl |
| A6 | HCl |
| A7 | |
| A8 | |
TABLE 15
| No. | Str |
|-----|-----|
| A9 | |
| A10 | |
| A11 | |
| A12 | |
| A13 | 2HCl |

TABLE 15-continued

| No. | Str |
|---|---|
| A14 | (structure) |
| A15 | (structure) 2HCl |
| A16 | (structure) 2HCl |
| A17 | (structure) |
| A18 | (structure) 2HCl |

TABLE 16

| No. | Str |
|---|---|
| A19 | (structure) HCl |
| A20 | (structure) HCl |
| A21 | (structure) 2HCl |
| A22 | (structure) 2HCl |

TABLE 16-continued
| No. | Str |
|---|---|
| A23 | 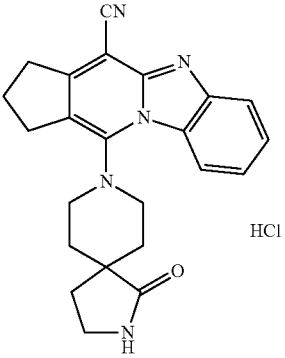 [SMILES: N#Cc1c2c(c(N3CCC4(CCNC4=O)CC3)n3c1nc1ccccc13)CCC2 ; Cl] HCl |
| A24 | 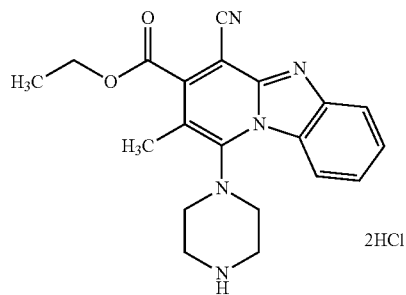 [SMILES: CCOC(=O)c1c(C)c(N2CCNCC2)n2c(nc3ccccc32)c1C#N ; "2HCl"] 2HCl |
| A25 | 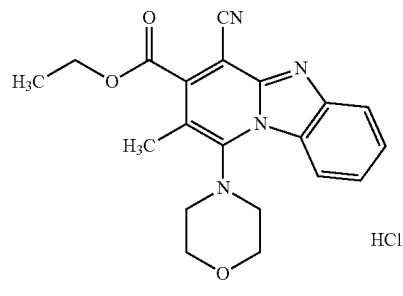 [SMILES: CCOC(=O)c1c(C)c(N2CCOCC2)n2c(nc3ccccc32)c1C#N ; Cl] HCl |
| A26 | 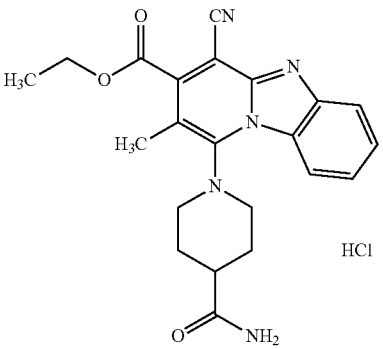 [SMILES: CCOC(=O)c1c(C)c(N2CCC(C(N)=O)CC2)n2c(nc3ccccc32)c1C#N ; Cl] HCl |
TABLE 17
| No. | Str |
|---|---|
| A27 | 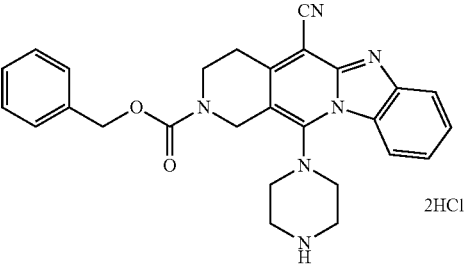 [SMILES: N#Cc1c2c(c(N3CCNCC3)n3c1nc1ccccc13)CN(C(=O)OCc1ccccc1)CC2 ; "2HCl"] 2HCl |
| A28 | 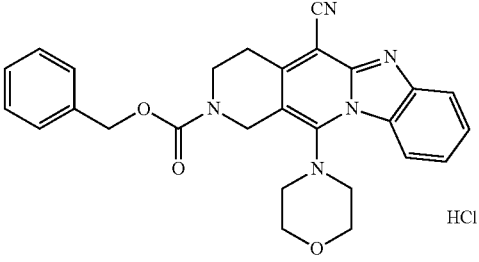 [SMILES: N#Cc1c2c(c(N3CCOCC3)n3c1nc1ccccc13)CN(C(=O)OCc1ccccc1)CC2 ; Cl] HCl |
| A29 | 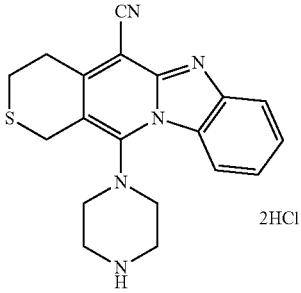 [SMILES: N#Cc1c2c(c(N3CCNCC3)n3c1nc1ccccc13)CSCC2 ; "2HCl"] 2HCl |
| A30 | 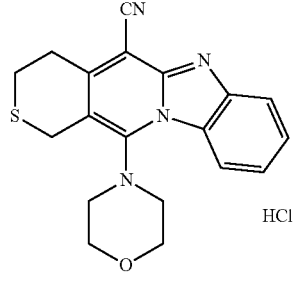 [SMILES: N#Cc1c2c(c(N3CCOCC3)n3c1nc1ccccc13)CSCC2 ; Cl] HCl |
| A31 | 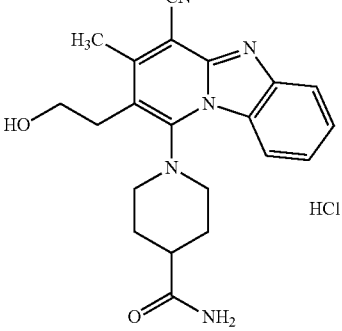 HCl |

TABLE 17-continued
| No. | Str |
|---|---|
| A32 | 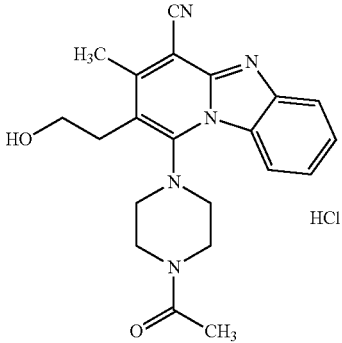 [SMILES: CC(=O)N1CCN(c2c(CCO)c(C)c(C#N)c3nc4ccccc4n23)CC1 ; Cl] HCl |
| A33 | 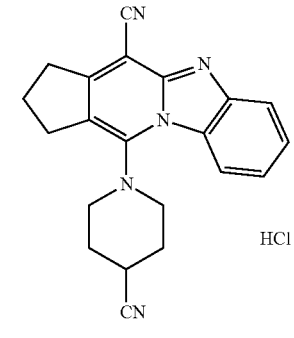 [SMILES: N#Cc1c2c(c(N3CCC(C#N)CC3)n3c1nc1ccccc13)CCC2 ; Cl] HCl |
| A34 | 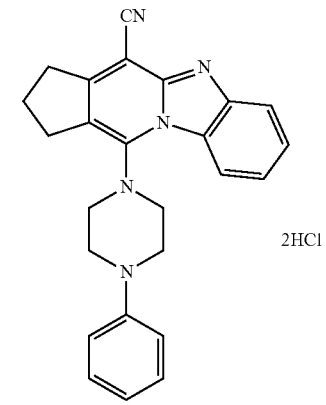 [SMILES: N#Cc1c2c(c(N3CCN(c4ccccc4)CC3)n3c1nc1ccccc13)CCC2 ; "2HCl"] 2HCl |
TABLE 18
| No. | Str |
|---|---|
| A35 | 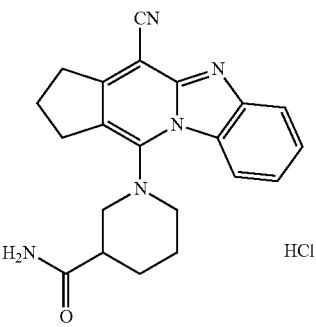 [SMILES: N#Cc1c2c(c(N3CCCC(C(N)=O)C3)n3c1nc1ccccc13)CCC2 ; Cl] 2HCl |
| A36 | 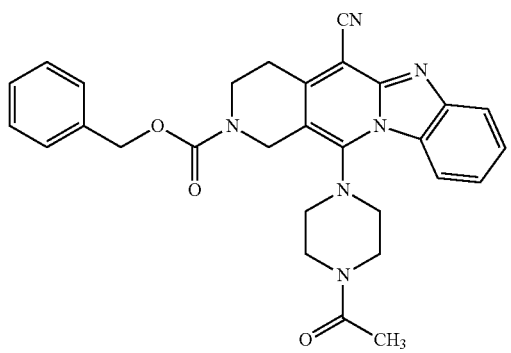 [SMILES: CC(=O)N1CCN(c2c3c(c(C#N)c4nc5ccccc5n24)CCN(C(=O)OCc2ccccc2)C3)CC1] HCl |
| A37 | 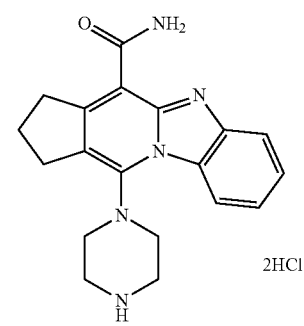 [SMILES: NC(=O)c1c2c(c(N3CCNCC3)n3c1nc1ccccc13)CCC2 ; "2HCl"] |
| A38 | 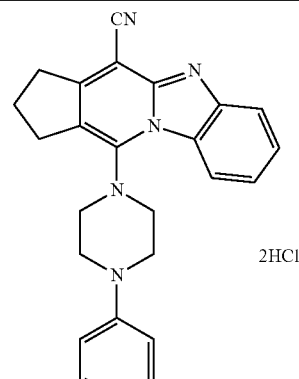 2HCl |
| A39 | 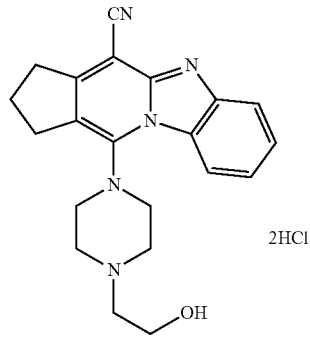 [SMILES: N#Cc1c2c(c(N3CCN(CCO)CC3)n3c1nc1ccccc13)CCC2 ; "2HCl"] 2HCl |

TABLE 18-continued
| No. | Str |
|---|---|
| A40 | 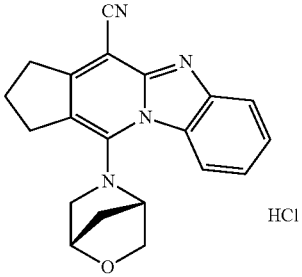 [SMILES: N#Cc1c2c(c(N3C[C@@H]4C[C@H]3CO4)n3c1nc1ccccc13)CCC2 ; Cl] HCl |
| A41 | 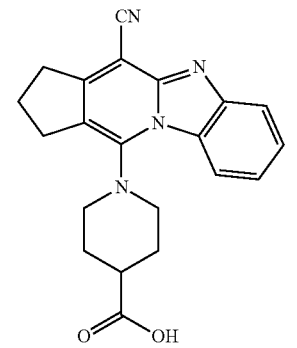 [SMILES: N#Cc1c2c(c(N3CCC(C(=O)O)CC3)n3c1nc1ccccc13)CCC2] |
| A42 | 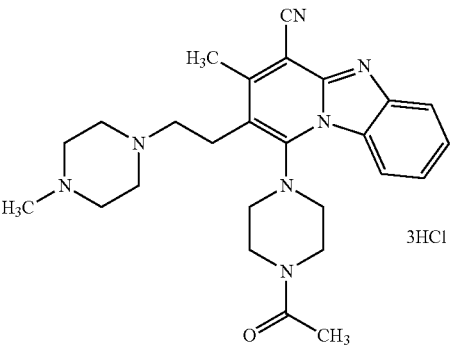 [SMILES: CC(=O)N1CCN(c2c(CCN3CCN(C)CC3)c(C)c(C#N)c3nc4ccccc4n23)CC1 ; "3HCl"] 3HCl |
TABLE 19
| No. | Str |
|---|---|
| A43 | 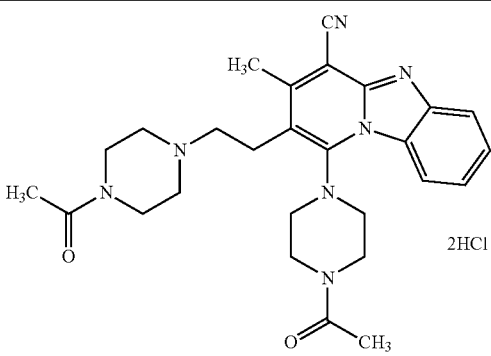 2HCl |
| A44 | 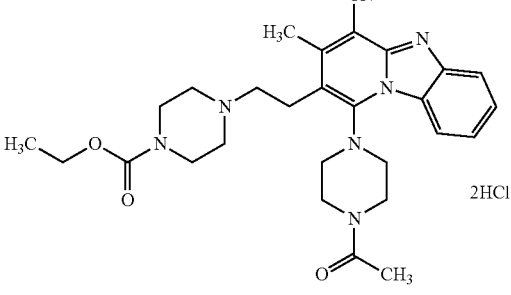 2HCl |
| A45 | 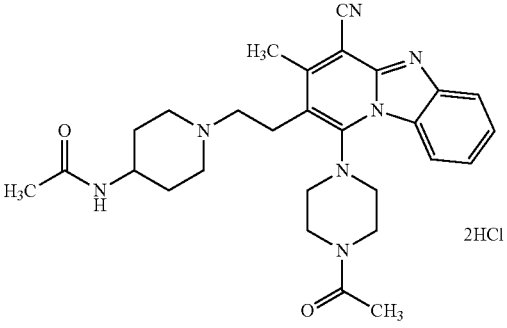 2HCl |
| A46 | 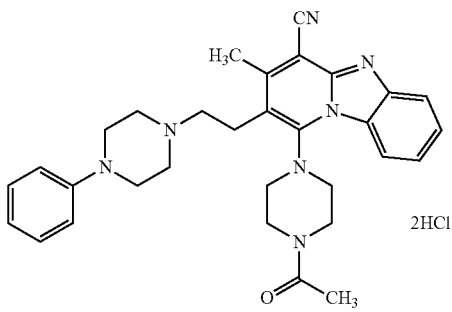 [SMILES: CC(=O)N1CCN(c2c(CCN3CCN(c4ccccc4)CC3)c(C)c(C#N)c3nc4ccccc4n23)CC1 ; "2HCl"] 2HCl |
| A47 | 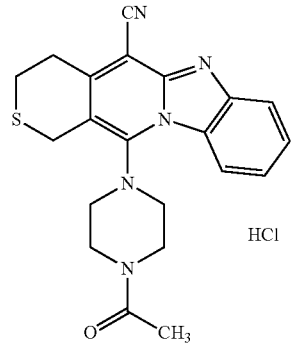 [SMILES: CC(=O)N1CCN(c2c3c(c(C#N)c4nc5ccccc5n24)CCSC3)CC1 ; Cl] HCl |

TABLE 19-continued
| No. | Str |
|-----|-----|
| A48 | 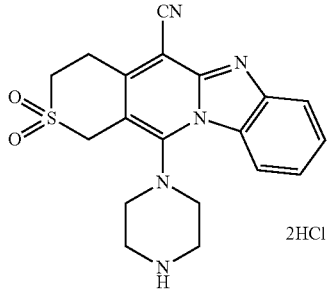 [SMILES: N#Cc1c2c(c(N3CCNCC3)n3c1nc1ccccc13)CS(=O)(=O)CC2 ; "2HCl"] 2HCl |
| A49 | 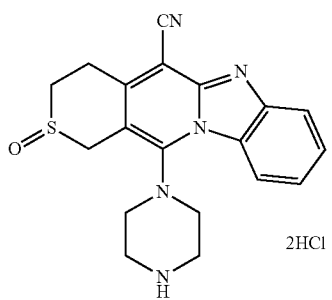 [SMILES: N#Cc1c2c(c(N3CCNCC3)n3c1nc1ccccc13)CS(=O)CC2 ; "2HCl"] 2HCl |
| A50 | 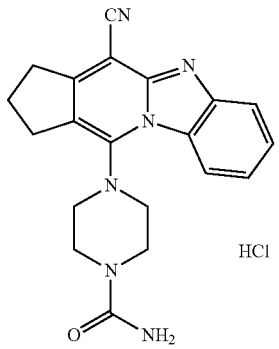 [SMILES: N#Cc1c2c(c(N3CCN(C(N)=O)CC3)n3c1nc1ccccc13)CCC2 ; Cl] HCl |
TABLE 20
| No. | Str |
|-----|-----|
| A51 | 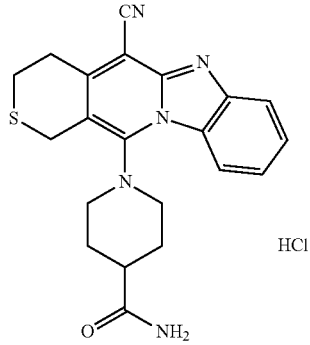 [SMILES: N#Cc1c2c(c(N3CCC(C(N)=O)CC3)n3c1nc1ccccc13)CSCC2 ; Cl] HCl |
TABLE 20-continued
| No. | Str |
|-----|-----|
| A52 | 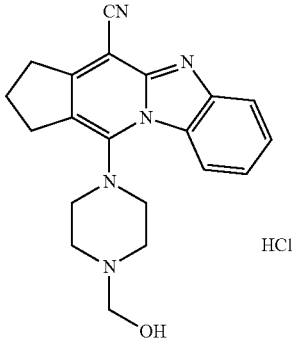 [SMILES: N#Cc1c2c(c(N3CCN(CO)CC3)n3c1nc1ccccc13)CCC2 ; Cl] HCl |
| A53 | 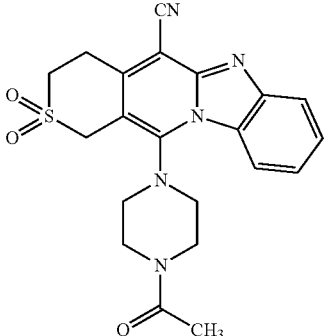 HCl |
| A54 | 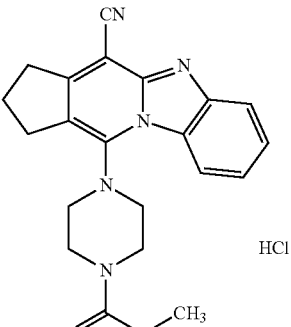 |
| A55 | 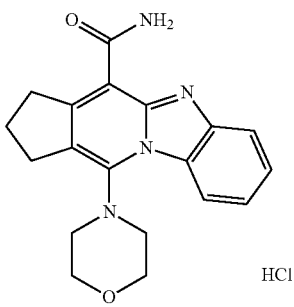 [SMILES: NC(=O)c1c2c(c(N3CCOCC3)n3c1nc1ccccc13)CCC2 ; Cl] HCl |

TABLE 20-continued

| No. | Str |
|---|---|
| A56 | (structure) HCl |
| A57 | (structure) HCl |
| A58 | (structure) HCl |

TABLE 21

| No. | Str |
|---|---|
| A59 | (structure) 2HCl |
| A60 | (structure) HCl |
| A61 | (structure) HCl |
| A62 | (structure) HCl |
| A63 | (structure) 2HCl |

TABLE 21-continued
| No. | Str |
|---|---|
| A64 | 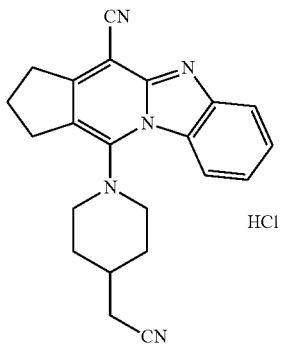 [SMILES: N#CCC1CCN(c2c3c(c(C#N)c4nc5ccccc5n24)CCC3)CC1 ; Cl] HCl |
| A65 | 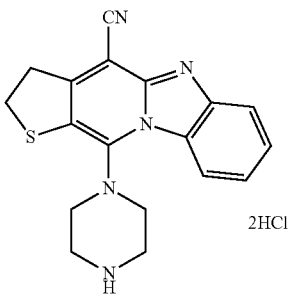 [SMILES: N#Cc1c2c(c(N3CCNCC3)n3c1nc1ccccc13)SCC2 ; "2HCl"] 2HCl |
| A66 | 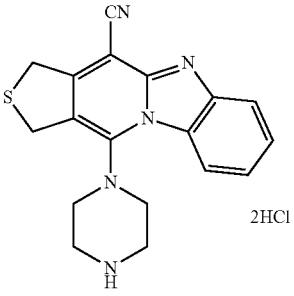 [SMILES: N#Cc1c2c(c(N3CCNCC3)n3c1nc1ccccc13)CSC2 ; "2HCl"] 2HCl |
TABLE 22
| No. | Str |
|---|---|
| A67 | 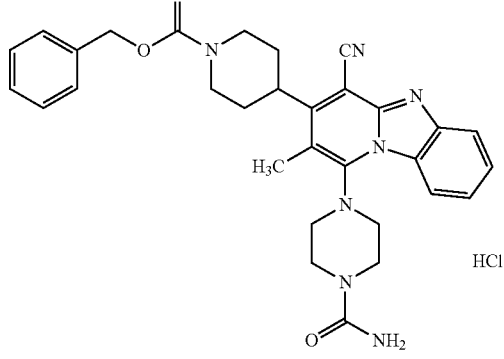 HCl |
| A68 | 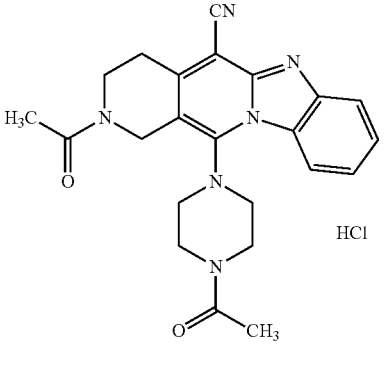 HCl |
| A69 | 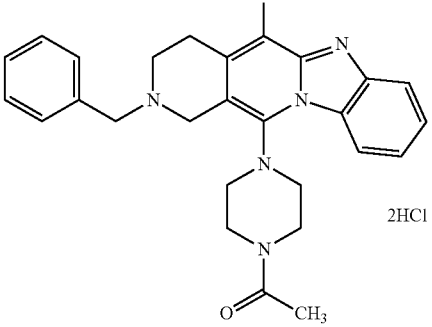 HCl |
| A70 | 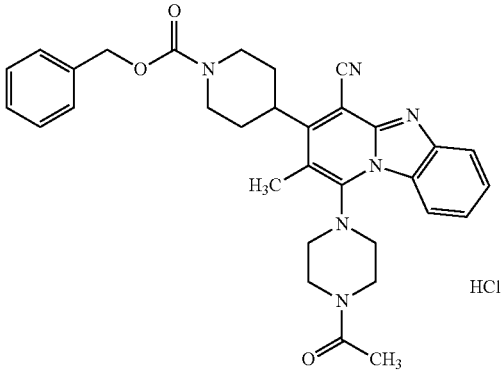 [SMILES: CC(=O)N1CCN(c2c(C)c(C3CCN(C(=O)OCc4ccccc4)CC3)c(C#N)c3nc4ccccc4n23)CC1 ; Cl] 2HCl |
| A71 | 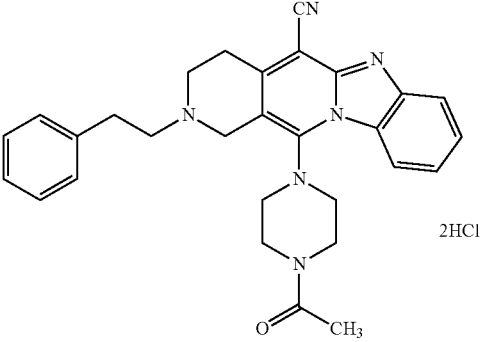 [SMILES: CC(=O)N1CCN(c2c3c(c(C#N)c4nc5ccccc5n24)CCN(CCc2ccccc2)C3)CC1 ; "2HCl"] 2HCl |

TABLE 22-continued
| No. | Str |
|---|---|
| A72 | 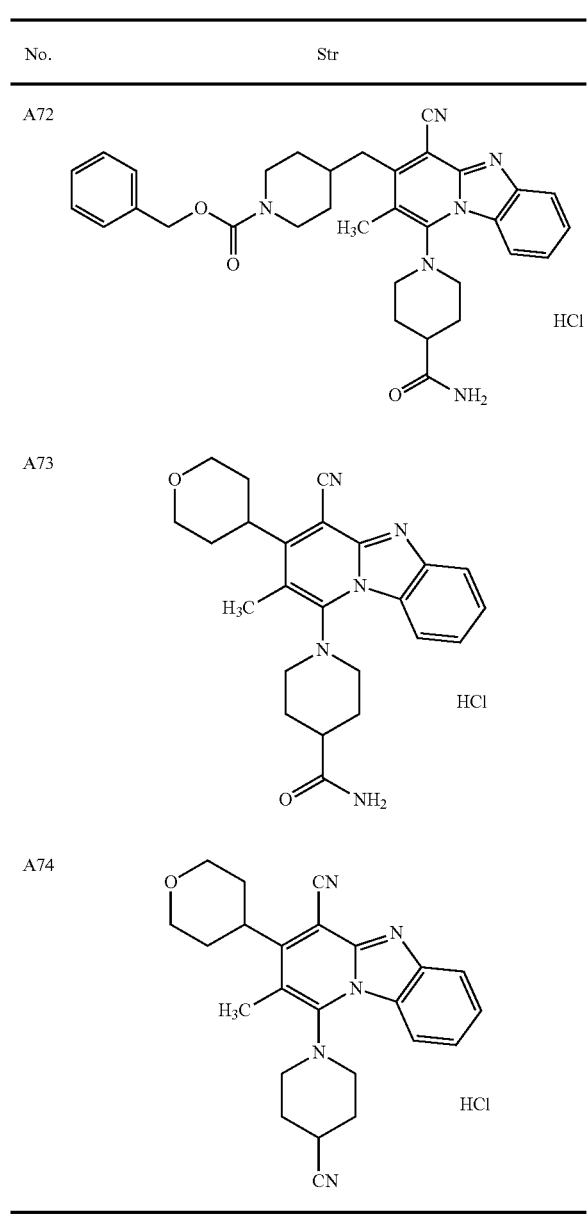 HCl |
| A73 | |
| A74 | |
TABLE 23
| No. | Str |
|---|---|
| A75 | 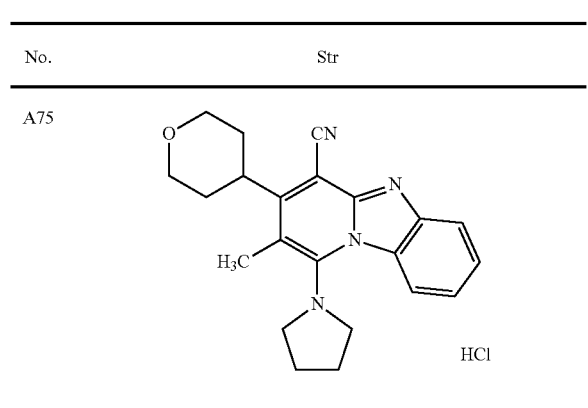 HCl |
TABLE 23-continued
| No. | Str |
|---|---|
| A76 | 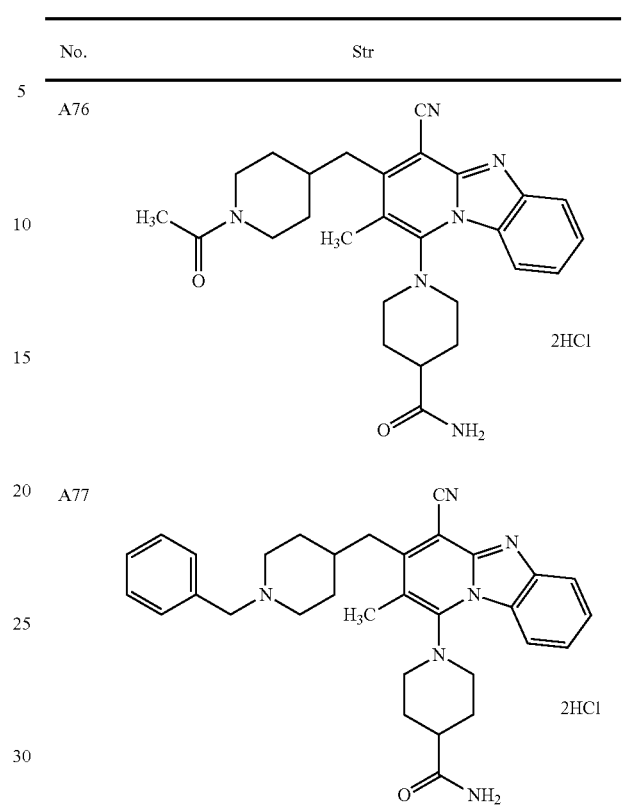 2HCl |
| A77 | 2HCl |
| A78 | 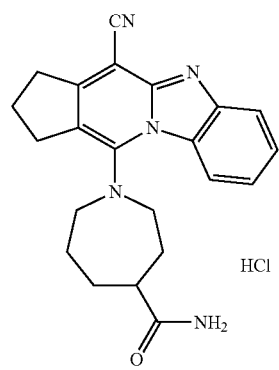 [SMILES: N#Cc1c2c(c(N3CCCC(C(N)=O)CC3)n3c1nc1ccccc13)CCC2 ; Cl] HCl |
| A79 | 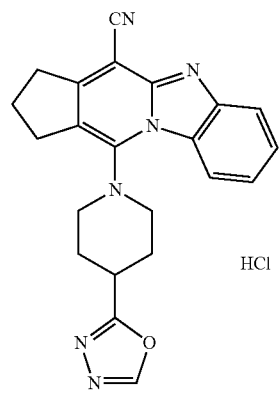 [SMILES: N#Cc1c2c(c(N3CCC(c4nnco4)CC3)n3c1nc1ccccc13)CCC2 ; Cl] HCl |

TABLE 23-continued
| No. | Str |
|---|---|
| A80 | 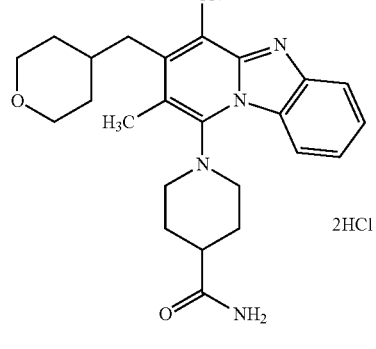 2HCl |
| A81 | 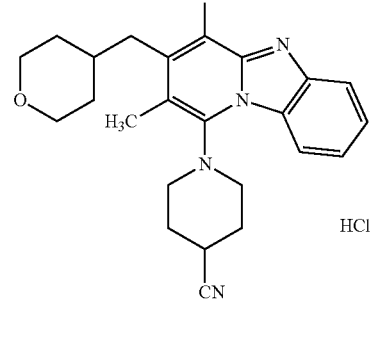 HCl |
| A82 | 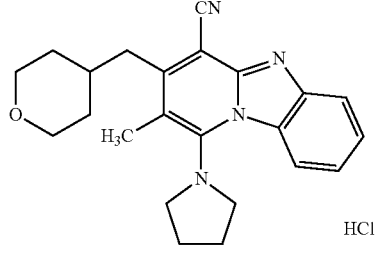 [SMILES: Cc1c(CC2CCOCC2)c(C#N)c2nc3ccccc3n2c1N1CCCC1 ; Cl] HCl |
TABLE 24
| No. | Str |
|---|---|
| A83 | 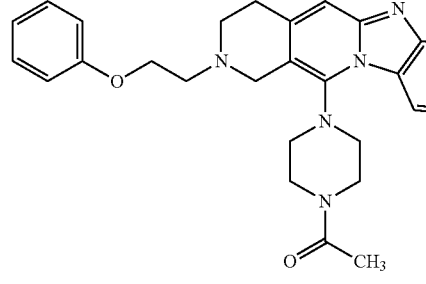 2HCl |
| A84 | 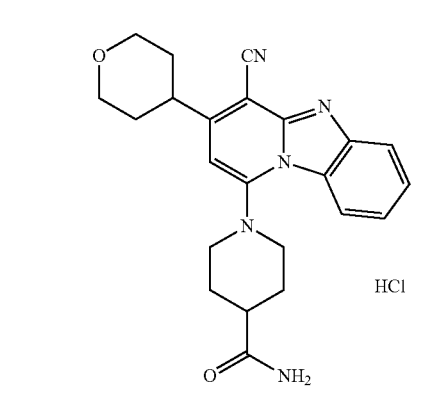 [SMILES: N#Cc1c(C2CCOCC2)cc(N2CCC(C(N)=O)CC2)n2c1nc1ccccc12 ; Cl] 2HCl |
| A85 | 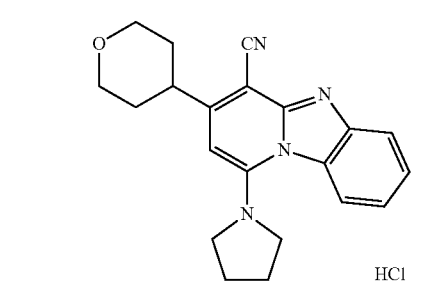 [SMILES: N#Cc1c(C2CCOCC2)cc(N2CCCC2)n2c1nc1ccccc12 ; Cl] HCl |
| A86 | HCl |
| A87 | HCl |

TABLE 24-continued
| No. | Str |
|---|---|
| A88 | 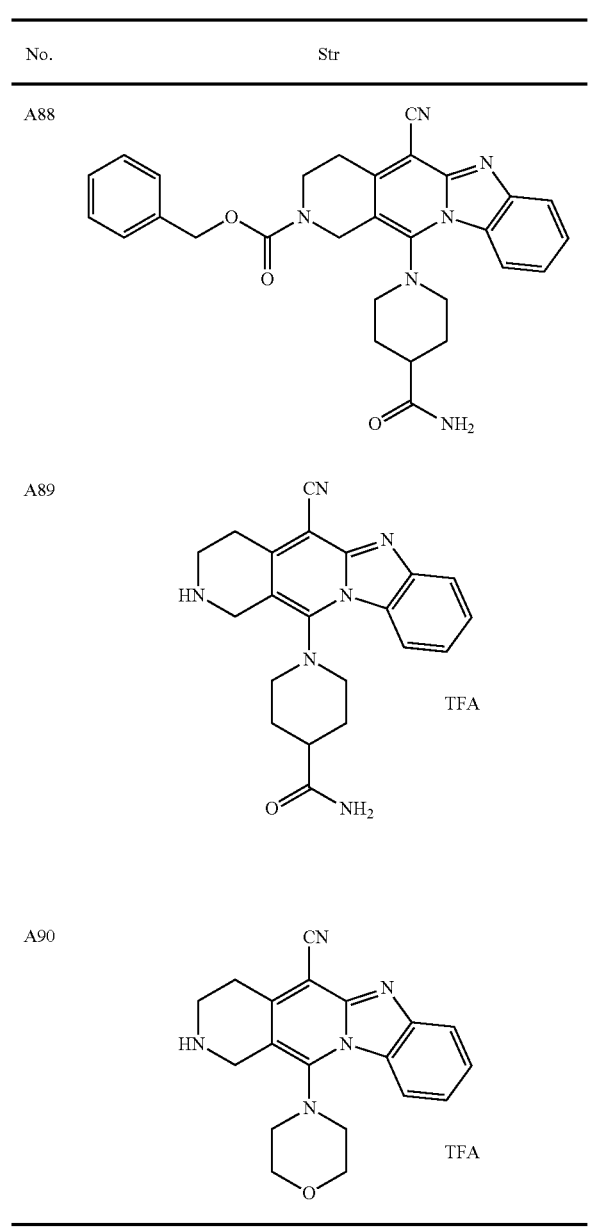 |
| A89 | |
| A90 | |
TABLE 25
| No. | Str |
|---|---|
| A91 | 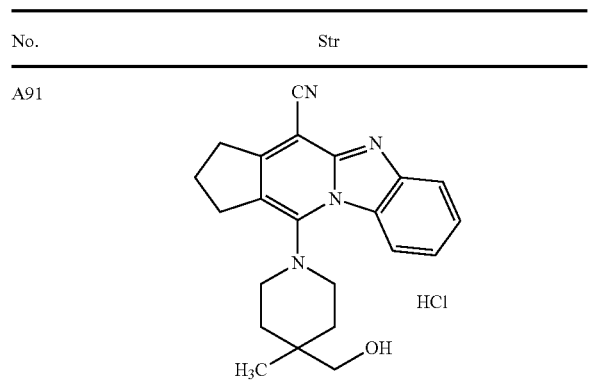 |
TABLE 25-continued
| No. | Str |
|---|---|
| A92 | 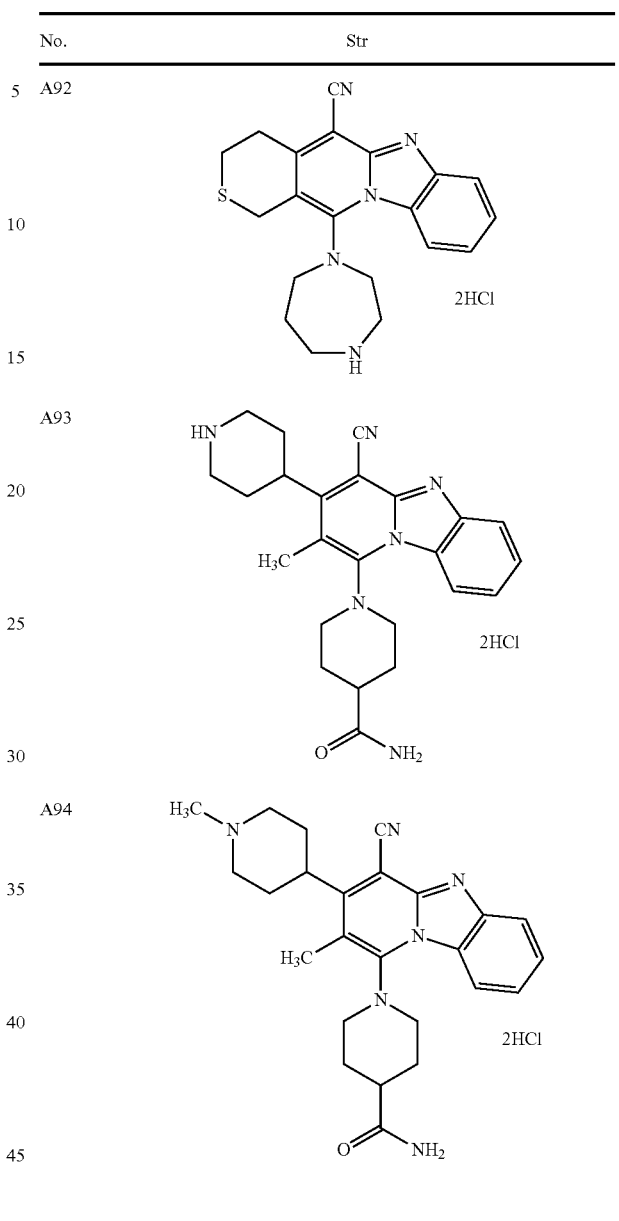 |
| A93 | |
| A94 | |
| A95 | 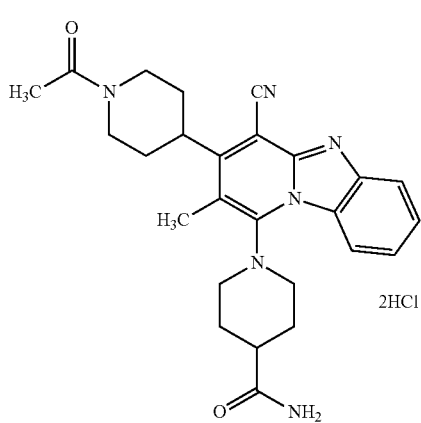 [SMILES: CC(=O)N1CCC(c2c(C)c(N3CCC(C(N)=O)CC3)n3c(nc4ccccc43)c2C#N)CC1 ; "2HCl"] |

TABLE 25-continued
| No. | Str |
|---|---|
| A96 | 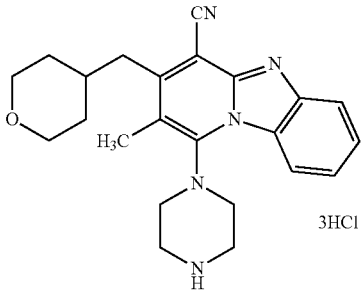 [SMILES: Cc1c(CC2CCOCC2)c(C#N)c2nc3ccccc3n2c1N1CCNCC1 ; "3HCl"] 3HCl |
| A97 | 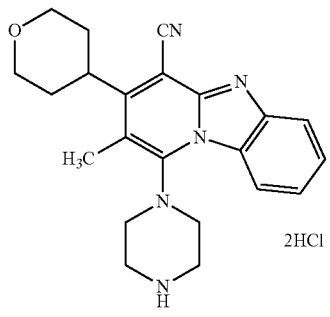 [SMILES: Cc1c(C2CCOCC2)c(C#N)c2nc3ccccc3n2c1N1CCNCC1 ; "2HCl"] 2HCl |
| A98 | 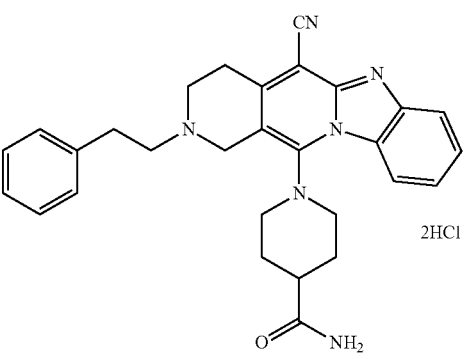 [SMILES: N#Cc1c2c(c(N3CCC(C(N)=O)CC3)n3c1nc1ccccc13)CN(CCc1ccccc1)CC2 ; "2HCl"] 2HCl |
TABLE 26
| No. | Str |
|---|---|
| A99 | 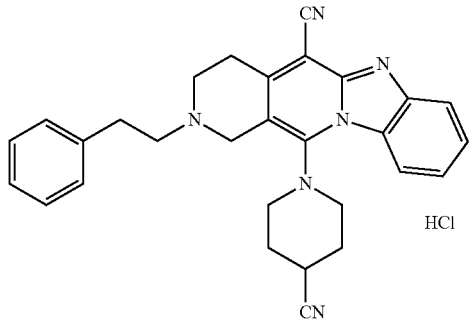 [SMILES: N#Cc1c2c(c(N3CCC(C#N)CC3)n3c1nc1ccccc13)CN(CCc1ccccc1)CC2 ; Cl] HCl |
| A100 | 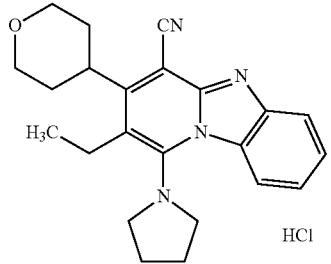 HCl |
| A101 | 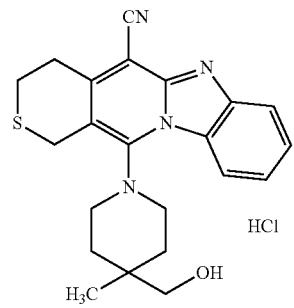 [SMILES: CC1(CO)CCN(c2c3c(c(C#N)c4nc5ccccc5n24)CCSC3)CC1 ; Cl] 2HCl |
| A102 | 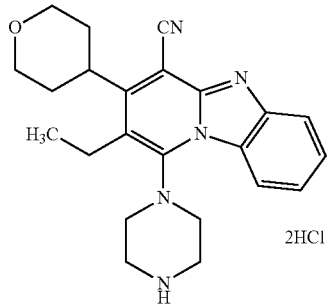 [SMILES: CCc1c(C2CCOCC2)c(C#N)c2nc3ccccc3n2c1N1CCNCC1 ; "2HCl"] 2HCl |
| A103 | 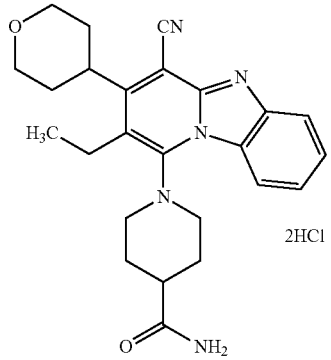 [SMILES: CCc1c(C2CCOCC2)c(C#N)c2nc3ccccc3n2c1N1CCC(C(N)=O)CC1 ; "2HCl"] HCl |
| A104 | 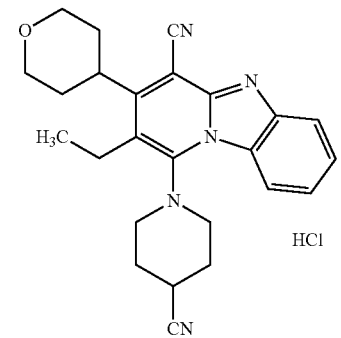 [SMILES: CCc1c(C2CCOCC2)c(C#N)c2nc3ccccc3n2c1N1CCC(C#N)CC1 ; Cl] HCl |
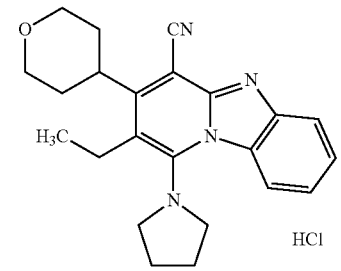 [SMILES: CCc1c(C2CCOCC2)c(C#N)c2nc3ccccc3n2c1N1CCCC1 ; Cl]

TABLE 26-continued
| No. | Str |
|---|---|
| A105 | 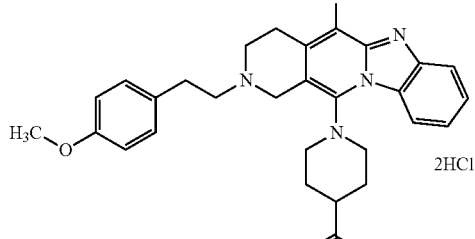 HCl |
| A106 | 2HCl |
TABLE 27
| No. | Str |
|---|---|
| A107 | 2HCl |
| A108 | 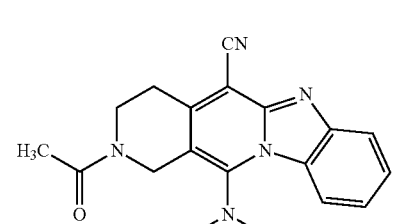 HCl |
TABLE 27-continued
| No. | Str |
|---|---|
| A109 | 2HCl |
| A110 | 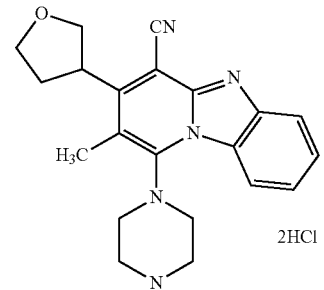 3HCl |
| A111 | 3HCl |
| A112 | 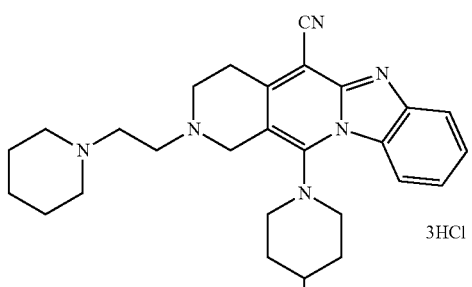 HCl |

TABLE 27-continued
| No. | Str |
|---|---|
| A113 | 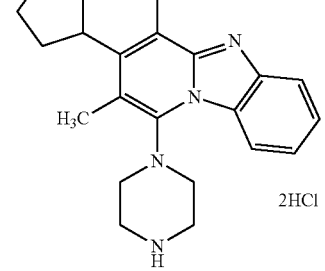 2HCl |
| A114 | 2HCl |
TABLE 28
| No. | Str |
|---|---|
| A115 | HCl |
| A116 | 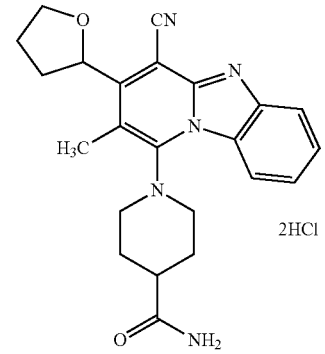 [SMILES: Cc1c(C2CCCO2)c(C#N)c2nc3ccccc3n2c1N1CCC(C(N)=O)CC1 ; "2HCl"] HCl |
TABLE 28-continued
| No. | Str |
|---|---|
| A117 | 2HCl |
| A118 | 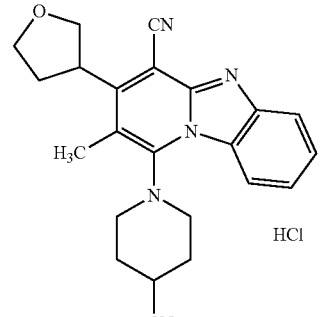 2HCl |
| A119 | HCl |
| A120 | 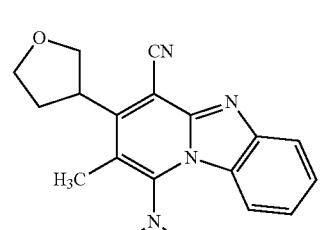 HCl |

TABLE 28-continued
| No. | Str |
|---|---|
| A121 | 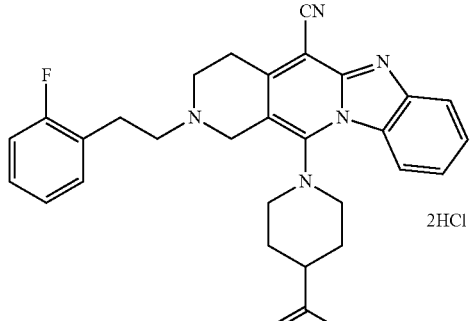 2HCl |
| A122 | 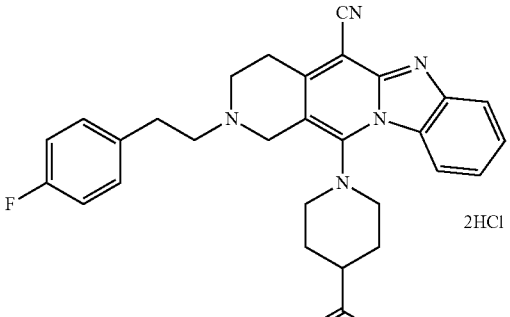 2HCl |
TABLE 29
| No. | Str |
|---|---|
| A123 | 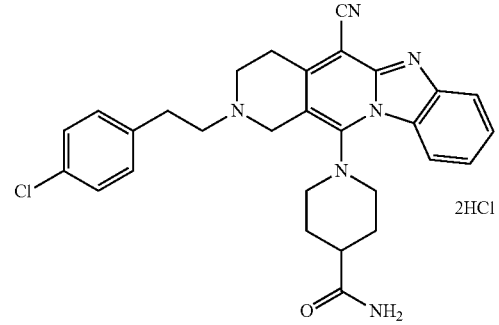 [SMILES: N#Cc1c2c(c(N3CCC(C(N)=O)CC3)n3c1nc1ccccc13)CN(CCc1ccc(Cl)cc1)CC2 ; "2HCl"] 2HCl |
| A124 | 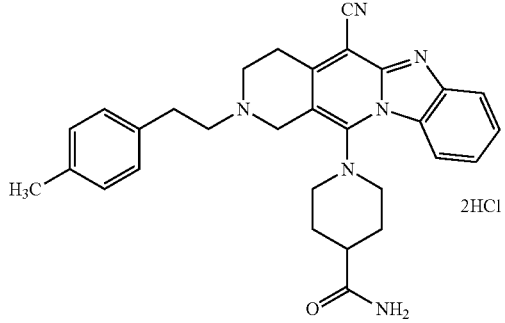 [SMILES: Cc1ccc(CCN2CCc3c(c(N4CCC(C(N)=O)CC4)n4c(nc5ccccc54)c3C#N)C2)cc1 ; "2HCl"] 2HCl |
| A125 | 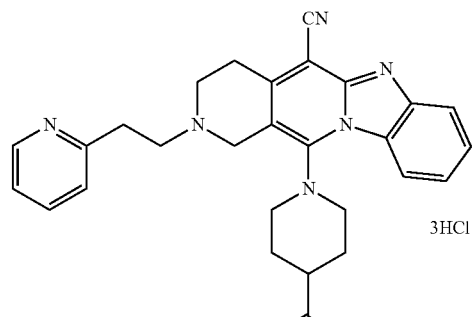 3HCl |
| A126 | 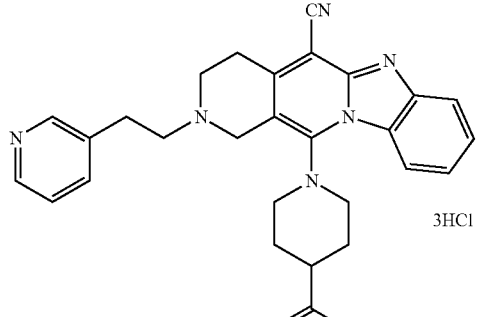 3HCl |
| A127 | 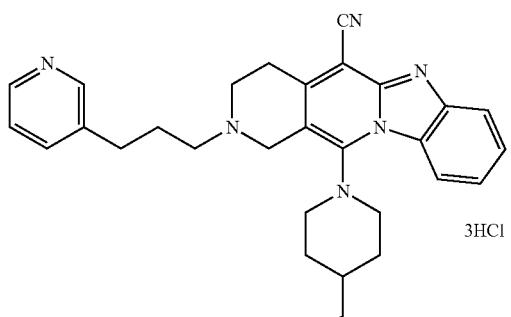 3HCl |
| A128 | 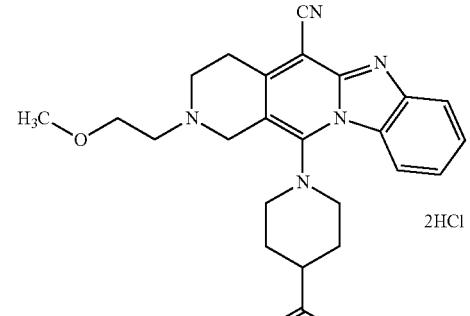 2HCl |

TABLE 29-continued
| No. | Str |
|---|---|
| A129 | 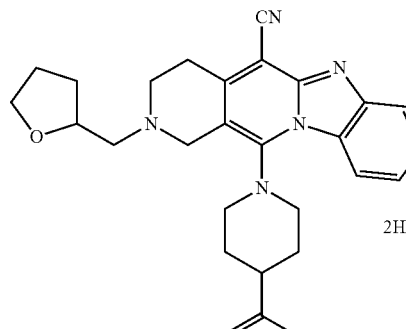 2HCl |
| A130 | 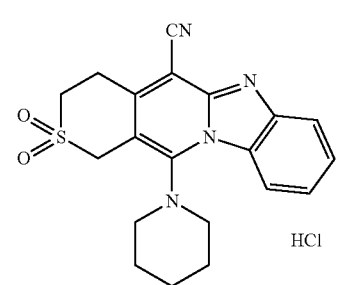 HCl |
TABLE 30
| No. | Str |
|---|---|
| A131 | 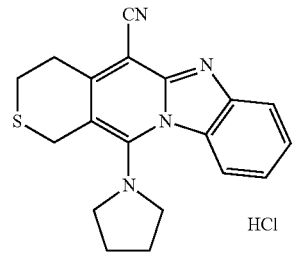 [SMILES: N#Cc1c2c(c(N3CCCC3)n3c1nc1ccccc13)CSCC2 ; Cl] HCl |
| A132 | 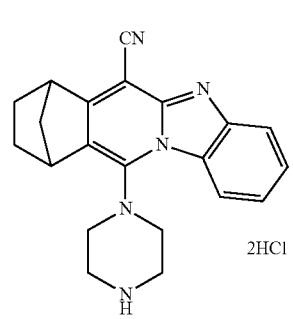 [SMILES: N#Cc1c2c(c(N3CCNCC3)n3c1nc1ccccc13)C1CCC2C1 ; "2HCl"] 2HCl |
TABLE 30-continued
| No. | Str |
|---|---|
| A133 | 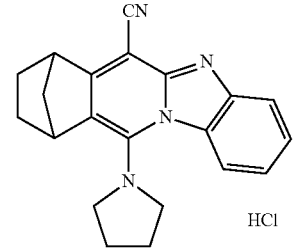 [SMILES: N#Cc1c2c(c(N3CCCC3)n3c1nc1ccccc13)C1CCC2C1 ; Cl] HCl |
| A134 | HCl |
| A135 | HCl |
| A136 | 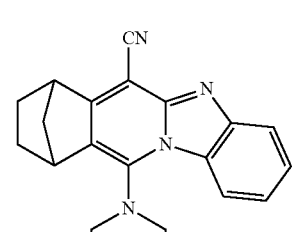 HCl |
| A137 | 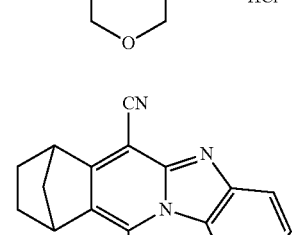 HCl |

75
TABLE 30-continued
| No. | Str |
|---|---|
| A138 | 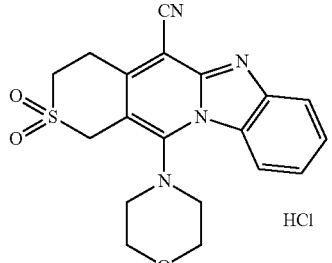 HCl |
| A139 | 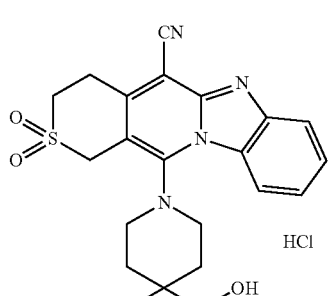 HCl |
| A140 | 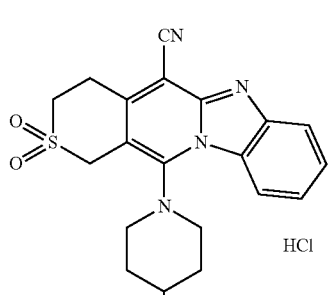 [SMILES: N#Cc1c2c(c(N3CCOCC3)n3c1nc1ccccc13)CS(=O)(=O)CC2 ; Cl] HCl |
TABLE 31
| No. | Str |
|---|---|
| A141 | 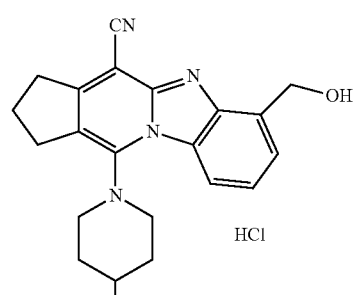 HCl |
76
TABLE 31-continued
| No. | Str |
|---|---|
| A142 | 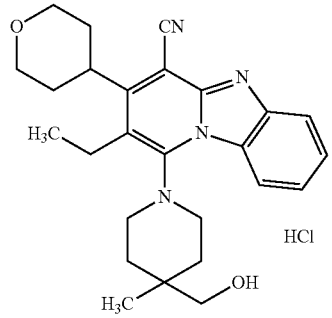 [SMILES: CCc1c(C2CCOCC2)c(C#N)c2nc3ccccc3n2c1N1CCC(C)(CO)CC1 ; Cl] HCl |
| A143 | 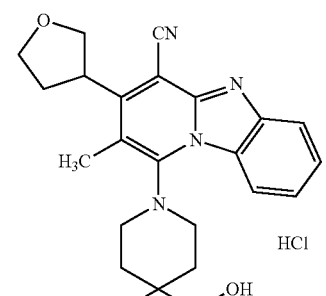 HCl |
| A144 | 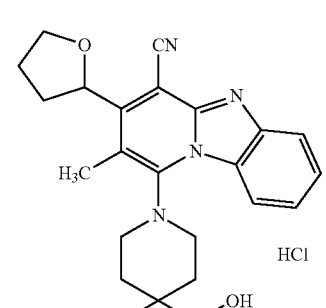 HCl |
| A145 | 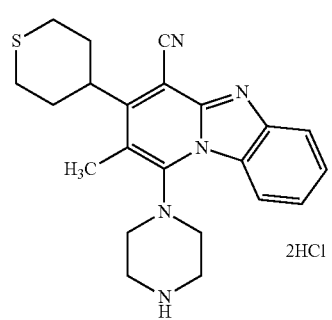 [SMILES: Cc1c(C2CCSCC2)c(C#N)c2nc3ccccc3n2c1N1CCNCC1 ; "2HCl"] 2HCl |

TABLE 31-continued
| No. | Str |
|-----|-----|
| A146 | 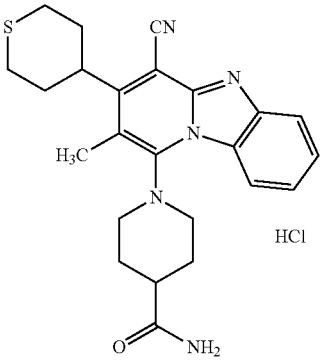 [SMILES: Cc1c(C2CCSCC2)c(C#N)c2nc3ccccc3n2c1N1CCC(C(N)=O)CC1 ; Cl] HCl |
| A147 | 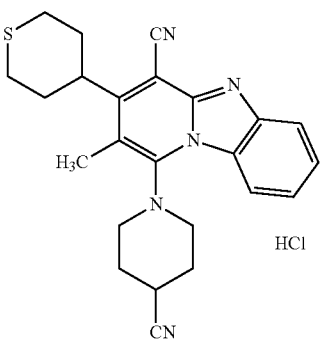 [SMILES: Cc1c(C2CCSCC2)c(C#N)c2nc3ccccc3n2c1N1CCC(C#N)CC1 ; Cl] HCl |
| A148 | 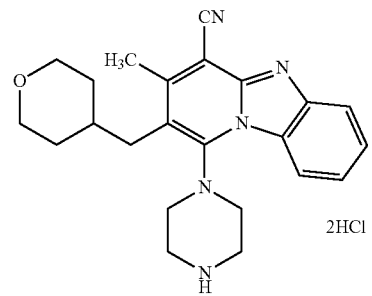 [SMILES: Cc1c(CC2CCOCC2)c(N2CCNCC2)n2c(nc3ccccc32)c1C#N ; "2HCl"] 2HCl |
TABLE 32
| No. | Str |
|-----|-----|
| A149 | 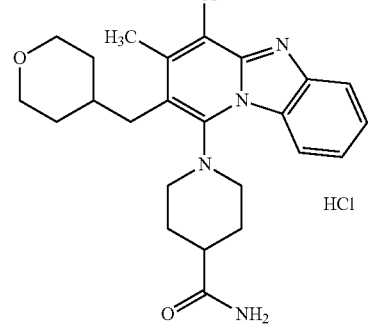 HCl |
| A150 | 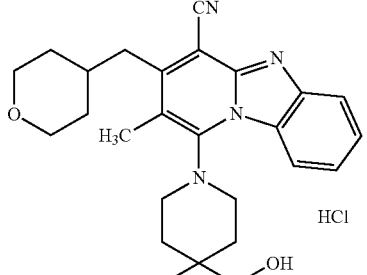 HCl |
| A151 | 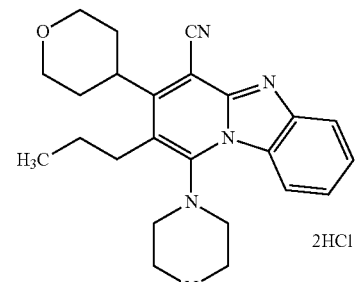 2HCl |
| A152 | 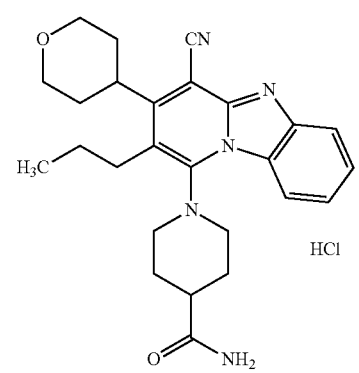 [SMILES: CCCc1c(C2CCOCC2)c(C#N)c2nc3ccccc3n2c1N1CCC(C(N)=O)CC1 ; Cl] HCl |
| A153 | 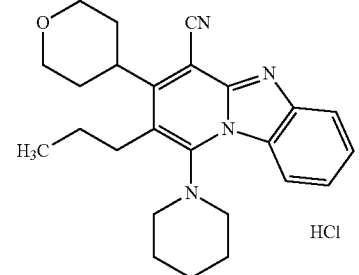 HCl |
| A154 | 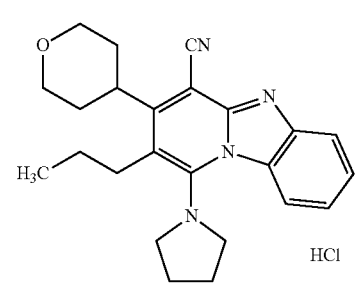 [SMILES: CCCc1c(C2CCOCC2)c(C#N)c2nc3ccccc3n2c1N1CCCC1 ; Cl] HCl |

TABLE 32-continued
| No. | Str |
|---|---|
| A155 | 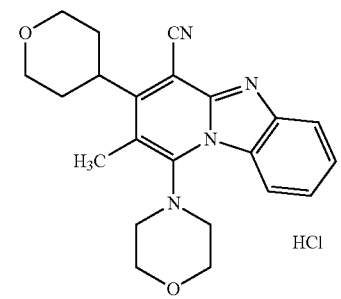 [SMILES: Cc1c(C2CCOCC2)c(C#N)c2nc3ccccc3n2c1N1CCOCC1 ; Cl] HCl |
| A156 | 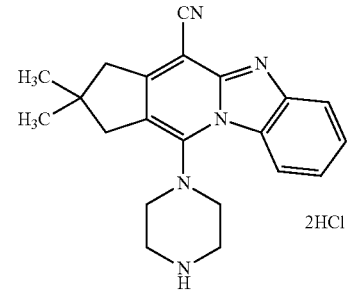 [SMILES: CC1(C)Cc2c(c(N3CCNCC3)n3c(nc4ccccc43)c2C#N)C1 ; "2HCl"] 2HCl |
TABLE 33
| No. | Str |
|---|---|
| A157 | 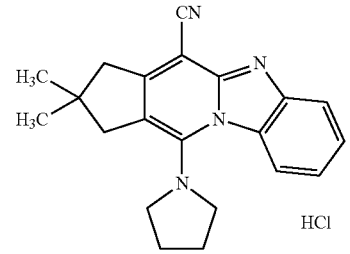 [SMILES: CC1(C)Cc2c(c(N3CCCC3)n3c(nc4ccccc43)c2C#N)C1 ; Cl] HCl |
| A158 | 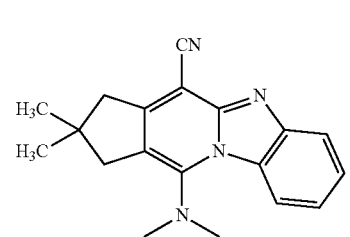 HCl |
TABLE 33-continued
| No. | Str |
|---|---|
| A159 |  HCl |
| A160 | HCl |
| A161 | 2HCl |
| A162 | HCl |
| A163 | HCl |

TABLE 33-continued
| No. | Str |
|---|---|
| A164 | 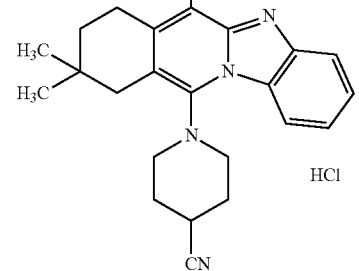 HCl |
TABLE 34
| No. | Str |
|---|---|
| A165 | 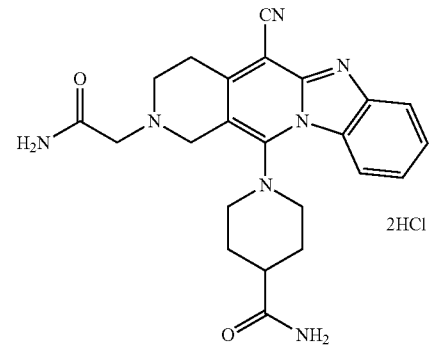 [SMILES: N#Cc1c2c(c(N3CCC(C(N)=O)CC3)n3c1nc1ccccc13)CN(CC(N)=O)CC2 ; "2HCl"] HCl |
| A166 | 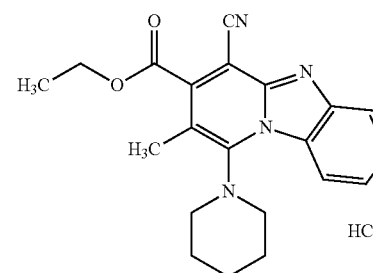 2HCl |
| A167 | 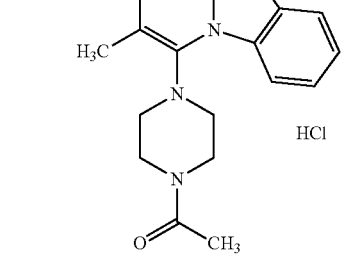 HCl |
TABLE 34-continued
| No. | Str |
|---|---|
| A168 | 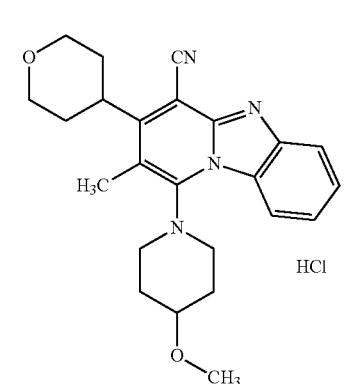 [SMILES: Cc1c(C2CCOCC2)c(C#N)c2nc3ccccc3n2c1N1CCC(CO)CC1 ; Cl] HCl |
| A169 | 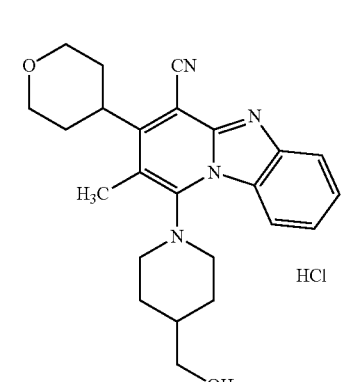 HCl |
| A170 | HCl |
| A171 | 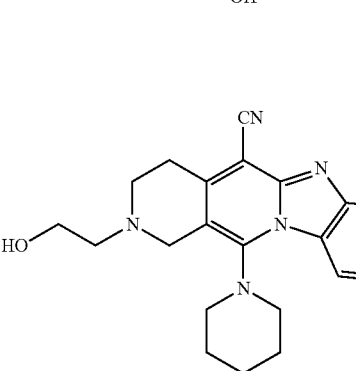 HCl |

TABLE 34-continued
| No. | Str |
|---|---|
| A172 | 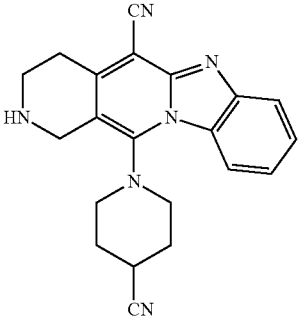 [SMILES: N#Cc1c2c(c(N3CCC(C#N)CC3)n3c1nc1ccccc13)CNCC2] |
TABLE 35
| No. | Str |
|---|---|
| A173 | 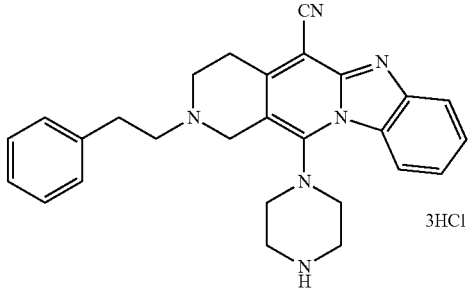 [SMILES: N#Cc1c2c(c(N3CCNCC3)n3c1nc1ccccc13)CN(CCc1ccccc1)CC2 ; "3HCl"] 3HCl |
| A174 | 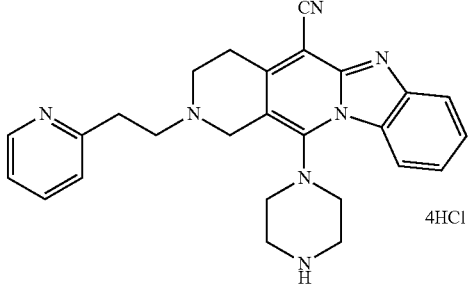 4HCl |
| A175 | 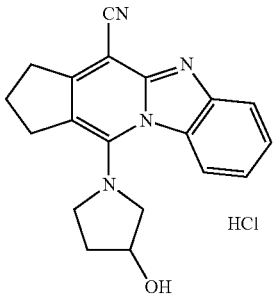 [SMILES: N#Cc1c2c(c(N3CCC(O)C3)n3c1nc1ccccc13)CCC2 ; Cl] HCl |
TABLE 35-continued
| No. | Str |
|---|---|
| A176 | 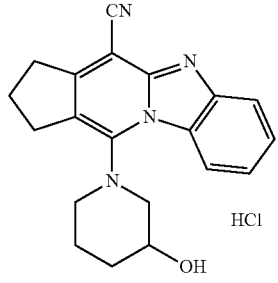 [SMILES: N#Cc1c2c(c(N3CCCC(O)C3)n3c1nc1ccccc13)CCC2 ; Cl] HCl |
| A177 | 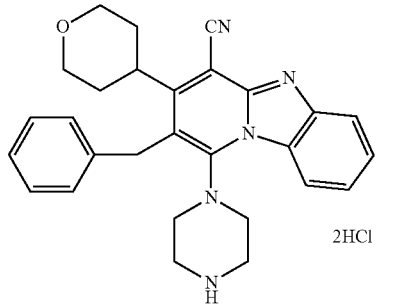 [SMILES: N#Cc1c(C2CCOCC2)c(Cc2ccccc2)c(N2CCNCC2)n2c1nc1ccccc12 ; "2HCl"] 2HCl |
| A178 | 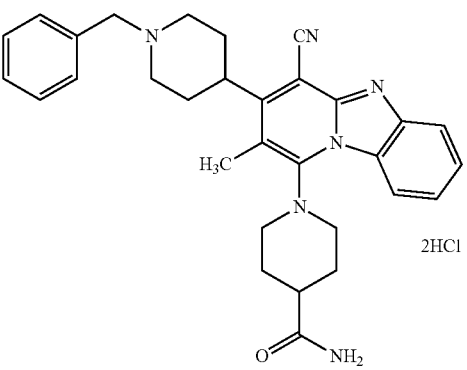 [SMILES: Cc1c(C2CCN(Cc3ccccc3)CC2)c(C#N)c2nc3ccccc3n2c1N1CCC(C(N)=O)CC1 ; "2HCl"] 2HCl |
| A179 | 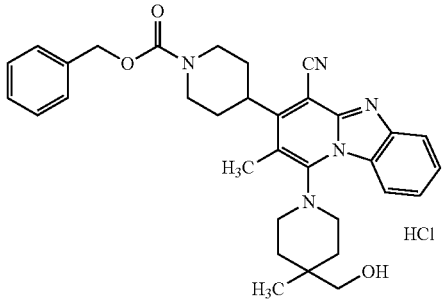 [SMILES: Cc1c(C2CCN(C(=O)OCc3ccccc3)CC2)c(C#N)c2nc3ccccc3n2c1N1CCC(C)(CO)CC1 ; Cl] HCl |
| A180 | 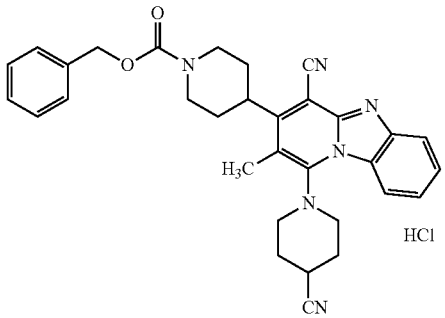 [SMILES: Cc1c(C2CCN(C(=O)OCc3ccccc3)CC2)c(C#N)c2nc3ccccc3n2c1N1CCC(C#N)CC1 ; Cl] HCl |

US 8,822,688 B2
TABLE 35-continued
| No. | Str |
|---|---|
| A181 | 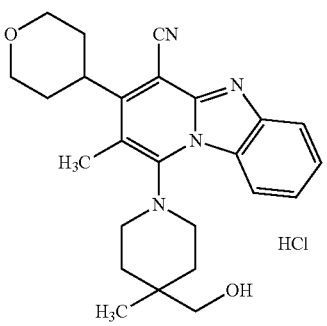 HCl |
| A182 | 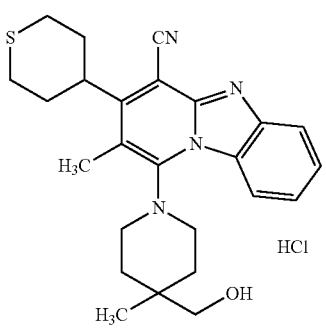 [SMILES: Cc1c(C2CCSCC2)c(C#N)c2nc3ccccc3n2c1N1CCC(C)(CO)CC1 ; Cl] HCl |
TABLE 36
| No. | Str |
|---|---|
| A183 | 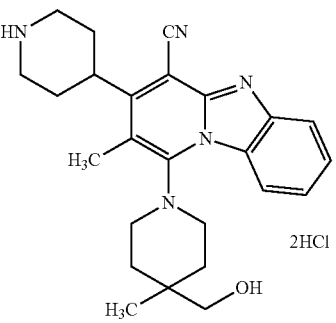 2HCl |
| A184 | 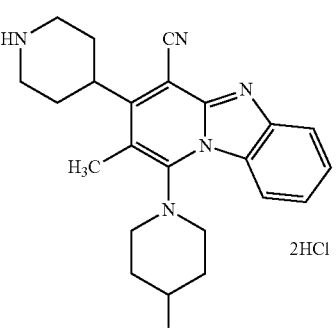 2HCl |
TABLE 36-continued
| No. | Str |
|---|---|
| A185 | 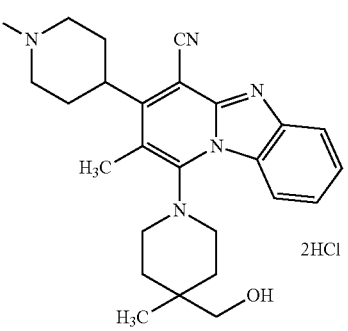 2HCl |
| A186 | 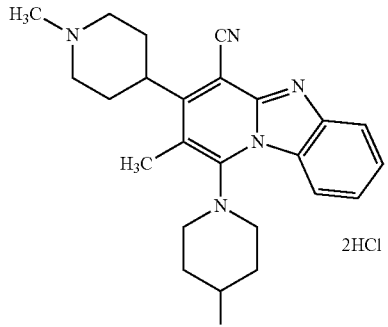 [SMILES: Cc1c(C2CCN(C)CC2)c(C#N)c2nc3ccccc3n2c1N1CCC(C)(CO)CC1 ; "2HCl"] 2HCl |
| A187 | 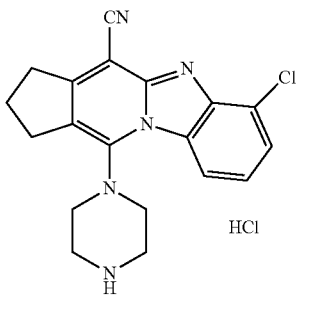 [SMILES: N#Cc1c2c(c(N3CCNCC3)n3c1nc1c(Cl)cccc13)CCC2 ; Cl] HCl |
| A188 | 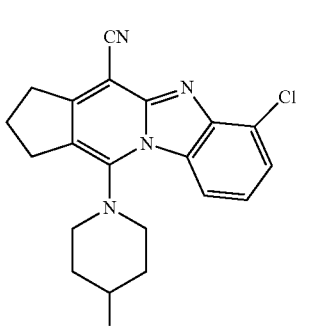 |

TABLE 36-continued
| No. | Str |
|---|---|
| A189 | 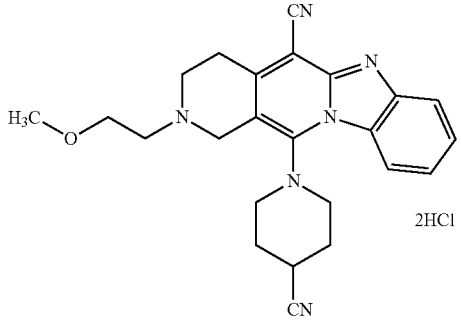 [SMILES: COCCN1CCc2c(c(N3CCC(C#N)CC3)n3c(nc4ccccc43)c2C#N)C1 ; "2HCl"] 2HCl |
| A190 | 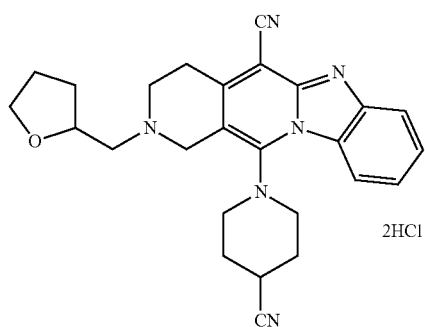 [SMILES: N#Cc1c2c(c(N3CCC(C#N)CC3)n3c1nc1ccccc13)CN(CC1CCCO1)CC2 ; "2HCl"] 2HCl |
TABLE 37
| No. | Str |
|---|---|
| A191 | 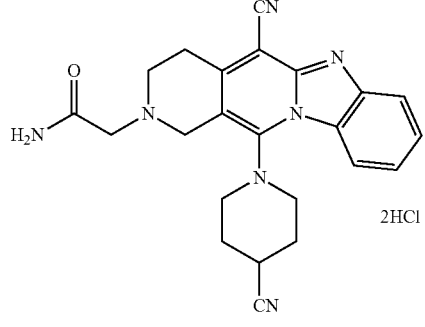 [SMILES: N#Cc1c2c(c(N3CCC(C#N)CC3)n3c1nc1ccccc13)CN(CC(N)=O)CC2 ; "2HCl"] 2HCl |
| A192 | 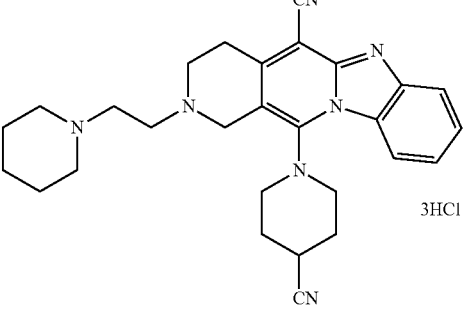 3HCl |
TABLE 37-continued
| No. | Str |
|---|---|
| A193 | 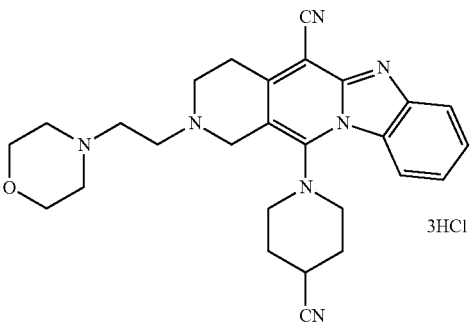 [SMILES: N#Cc1c2c(c(N3CCC(C#N)CC3)n3c1nc1ccccc13)CN(CCN1CCOCC1)CC2 ; "3HCl"] 3HCl |
| A194 | 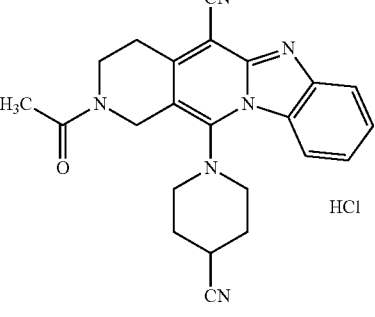 HCl |
| A195 | 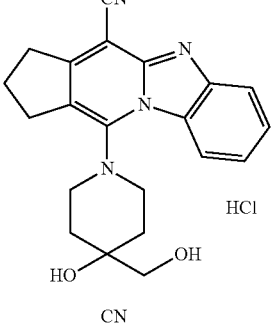 HCl |
| A196 | 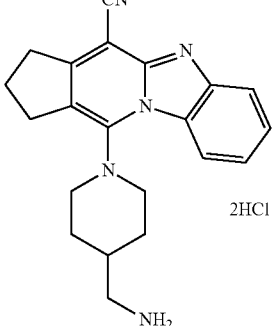 2HCl |
| A197 | 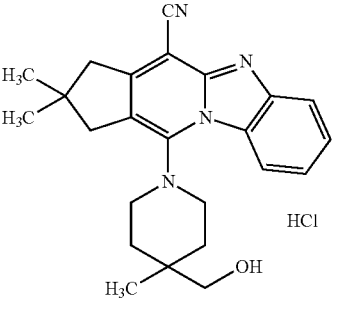 [SMILES: CC1(C)Cc2c(c(N3CCC(C)(CO)CC3)n3c(nc4ccccc43)c2C#N)C1 ; Cl] HCl |

TABLE 37-continued
| No. | Str |
|---|---|
| A198 | 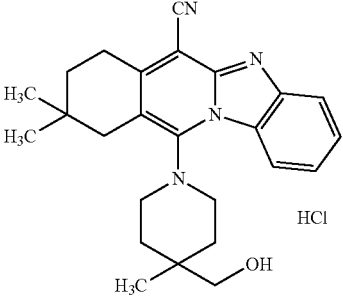 [SMILES: CC1(C)CCc2c(c(N3CCC(C)(CO)CC3)n3c(nc4ccccc43)c2C#N)C1 ; Cl] HCl |
TABLE 38
| No. | Str |
|---|---|
| A199 | HCl |
| A200 | 3HCl |
| A201 | 3HCl |
| A202 | 3HCl |
| A203 | HCl |
| A204 | 2HCl |
| A205 | HCl |
| A206 | |

TABLE 38-continued
| No. | Str |
|---|---|
| A207 | 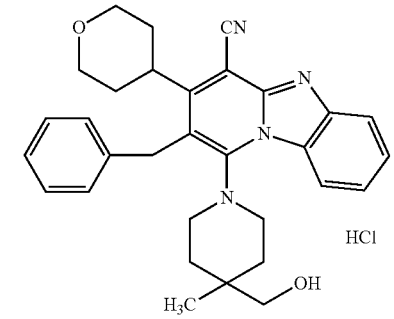 [SMILES: CC1(CO)CCN(c2c(Cc3ccccc3)c(C3CCOCC3)c(C#N)c3nc4ccccc4n23)CC1 ; Cl] HCl |
| A208 | 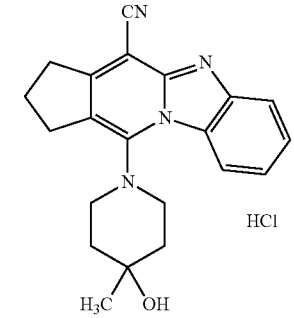 [SMILES: CC1(O)CCN(c2c3c(c(C#N)c4nc5ccccc5n24)CCC3)CC1 ; Cl] HCl |
TABLE 39
| No. | Str |
|---|---|
| A209 | 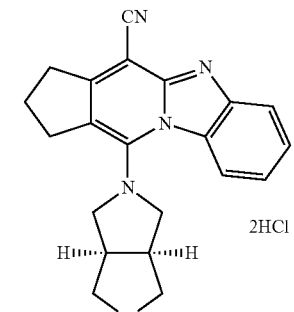 HCl |
| A210 | 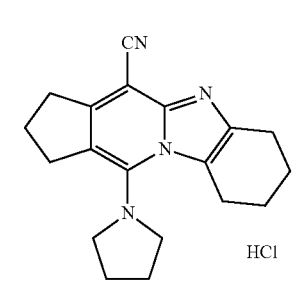 [SMILES: N#Cc1c2c(c(N3CCCC3)n3c4c(nc13)CCCC4)CCC2 ; Cl] HCl |
| A211 | 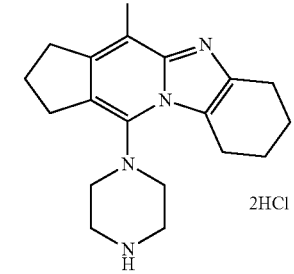 HCl |
| A212 | HCl |
| A213 | 2HCl |
| A214 | HCl |
| A215 | 2HCl |

TABLE 39-continued
| No. | Str |
|---|---|
| A216 | 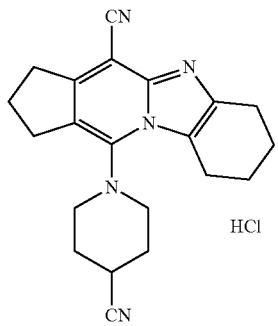 [SMILES: N#Cc1c2c(c(N3CCC(C#N)CC3)n3c4c(nc13)CCCC4)CCC2 ; Cl] HCl |
TABLE 40
| No. | Str |
|---|---|
| A217 | 2HCl |
| A218 | 2HCl |
| A219 | 3HCl |
| A220 | 2HCl |
| A221 | 2HCl |
| A222 | HCl |
| A223 | HCl |
| A224 | HCl |

TABLE 41

| No. | Str |
|---|---|
| A225 | |
| A226 | |
| A227 | |
| A228 | |
| A229 | |
| A230 | |
| A231 | |
| A232 | |
| A233 | |

TABLE 41-continued
| No. | Str |
|---|---|
| A234 | 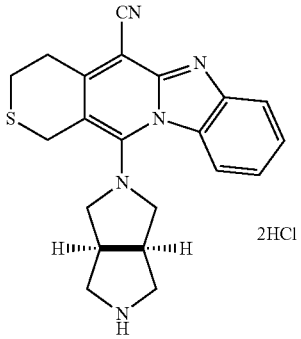 2HCl |
TABLE 42
| No. | Str |
|---|---|
| A235 | 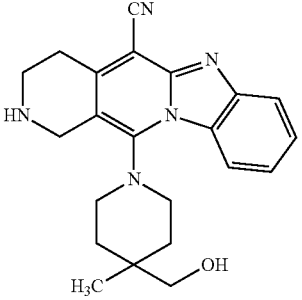 [SMILES: CC1(CO)CCN(c2c3c(c(C#N)c4nc5ccccc5n24)CCNC3)CC1] |
| A236 | |
| A237 | 2HCl |
TABLE 42-continued
| No. | Str |
|---|---|
| A238 | 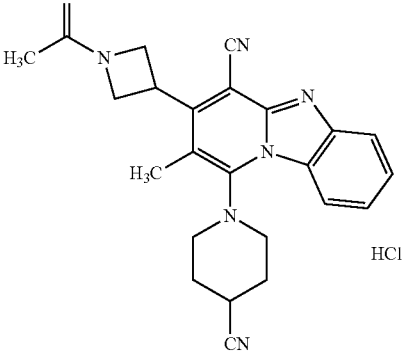 HCl |
| A239 | HCl |
| A240 | 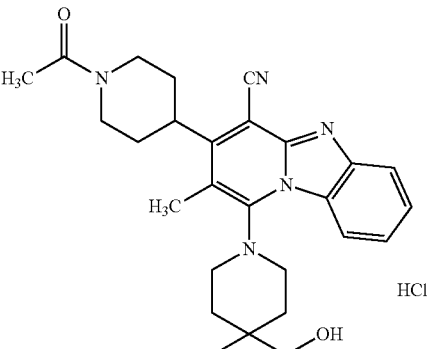 HCl |
| A241 | HCl |

TABLE 42-continued
| No. | Str |
|---|---|
| A242 | 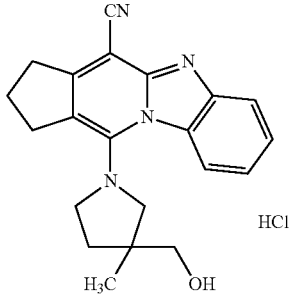 [SMILES: CC1(CO)CCN(c2c3c(c(C#N)c4nc5ccccc5n24)CCC3)C1 ; Cl] HCl |
TABLE 43
| No. | Str |
|---|---|
| A243 | 2HCl |
| A244 | 2HCl |
| A245 | 2HCl |
| A246 | 2HCl |
| A247 | HCl |
| A248 | HCl |
| A249 | HCl |
| A250 | HCl |

TABLE 43-continued
| No. | Str |
|---|---|
| A251 | 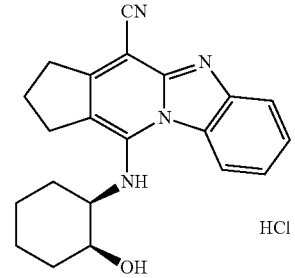 [SMILES: N#Cc1c2c(c(N[C@@H]3CCCC[C@@H]3O)n3c1nc1ccccc13)CCC2 ; Cl] HCl |
| A252 | 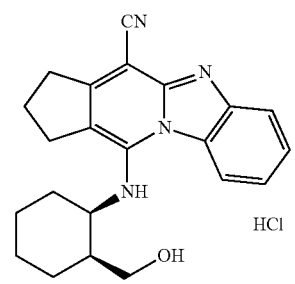 [SMILES: N#Cc1c2c(c(N[C@@H]3CCCC[C@@H]3CO)n3c1nc1ccccc13)CCC2 ; Cl] HCl |
TABLE 44
| No. | Str |
|---|---|
| A253 | 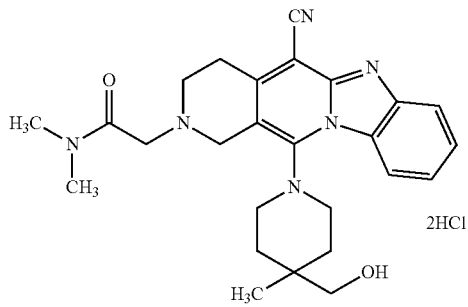 [SMILES: CN(C)C(=O)CN1CCc2c(c(N3CCC(C)(CO)CC3)n3c(nc4ccccc43)c2C#N)C1 ; "2HCl"] 2HCl |
| A254 | 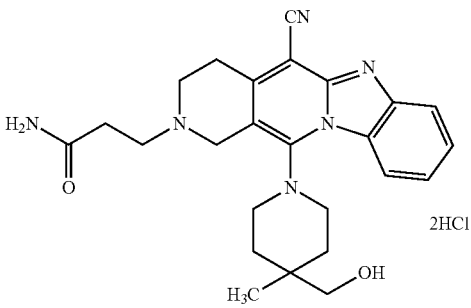 [SMILES: CC1(CO)CCN(c2c3c(c(C#N)c4nc5ccccc5n24)CCN(CCC(N)=O)C3)CC1 ; "2HCl"] 2HCl |
TABLE 44-continued
| No. | Str |
|---|---|
| A255 | 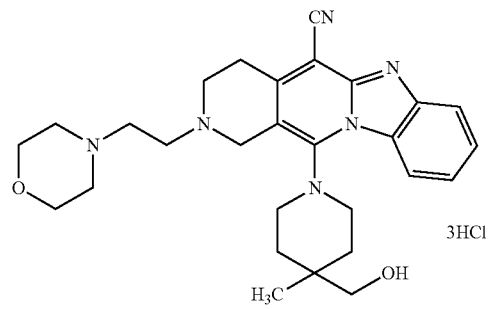 [SMILES: CC1(CO)CCN(c2c3c(c(C#N)c4nc5ccccc5n24)CCN(CCN2CCOCC2)C3)CC1 ; "3HCl"] 3HCl |
| A256 | 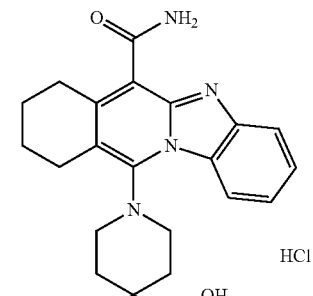 HCl |
| A257 | 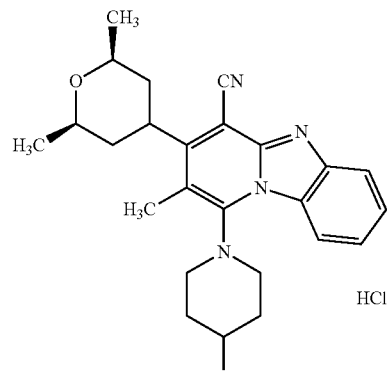 HCl |
| A258 | 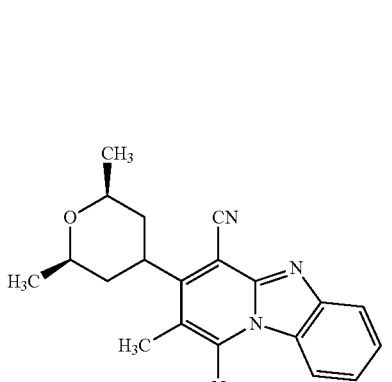 HCl |

TABLE 44-continued
| No. | Str |
|---|---|
| A259 | 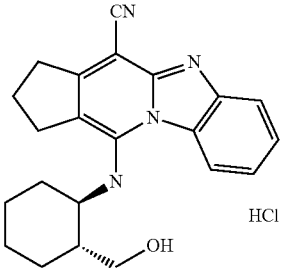 [SMILES: N#Cc1c2c(c(N[C@@H]3CCCC[C@H]3CO)n3c1nc1ccccc13)CCC2 ; Cl] HCl |
| A260 | 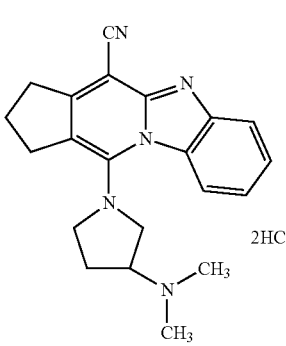 2HCl |
TABLE 45
| No. | Str |
|---|---|
| A261 | 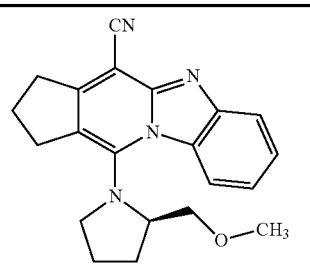 HCl |
| A262 | 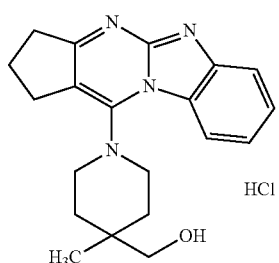 HCl |
| A263 | 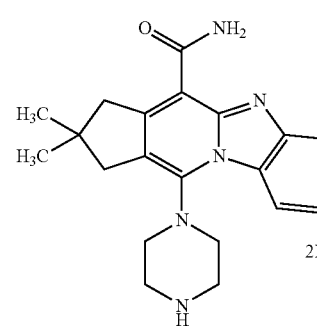 2HCl |
TABLE 45-continued
| No. | Str |
|---|---|
| A264 | 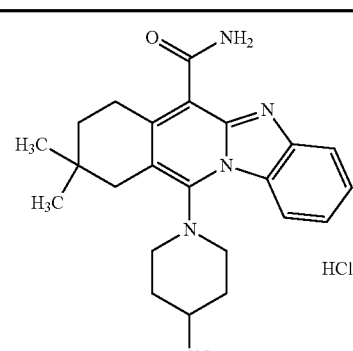 HCl |
| A265 | 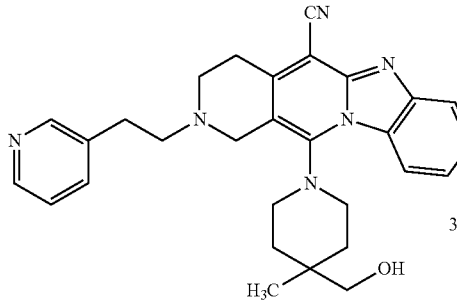 3HCl |
| A266 | 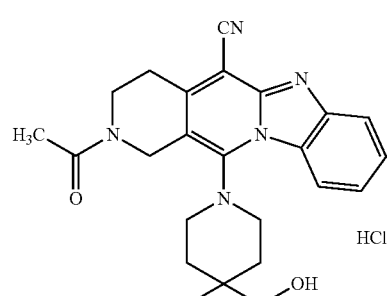 HCl |
| A267 | 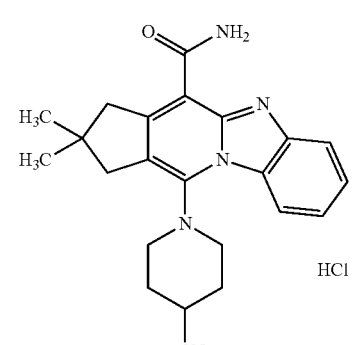 HCl |

TABLE 45-continued
| No. | Str |
|---|---|
| A268 | 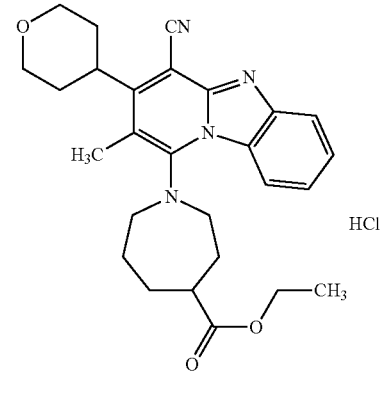 [SMILES: CCOC(=O)C1CCCN(c2c(C)c(C3CCOCC3)c(C#N)c3nc4ccccc4n23)CC1 ; Cl] 2HCl |
TABLE 46
| No. | Str |
|---|---|
| A269 | 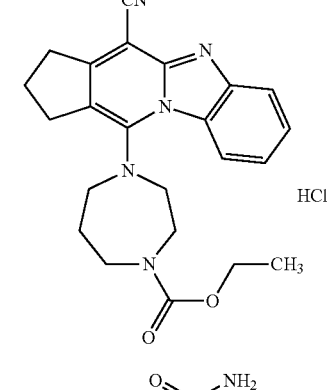 HCl |
| A270 | 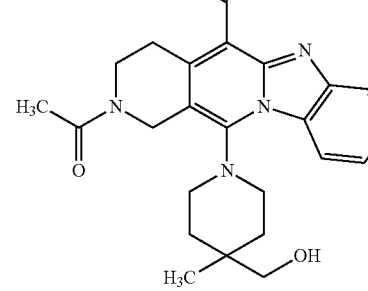 HCl |
| A271 | 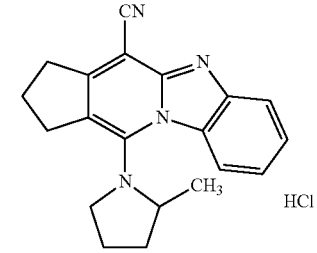 [SMILES: CC1CCCN1c1c2c(c(C#N)c3nc4ccccc4n13)CCC2 ; Cl] HCl |
TABLE 46-continued
| No. | Str |
|---|---|
| A272 | 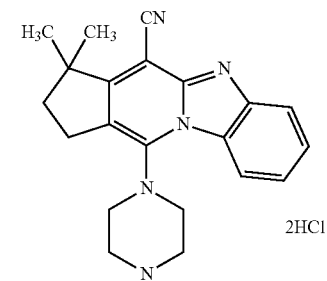 HCl |
| A273 | 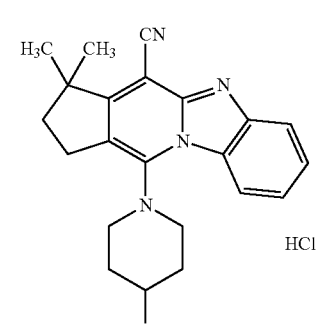 2HCl |
| A274 | 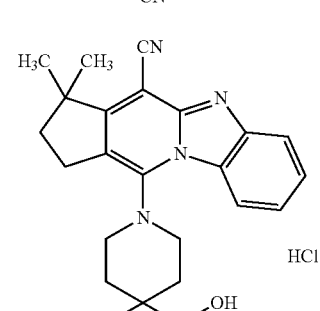 HCl |
| A275 | 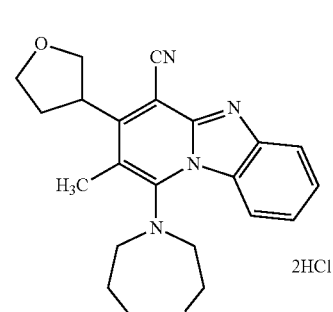 HCl |
| A276 |  2HCl |

TABLE 47
| No. | Str |
|---|---|
| A277 | 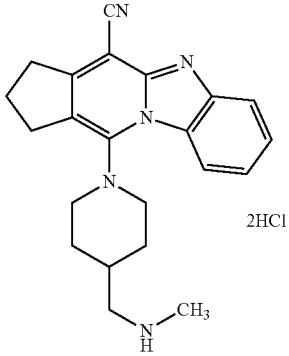 [SMILES: CNCC1CCN(c2c3c(c(C#N)c4nc5ccccc5n24)CCC3)CC1 ; "2HCl"] 2HCl |
| A278 | 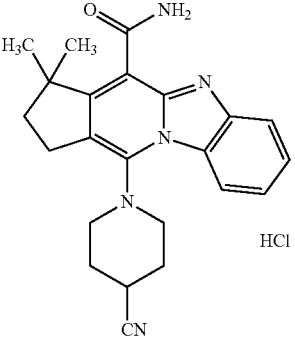 [SMILES: CC1(C)CCc2c1c(C(N)=O)c1nc3ccccc3n1c2N1CCC(C#N)CC1 ; Cl] HCl |
| A279 | 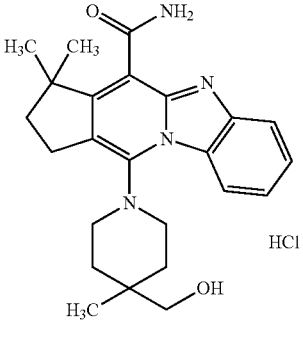 [SMILES: CC1(CO)CCN(c2c3c(c(C(N)=O)c4nc5ccccc5n24)C(C)(C)CC3)CC1 ; Cl] HCl |
| A280 | 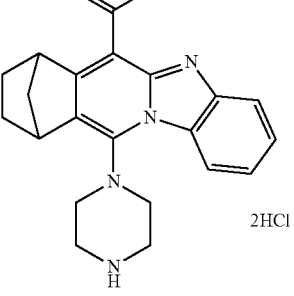 2HCl |
TABLE 47-continued
| No. | Str |
|---|---|
| A281 | 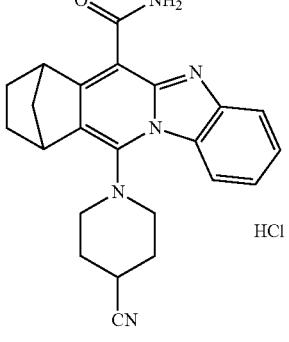 HCl |
| A282 | 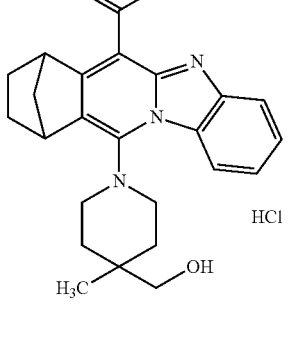 HCl |
| A283 | 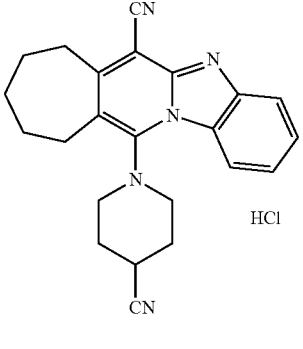 [SMILES: N#Cc1c2c(c(N3CCC(C#N)CC3)n3c1nc1ccccc13)CCCCC2 ; Cl] HCl |
| A284 | 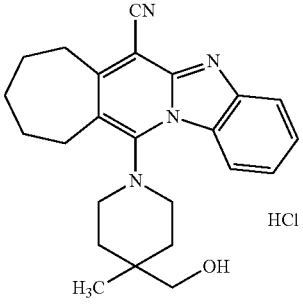 [SMILES: CC1(CO)CCN(c2c3c(c(C#N)c4nc5ccccc5n24)CCCCC3)CC1 ; Cl] HCl |

TABLE 48

| No. | Str |
| --- | --- |
| A285 | (structure with cycloheptane-fused pyridobenzimidazole, carboxamide, 4-methyl-4-hydroxymethylpiperidine, HCl) |
| A286 | (cyclopenta-fused pyridobenzimidazole with CN, 4-(2-hydroxyethyl)piperidine, HCl) |
| A287 | (cyclopenta-fused pyridobenzimidazole with CN, 4-(fluoromethyl)piperidine, HCl) |
| A288 | (pyridobenzimidazole carboxamide with methyl and benzyl substituents, 4-methyl-4-hydroxymethylpiperidine, HCl) |

TABLE 48-continued

| No. | Str |
| --- | --- |
| A289 | (cyclopenta-fused pyridobenzimidazole with CN, 3-(2-hydroxyethyl)pyrrolidine, HCl) |
| A290 | (cyclopenta-fused pyridobenzimidazole with CN, 3-(2-fluoroethyl)pyrrolidine, HCl) |
| A291 | (cyclopenta-fused pyridobenzimidazole with CN, 3-azabicyclo[3.1.0]hexane with hydroxymethyl, HCl) |
| A292 | (cyclopenta-fused pyridobenzimidazole with CN, 3-azabicyclo[3.1.0]hexane with hydroxymethyl stereoisomer, HCl) |

TABLE 49
| No. | Str |
|---|---|
| A293 | 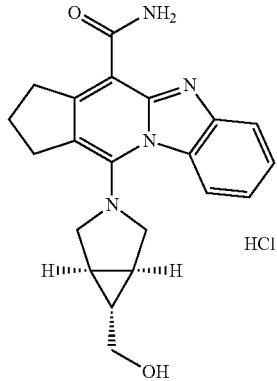 [SMILES: NC(=O)c1c2c(c(N3C[C@@H]4[C@@H](CO)[C@@H]4C3)n3c1nc1ccccc13)CCC2 ; Cl] HCl |
| A294 | 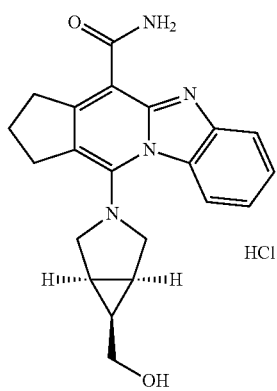 [SMILES: NC(=O)c1c2c(c(N3C[C@@H]4[C@H](CO)[C@@H]4C3)n3c1nc1ccccc13)CCC2 ; Cl] HCl |
| A295 | 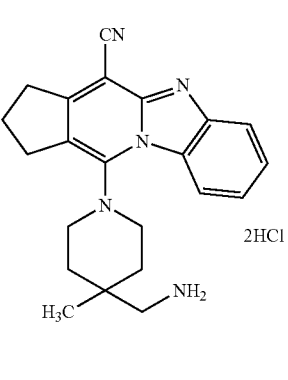 [SMILES: CC1(CN)CCN(c2c3c(c(C#N)c4nc5ccccc5n24)CCC3)CC1 ; "2HCl"] 2HCl |
| A296 | 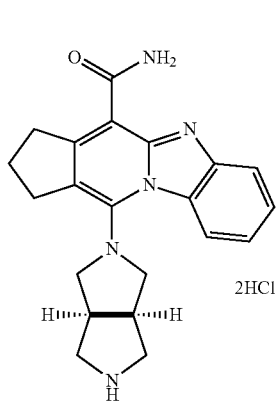 2HCl |
TABLE 49-continued
| No. | Str |
|---|---|
| A297 | 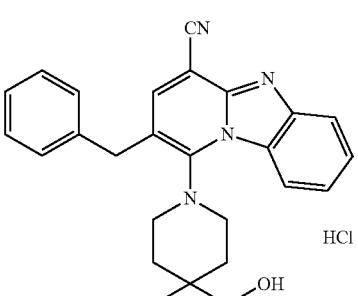 HCl |
| A298 | 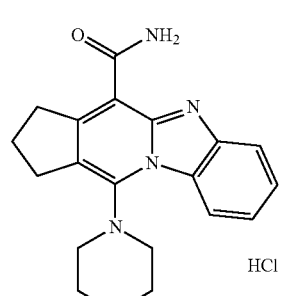 HCl |
| A299 | 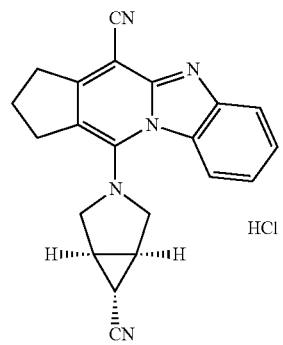 [SMILES: N#Cc1c2c(c(N3C[C@@H]4[C@@H](C#N)[C@@H]4C3)n3c1nc1ccccc13)CCC2 ; Cl] HCl |
| A300 | 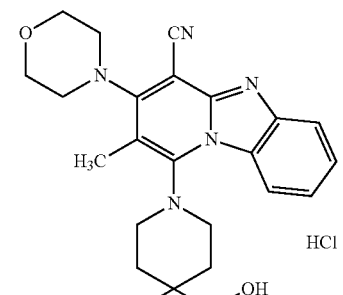 HCl |

TABLE 50
| No. | Str |
|-----|-----|
| A301 | 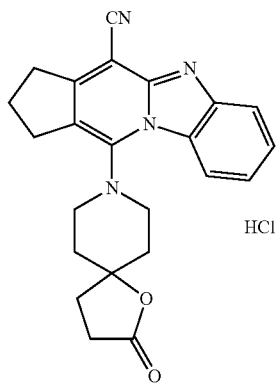 [SMILES: N#Cc1c2c(c(N3CCC4(CCC(=O)O4)CC3)n3c1nc1ccccc13)CCC2 ; Cl] HCl |
| A302 | 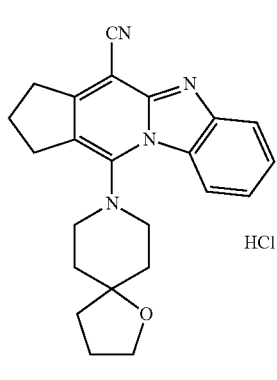 [SMILES: N#Cc1c2c(c(N3CCC4(CCCO4)CC3)n3c1nc1ccccc13)CCC2 ; Cl] HCl |
| A303 | 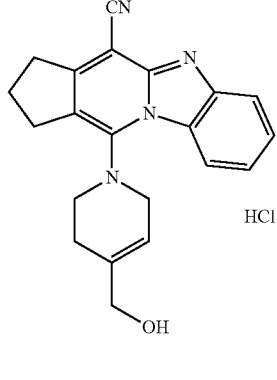 [SMILES: N#Cc1c2c(c(N3CC=C(CO)CC3)n3c1nc1ccccc13)CCC2 ; Cl] HCl |
| A304 | 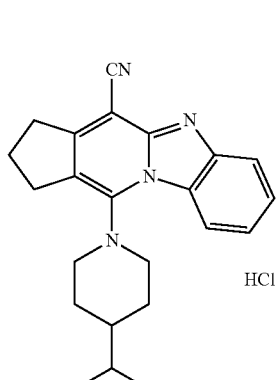 HCl |
TABLE 50-continued
| No. | Str |
|-----|-----|
| A305 | 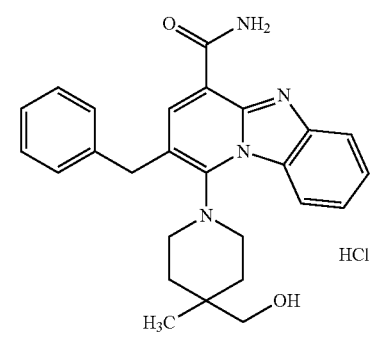 [SMILES: CC1(CO)CCN(c2c(Cc3ccccc3)cc(C(N)=O)c3nc4ccccc4n23)CC1 ; Cl] HCl |
| A306 | 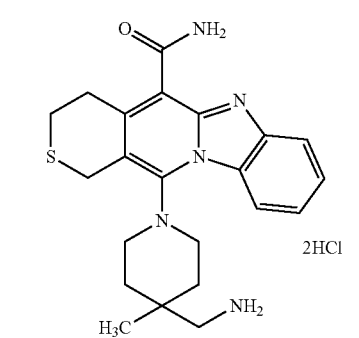 [SMILES: CC1(CN)CCN(c2c3c(c(C(N)=O)c4nc5ccccc5n24)CCSC3)CC1 ; "2HCl"] 2HCl |
| A307 | 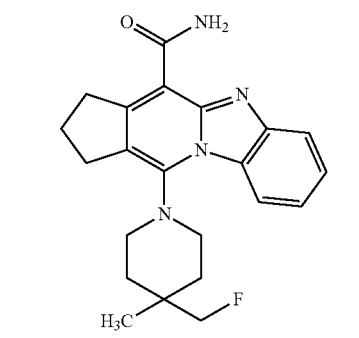 [SMILES: CC1(CF)CCN(c2c3c(c(C(N)=O)c4nc5ccccc5n24)CCC3)CC1] |
| A308 | 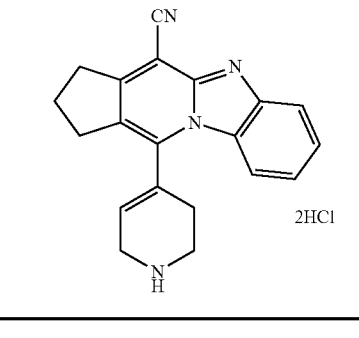 2HCl |

TABLE 51
| No. | Str |
|---|---|
| A309 | 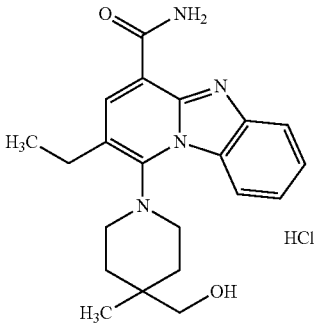 [SMILES: CCc1cc(C(N)=O)c2nc3ccccc3n2c1N1CCC(C)(CO)CC1 ; Cl] HCl |
| A310 | 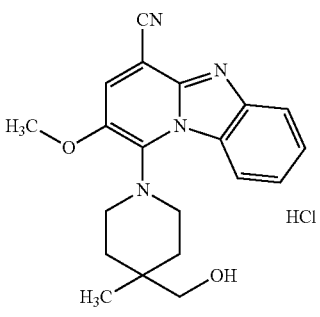 [SMILES: COc1cc(C#N)c2nc3ccccc3n2c1N1CCC(C)(CO)CC1 ; Cl] HCl |
| A311 | 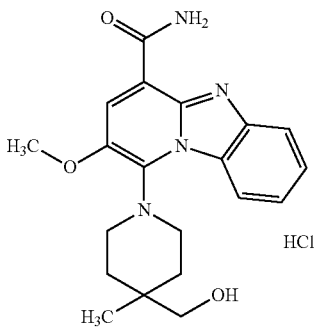 HCl |
| A312 | 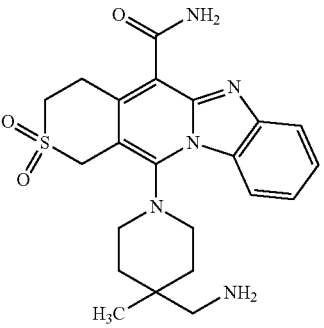 [SMILES: CC1(CN)CCN(c2c3c(c(C(N)=O)c4nc5ccccc5n24)CCS(=O)(=O)C3)CC1] |
TABLE 51-continued
| No. | Str |
|---|---|
| A313 | 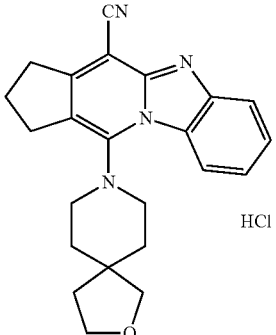 HCl |
| A314 | 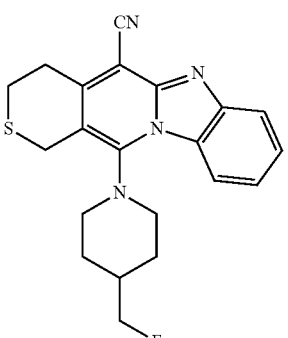 |
| A315 | 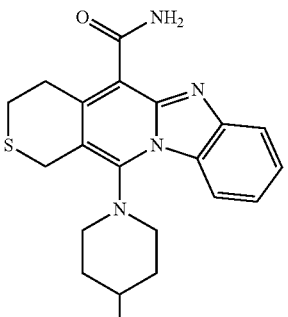 |
| A316 | 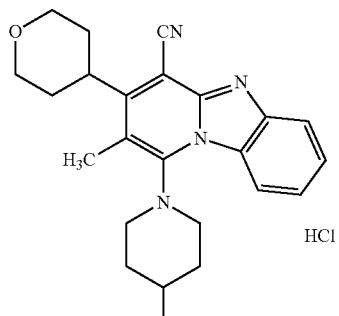 HCl |

TABLE 52
| No. | Str |
|---|---|
| A317 | 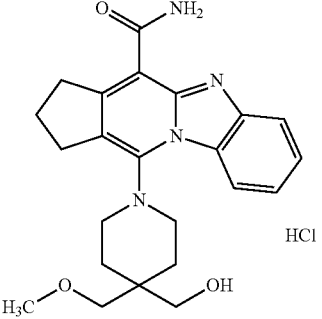 [SMILES: COCC1(CO)CCN(c2c3c(c(C(N)=O)c4nc5ccccc5n24)CCC3)CC1 ; Cl] HCl |
| A318 | HCl |
| A319 | HCl |
| A320 | HCl |
TABLE 52-continued
| No. | Str |
|---|---|
| A321 | HCl |
| A322 | HCl |
| A323 | HCl |
| A324 | HCl |

TABLE 53
| No. | Str |
|---|---|
| A325 | 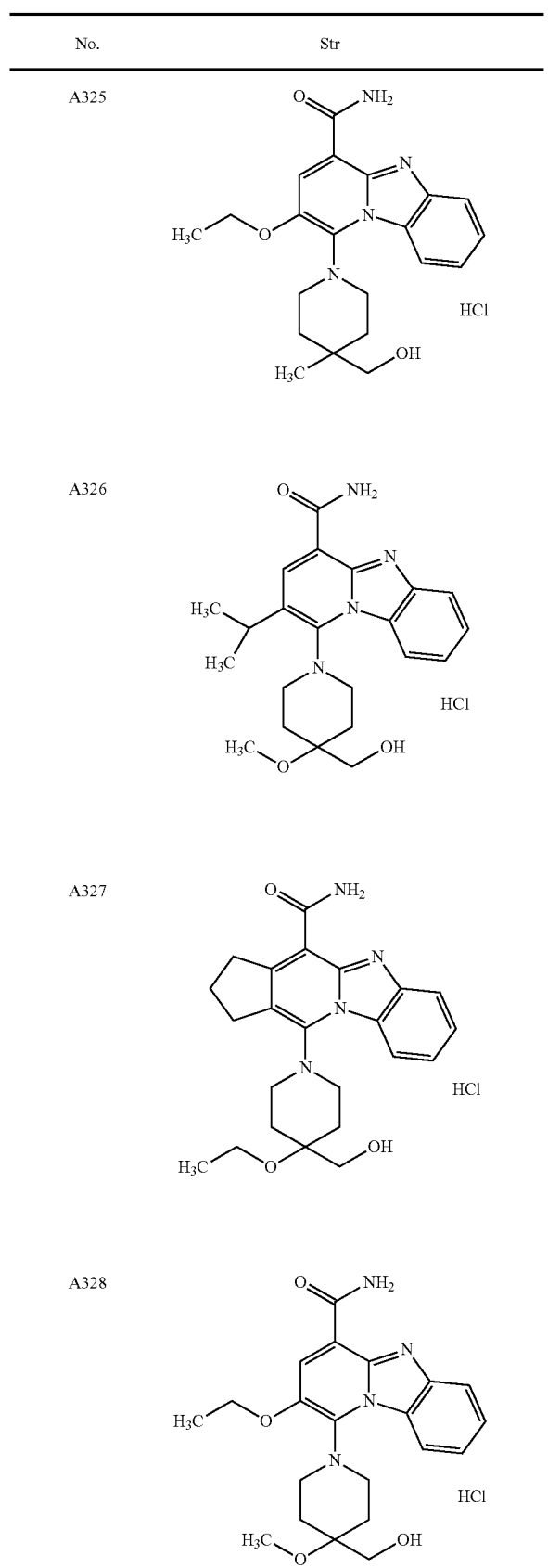 |
| A326 | |
| A327 | |
| A328 | |
TABLE 53-continued
| No. | Str |
|---|---|
| A329 | 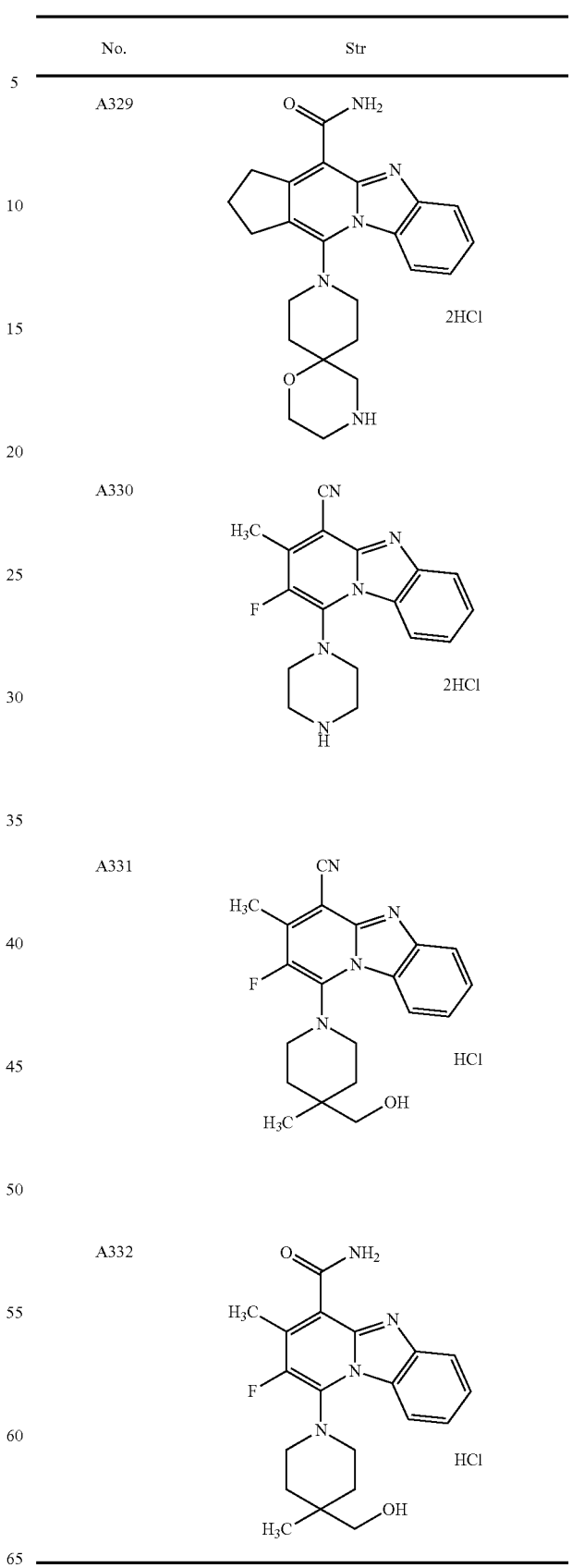 |
| A330 | |
| A331 | |
| A332 | |

TABLE 54

| No. | Str |
|---|---|
| A333 | (structure with CN, cyclopentane-fused, benzimidazole, piperidine-spiro-cyclopropane with OH) |
| A334 | (carboxamide, cyclopentane-fused benzimidazole, pyrrolidine-spiro-piperidine, 2HCl) |
| A335 | (carboxamide, H3C-S substituent, benzimidazole, piperidine with CH2OH and OCH3, HCl) |
| A336 | (carboxamide, H3C-S(=O) substituent, benzimidazole, piperidine with CH2OH and OCH3, HCl) |

TABLE 54-continued

| No. | Str |
|---|---|
| A337 | (carboxamide, H3C-SO2 substituent, benzimidazole, piperidine with CH2OH and OCH3) |
| A338 | (carboxamide, isobutyl substituent, benzimidazole, piperidine with CH2OH and OCH3, HCl) |
| A339 | (carboxamide, methoxyethyl substituent, benzimidazole, piperidine with CH2OH and OCH3, HCl) |

INDUSTRIAL APPLICABILITY

The compound of formula (I) or a pharmaceutically acceptable salt thereof have a PDE4B inhibitory action and can be used as an agent for the treatment or prevention of schizophrenia, Alzheimer's disease, dementia, or depression.

The invention claimed is:

1. A compound of formula (I) or a pharmaceutically acceptable salt thereof:

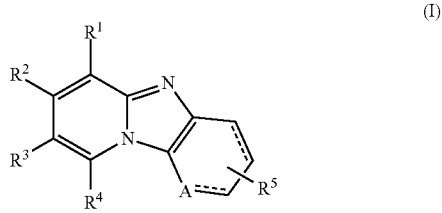

(I)

wherein:

R¹ is —CONH₂;

R² and R³ are bonded together to form a cycloalkyl ring or a monocyclic saturated hetero ring in which one cyclic atom is a hetero atom, which is condensed with the adjacent ring, wherein the cycloalkyl ring and the monocyclic saturated hetero ring may have bridge(s) and may have 1 to 5 substituent(s) selected from the group consisting of halogen, lower alkyl, mono-OH substituted lower alkyl, di-OH substituted lower alkyl, -lower alkylene amine, —O-lower alkyl, cyano, aryl, a heterocyclic group, and acyl;

R⁴ is a heterocyclic group which may have 1 to 5 substituents selected from the group consisting of lower alkyl, mono-OH substituted lower alkyl, di-OH substituted lower alkyl, —O-lower alkyl, -lower alkylene-(amine which may be protected), cyano, and halogen;

R⁵ is —H;

A represents CH or CH₂; and a dotted line represents that the site may form a double bond.

2. The compound or pharmaceutically acceptable salt thereof according to claim 1, wherein R² and R³ are bonded together to form a group selected from the group consisting of wherein n¹ is 1 or 2;

R⁷ are the same or different and are H or methyl; and

R⁴ is a heterocyclic group selected from the group consisting of wherein the hetero ring is substituted with 1 to 5 substituents selected from the group consisting of lower alkyl, mono- or di-OH substituted lower alkyl, —O-lower alkyl, -lower alkylene-(amine which may be protected), cyano, and halogen.

3. The compound or pharmaceutically acceptable salt thereof according to claim 2, which is represented by formula (I-b)

(I-b)

wherein:

R⁷ is H or methyl; and

R⁸ are the same or different and represent a substituent selected from the group consisting of H, methyl, —CH₂OH, —O—CH₃, —CH₂NH₂, cyano and —F.

4. The compound or pharmaceutically acceptable salt thereof according to claim 1, which is a compound selected from the group consisting of rel-11-[(3R,4S)-3-fluoro-4-(hydroxymethyl)-4-methoxypiperidin-1-yl]-2,2-dimethyl-2,3-dihydro-1H-cyclopenta[4,5]pyrido[1,2-a]benzimidazole-4-carboxamide, 11-[4-(hydroxymethyl)-4-methoxypiperidin-1-yl]-2,3-dihydro-1H-cyclopenta[4,5]pyrido[1,2-a]benzimidazole-4-carboxamide, rel-11-[(3R,4S)-3-fluoro-4-(hydroxymethyl)-4-methoxypiperidin-1-yl]-2,3-dihydro-1H-cyclopenta[4,5]pyrido[1,2-a]benzimidazole-4-carboxamide, 11-[4-(hydroxymethyl)-4-methoxypiperidin-1-yl]-2,2-dimethyl-2,3-dihydro-1H-cyclopenta[4,5]pyrido[1,2-a]benzimidazole-4-carboxamide, 11-[4-(hydroxymethyl)-4-methoxypiperidin-1-yl]-7,8,9,10-tetrahydro-7,10-methanobenzimidazo[1,2-b]isoquinoline-6-carboxamide, 11-[4-(hydroxymethyl)-4-methylpiperidin-1-yl]-9,9-dimethyl-7,8,9,10-tetrahydrobenzimidazo[1,2-b]isoquinoline-6-carboxamide, and 11-[4-(hydroxymethyl)-4-methylpiperidin-1-yl]-2,3-dihydro-1H-cyclopenta[4,5]pyrido[1,2-a]benzimidazole-4-carboxamide, or a pharmaceutically acceptable salt of said compound.

5. A pharmaceutical composition comprising a compound or a pharmaceutically acceptable salt thereof according to claim 4 and a pharmaceutically acceptable excipient.

6. The pharmaceutical composition according to claim 5, which is a PDE4B inhibitor.

7. The pharmaceutical composition according to claim 5, for treatment of schizophrenia, Alzheimer's disease, dementia, or depression.

8. The compound or pharmaceutically acceptable salt thereof according to claim 4, for treatment of schizophrenia, Alzheimer's disease, dementia, or depression.

9. A method of treating schizophrenia, Alzheimer's disease, dementia, or depression, which comprises administering an effective amount of a compound or a salt thereof according to claim 4 to a patient in need thereof.

10. The compound or pharmaceutically acceptable salt thereof according to claim 1, which is 11-[4-(hydroxymethyl)-4-methoxypiperidin-1-yl]-2,3-dihydro-1H-cyclopenta[4,5]pyrido[1,2-a]benzimidazole-4-carboxamide or a pharmaceutically acceptable salt thereof.

11. The compound or pharmaceutically acceptable salt thereof according to claim 1, which is 11-[4-(hydroxymethyl)-4-methoxypiperidin-1-yl]-2,2-dimethyl-2,3-dihydro-1H-cyclopenta[4,5]pyrido[1,2-a]benzimidazole-4-carboxamide or a pharmaceutically acceptable salt thereof.

12. The compound or pharmaceutically acceptable salt thereof according to claim 1, which is 11-[4-(hydroxymethyl)-4-methylpiperidin-1-yl]-2,3-dihydro-1H-cyclopenta[4,5]pyrido[1,2-a]benzimidazole-4-carboxamide or a pharmaceutically acceptable salt thereof.

\* \* \* \* \*